US008921279B2

(12) United States Patent
Himmler et al.

(10) Patent No.: US 8,921,279 B2
(45) Date of Patent: Dec. 30, 2014

(54) DISPLAY OF BINDING AGENTS

(75) Inventors: Gottfried Himmler, Grossenzersdorf (AT); Florian Ruker, Vienna (AT); Gerda Redl, Gross-Enzersdorf (AT); Gordana Wozniak-Knopp, Vienna (AT); Geert Mudde, Breitenfurt (AT)

(73) Assignee: F-Star Biotechnologische Forschungs—und Entwicklungsges. m.b.H, Vienna (AT)

( * ) Notice: Subject to any disclaimer, the term of this patent is extended or adjusted under 35 U.S.C. 154(b) by 907 days.

(21) Appl. No.: 12/666,618

(22) PCT Filed: Jun. 26, 2008

(86) PCT No.: PCT/AT2008/000232
§ 371 (c)(1),
(2), (4) Date: Dec. 23, 2009

(87) PCT Pub. No.: WO2009/000006
PCT Pub. Date: Dec. 31, 2008

(65) Prior Publication Data
US 2010/0184615 A1    Jul. 22, 2010

Related U.S. Application Data

(60) Provisional application No. 60/946,287, filed on Jun. 26, 2007, provisional application No. 61/049,826, filed on May 2, 2008.

(51) Int. Cl.
*C40B 30/04*    (2006.01)
*C07K 16/32*    (2006.01)
*C07K 16/00*    (2006.01)

(52) U.S. Cl.
CPC .............. *C07K 16/005* (2013.01); *C07K 16/32* (2013.01); *C07K 2317/569* (2013.01); *C07K 2317/52* (2013.01); *C07K 2318/10* (2013.01)
USPC ............................................................ 506/9

(58) Field of Classification Search
None
See application file for complete search history.

(56) References Cited

U.S. PATENT DOCUMENTS

| 5,223,409 | A | 6/1993 | Ladner et al. |
| 5,759,817 | A | 6/1998 | Barbas |
| 6,057,098 | A | 5/2000 | Buechler et al. |
| 2004/0146976 | A1 | 7/2004 | Wittrup et al. |
| 2006/0140934 | A1 | 6/2006 | Gegg et al. ................. 424/133.1 |

FOREIGN PATENT DOCUMENTS

| WO | WO 92/09690 | 6/1992 |
| WO | WO 00/71694 | 11/2000 |
| WO | WO 03/029456 | 4/2003 |
| WO | WO 2006/033700 | 3/2006 |

(Continued)

OTHER PUBLICATIONS

Braren et al. (Mar. 21, 2007) Biotechnol Appl Biochem vol. 47 pp. 205 to 214.*

(Continued)

*Primary Examiner* — Christian Boesen
(74) *Attorney, Agent, or Firm* — Sunstein Kann Murphy & Timbers LLP

(57) ABSTRACT

The present invention relates to a method of preparing a genetic package displaying oligomers of modular antibody domains binding to a target and to a scaffold ligand as well as to vectors and libraries of genetic packages produced thereby. The invention further relates to methods of selecting suitable linker sequences for use in such oligomer display.

6 Claims, 2 Drawing Sheets

Figure 1:
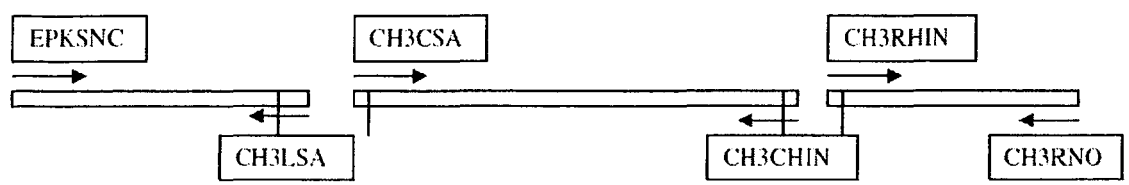

| | | | | | | | | | | | | | | | | | | | | | | | |
|---|---|---|---|---|---|---|---|---|---|---|---|---|---|---|---|---|---|---|---|---|---|---|---|
| Wt | T | K | N | | | | | D | K | S | | | | | | R | W | | Q | Q | | | |
| Fcab01 | x | x | x | | | | | x | x | x | x | x | x | x | x | R | W | | x | x | | | |
| Fcab02 | z | z | z | | | | | z | z | z | z | z | z | z | z | R | W | | z | z | | | |
| Fcab03 | x | x | x | | | G | S | x | x | x | x | x | x | x | x | S | G | R | W | | x | x |
| Fcab04 | z | z | z | | | G | S | z | z | z | z | z | z | z | z | S | G | R | W | | z | z |
| Fcab05 | z | x | x | x | x | z | | x | x | x | x | x | x | x | x | R | W | | x | x | | | |
| Fcab06 | z | z | z | z | z | | | z | z | z | z | z | z | z | z | R | W | | z | z | | | |

(56) References Cited

FOREIGN PATENT DOCUMENTS

| WO | WO 2006/036834 A2 | 4/2006 | ............ C07K 19/00 |
| WO | WO 2006/072620 | 7/2006 | |
| WO | WO 2008/003116 | 1/2008 | |

OTHER PUBLICATIONS

International Search Report, International Patent Application No. PCT/AT2008/000232, Oct. 13, 2008.
International Preliminary Report on Patentability, International Patent Application No. PCT/AT2008/000232, Jan. 5, 2010.
Written Opinion of the International Searching Authority, International Patent Application No. PCT/AT2008/000232, Oct. 13, 2008.
Communication pursuant to Article 94(3) EPC, European Patent Application No. 08 756 842.4-2406, Jun. 14, 2010.
Dall' Acqua et al., The Journal of Immunology, 2002, 169: 5171-5180.
Berry JD, Hybrid. Hybridomics, Apr. 22, 2003(2), pp. 97-108.
Rondot S et al., Nat. Biotechnol., Jan. 19, 2001, (1), pp. 75-78.
Virnekas et al., Nucleic Acids Res. 1994, 22:5600-5607.
Kunkel TA et al., Proc Natl Acad Scie USA, Jan. 1985 82(2), pp. 488-492.
Weiner MP et al., Gene. Dec. 30, 1994, 151(1-2), pp. 119-123.
Hayhurst A & Georgiou, 2001, Curr Opin Chem Biol 5:683-689.
Hoogenboom HR et al., Nucleic Acids Res., Aug. 11, 1991, 19(15), pp. 4133-4137.
Felgenhauer M et al., Nucleic Acids Res. Aug. 25, 1990, 18(16), p. 4927.
Fellouse FA et al., J Mol. Biol 2005, May 20, 2005, 348(5), pp. 1153-1162 (Epub Apr. 1, 2005).
Fellouse FA et al., Proc Natl. Acad Scie USA Aug. 24, 2004 101(34), pp. 12467-12472 (Epub Aug. 11, 2004).
Sidhu SS, Fellouse FA, Nature Chemical Biology 2006, vol. 2, pp. 682-688.
Koide et al., PNAS, 104:6632-6637 (2007).
Wittrup, 2001, Curr Opin Biotechnol, 12:395-399.
Gao Changshou et al., Proceedings of the National Academiy of Sciences of USA, vol. 96, 11, May 25, 1999, pp. 6025-6030.
Vajdos F F et al., Journal of Molecular Biology, vol. 320, No. 2, Jul. 5, 2002, pp. 415-428.
Spiridon Camelia I et al., Clinical Cancer Research, The American Association for Cancer Research, vol. 8, No. 6, pp. 1720-1730, Jun. 1, 2002.

\* cited by examiner

DISPLAY OF BINDING AGENTS

CROSS-REFERENCE TO RELATED APPLICATIONS

This application is the U.S. national stage of International Patent Application No. PCT/AT2008/000232, filed on Jun. 26, 2008 and entitled DISPLAY OF BINDING AGENTS, which claims the benefit of priority from U.S. Patent Application No. 60/946,287, filed on Jun. 26, 2007 and entitled MULTIVALENT DISPLAY OF BINDING AGENTS, and from U.S. Patent Application No. 61/049,826, filed on May 2, 2008 and entitled DISPLAY OF BINDING AGENTS. The disclosures of the foregoing applications are incorporated herein by reference in their entirety.

FIELD OF THE INVENTION

The invention relates to a method of preparing a genetic package displaying oligomers of modular antibody domains binding to a target and to a scaffold ligand and vectors and libraries of bivalent genetic packages produced by these methods. The invention further relates to methods of selecting suitable linker sequences for use in such oligomer display.

BACKGROUND

Monoclonal antibodies have been widely used as a scaffold for binding agents. The basic antibody structure will be explained here using as example an intact IgG1 immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgG1 two disulfide bonds in the hinge region, between Cys235 and Cys238 pairs, unite the two heavy chains. The light chains are coupled to the heavy chains by two additional disulfide bonds, between Cys229s in the CH1 domains and Cys214s in the CL domains. Carbohydrate moieties are attached to Asn306 of each CH2, generating a pronounced bulge in the stem of the Y.

These features have profound functional consequences. The variable regions of both the heavy and light chains (VH) and (VL) lie at the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Two types of light chain, termed lambda (λ) and kappa (κ), are found in antibodies. A given immunoglobulin either has κ chains or λ chains, never one of each. No functional difference has been found between antibodies having λ or κ light chains.

Each domain in an antibody molecule has a similar structure of two beta sheets packed tightly against each other in a compressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

The fold of variable domains has 9 beta strands arranged in two sheets of 4 and 5 strands. The 5-stranded sheet is structurally homologous to the 3-stranded sheet of constant domains, but contains the extra strands C' and C". The remainder of the strands (A, B, C, D, E, F, G) have the same topology and similar structure as their counterparts in constant domain immunoglobulin folds. A disulfide bond links strands B and F in opposite sheets, as in constant domains.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

The loops which are not CDR-loops in a native immunoglobulin, or not part of the antigen-binding pocket as determined by the CDR loops and optionally adjacent loops within the CDR loop region, do not have antigen binding or epitope binding specificity, but contribute to the correct folding of the entire immunoglobulin molecule and/or its effector or other functions and are therefore called structural loops for the purpose of this invention.

Prior art documents show that the immunoglobulin-like scaffold has been employed so far for the purpose of manipulating the existing antigen binding site, thereby introducing novel binding properties. In most cases the CDR regions have been engineered for antigen binding, in other words, in the case of the immunoglobulin fold, only the natural antigen binding site has been modified in order to change its binding affinity or specificity. A vast body of literature exists which describes different formats of such manipulated immunoglobulins, frequently expressed in the form of single-chain Fv fragments (scFv) or Fab fragments, either displayed on the surface of phage particles or solubly expressed in various prokaryotic or eukaryotic expression systems.

WO06072620A1 describes a method of engineering an immunoglobulin which comprises a modification in a structural loop region to obtain new antigen binding sites. This method is broadly applicable to immunoglobulins and may be used to produce a series of immunoglobulins targeting a variety of antigens. A CH3 library has been shown to be useful for selecting specific binders to an antigen.

Although multivalent display of proteins on genetic packages has been described (such as direct phage cloning and display, bacterial display, yeast display), prior art refers to monomeric monovalent display of binding domains, in general. WO9209690 describes phagemid particles displaying a single copy of a fusion protein on the surface of the particle. Thereby it was described to obtain high affinity binders from a library of phagemid particles, also called bacteriophages. Replicable expression vectors comprising genes encoding a binding polypeptide and a phage coat protein are provided so to form a gene fusion encoding a fusion protein, which is a chimeric protein of a phagemid particle, the phage coat protein and the binding polypeptide.

U.S. Pat. No. 5,223,409 generally describes the method of fusing a gene encoding a protein of interest to the N-terminal domain of the gene III coat protein of the filamentous phage M13. The gene fusion is mutated to form a library of structurally related fusion proteins that are expressed in low quantity on the surface of a phagemid particle. Biological selection and screening is employed to identify novel ligands useful as drug candidates.

However, there are some limitations in using such "fusion phage" or monovalent phage display and respective single fusion proteins. Many biologicals naturally occur in oligomeric form. For the purpose of the present invention oligomeric means dimeric, trimeric or even higher polymeric forms, up to 24 monomers.

The fusion phages according to the prior art are described to display monomeric fusion proteins, mainly because it was believed that binders of highest affinity could only be selected from a library if single fusion proteins are displayed by the phagemid particles. Native proteins are however often assembled as a dimer or even at a higher degree of oligomerization. To obtain dimeric display with a single fusion protein, some techniques have been developed that involve conditional stop codons located between the coat protein and the binding polypeptide (Dall'Acqua et al The Journal of Immunology, 2002, 169: 5171-5180). Thereby soluble monomers of the polypeptides in addition to those fused to the phage are expressed, thus enabling the formation of a dimer. However, such stop codons requires propagation in specific suppressor host cells that may translate a stop codon in an amino acid, to provide an appropriate amount of fusion proteins in addition to the soluble binding polypeptides. WO 03/029456 describes the use of multi-chain eukaryotic display vectors for the selection of immunoglobulin Fab fragments on the surface of yeast cells.

Prior art fusion proteins involve in some cases linker sequences to display larger binding polypeptides. Linker sequences of up to 24 amino acids are usually employed for standard purposes of displaying variable domains of an antibody. See for example, the display vector pCOMB3x (Hybrid. Hybridomics. 2003 April; 22(2):97-108. Development of functional human monoclonal single-chain variable fragment antibody against HIV-1 from human cervical B cells. Berry J D, Rutherford J, Silverman G J, Kaul R, Elia M, Gobuty S, Fuller R, Plummer F A, Barbas C F.)

It is an object of this invention to provide an effective method for the preparation of oligomers of modular antibody domains and to prepare such oligomers displayed on the surface of a replicable genetic package.

BRIEF DESCRIPTION OF THE INVENTION

The objects are solved by the subject matter of the present invention.

According to the invention a method of preparing a genetic package displaying oligomers of modular antibody domains binding to a target and to a scaffold ligand comprising
    providing a genetic package, and
    displaying at least two of the antibody modular domains by fusing to the outer surface of the package
is covered.

The genetic package can be displayed in a mobilized or cellular system, wherein according to the invention the mobilized system can be selected from viruses, phages, phagemids, in-vitro display systems, mRNA systems and ribosomal display systems. Alternatively, a cellular system can be selected using yeast, mammalian cells, bacterial cells, bacterial spores or insect cells.

Oligomers are possibly formed by oligomerization motifs associated with the structure of said agents, such as leucine zipper, disulfide bonds, electrostatic or hydrophobic motifs.

According to one embodiment of the invention the oligomers can be dimers, trimers or tetramers, involving the same type of monomers (homomers) or different types (heteromers). The preferred method according to the invention is specifically useful for providing homomers, in particular homodimers of oligonucleotides on a genetic package, such as a phagemid particle or a phage or yeast.

The method according to the invention can be applied to oligomers which are polypeptides with a target binding site that directs towards the surface of the genetic package and is close to said surface that are biologicals, such as polypeptides.

Alternatively, the appropriate design of such a polypeptide is employed with a binding site that is closer to the surface of the genetic package than to the surrounding environment of the genetic package. This may be advantageous for a binding polypeptide with a potential binding site that is closer to the C-terminus than to the N-terminus of the polypeptide, in particular when the binding site is engineered in a C-terminal loop position. When the potential binding site is engineered at a position that is adjacent to the site where the genetic package particle is bound, for instance to a surface structure of a cell or a virus, it is advantageous to choose a stable construct with defined accessibility of the binding partner of said binding agent. C-terminal loop positions are, for instance, less accessible than N-terminal loop positions, when they are fused to the N-terminus of the protein 3 of a filamentous phage because they are exposed and in sterical proximity to the genetic package.

According to a preferred embodiment of the invention, however, a defined structure, such as a true oligomeric or dimeric fusion protein is provided to enable the efficient engineering of the potential binding site at an N-terminal loop position. One embodiment of the invention refers to polypeptides with at least two target binding sites, possibly engineered at the monomeric or the oligomeric target binding agent. In some cases the interaction between the monomeric structures enables additional variations of structures and thus additional potential binding sites.

According to a preferred embodiment of the invention the modular antibody is an antibody, Fc fragment, an antibody fragment with a CDR region and combinations thereof, possibly also comprising a fragment with a binding site at a structural loop position.

It can also be an antibody fragment with a CDR region like for example Fab, dAb, scFv, diabody, unibody, SMIPs, TANDABS, Fc fusion proteins and combinations thereof.

In case the genetic package is a filamentous bacteriophage, the preferred fusion structure employed with a bacteriophage involves at least part of an outer surface protein, such as p3, p6, or p8, however, p9 or p10 may also be used for the purpose of the invention.

In case the genetic package is yeast it is preferred that the oligomer is a fusion protein comprising one of the proteins of yeast cell surface receptors selected from the group consisting of alpha-agglutinin, a-agglutinin, Aga1p, Aga2p or FLO1.

The appropriate genetic package is preferably provided in a particular form, and containing a vector encoding at least one of said fusion proteins. According to the invention there is, for example, provided a cassette vector, containing sequences encoding one or more than one fusion protein operatively linked to the genetic package. Thus, at least two of the chimeric fusion proteins are bound at the surface of the vector particle. The vector can be, for example, a phagemid.

An expression system for expressing oligomers of modular antibody domains bound at the surface of a genetic package produced according to the inventive method is also covered wherein the oligomers are encoded by a single gene and the fusion protein is displayed with at least two copies on the surface of the genetic package.

By using the method and means according to the invention it is possible to display oligomers of modular antibodies without the need of controlled expression of a soluble form of one of the oligomerization partners. The technique can be utilized for molecules such as antibody fragments, even those containing more than two immunoglobulin domains, e.g. at least four immunoglobulin domains. Thus difficult constructs involving stop codons, such as amber stop codons, can be avoided. There will be no need to get a mixture of fusion proteins and soluble monomers for the dimer display. Thus, a preferred technique of managing mixtures of a variety of binding agents can easily be employed, while the risk of insufficient matching of the monomers is reduced. It is also possible to avoid the suppressor strains as a host cell. Conventional host cells, with non-suppressor function, can serve in a standard way to propagate the oligomeric fusion proteins.

In another embodiment according to the invention, the fusion between the binding partner and the surface protein of the genetic package is such that no conditional stop codon (i.e. no amber, ochre, opal or other similar conditional stop codon) is present in between. In such a situation, upon infection with helper phage, the binding partner is present only as a fusion protein and not in soluble form. In order for the dimer (trimer or higher) to form on the surface of the genetic package, the linker which connects the binding partner to the genetic package needs to be of sufficient length and sufficient flexibility. Linkers that fulfil this requirement can be selected using the method described above.

In another embodiment according to the invention, a helper phage can be used that has specific properties that favour the display of more than one copy of the fusion protein on the surface of the genetic package. An example for such a helper phage is the so-called hyperphage (Rondot S, Koch J, Breitling F, Dubel S. A helper phage to improve single-chain antibody presentation in phage display. Nat. Biotechnol. 2001 January; 19(1):75-78), which itself is devoid of p3, and therefore depends totally on the p3 fusion protein provided by the phagmid in order to be infective. Using such helper phage leads preferentially to phage particles that carry more than one copies of the fusion protein on their surface, and thus favors the formation of dimers of the binding protein on the surface of the genetic package.

According to a preferred embodiment of the invention each of the fusion protein monomers are prepared in the context of an oligomer, so that the portion of soluble binding agents is less than 20%, more preferably less than 10%, most preferably less than 1%.

According to the inventive method a genetic package can be prepared preferably displaying at least two fusion proteins. In a specific embodiment each monomer of the inventive oligomer is bound to the outer surface of the genetic package. The invention also provides bivalent phage displaying two fusion proteins from oligomers each containing an oligomer that dimerizes upon expression.

A library of genetic packages is also claimed, which can exemplarily comprise at least 10 variant genetic packages, wherein said variant genetic packages can display heteromers of modular antibody domains. The heteromer can be based on a scaffold comprising a target binding site. According to a specific embodiment of the invention the target binding site and the scaffold binding site can be similar or identical. A scaffold ligand according to the invention can also be a CDR target. For example, the scaffold can be a parent Fab and at least 20%, preferably at least 30%, more preferred at least 40% of the parent Fab variants are binding to the CDR-target of said parent Fab.

The inventive library can also contain variants of the oligomer produced according to the invention having differences in the amino acid sequence.

This can be provided by modifying the amino acid sequences by at least one insertion or substitution to introduce at least one foreign amino acid, and by a deletion. Foreign amino acids can be introduced by a randomization technique. The foreign amino acids can also be selected from a specific group of amino acids to obtain a library enriched with specific amino acids at the randomized positions. When the foreign amino acid is selected from a specific group of amino acids, such as amino acids with specific polarity, or hydrophobicity, a library enriched in the specific group of amino acids at the randomized positions can be obtained according to the invention. Such libraries are also called "focused" libraries.

According to the invention there is further provided a method of selecting a linker for binding a polypeptide to the outer surface of a genetic package, comprising
  a. providing a library of genetic packages containing a variety of linkers to connect a first polypeptide to the genetic package,
  b. determining the member of the library containing a linker that does not significantly interfere with the function of said first polypeptide, and
  c. selecting said linker for connecting a second polypeptide to said genetic package.

Thereby suitable linkers to be used for fusion proteins of the same type can be obtained. By the same type of fusion proteins those are meant that link the same formats of genetic packages and binding agent to each other.

Such a method according to the invention can further be used to prepare enriched libraries containing a preselected group of linker variants that fulfil at least one selection criterion, such as flexibility and sterical accessibility of the binding site to the binding partner. This can be determined by measuring the binding properties of a well-known binding agent in the presence of a variety of linker sequences. The enriched library may thus be further selected for another criterion, such as protease resistance, which is e.g. important for the stability in a medium containing bacterial proteases.

The selected specific linker sequence can then be used to prepare libraries of fusion proteins of the same format, however, with variants of the binding agents, thus enabling the identification, selection and preparation of those agents with the best binding properties in predetermined test systems.

In a preferred embodiment according to the invention such a linker is at least 20 amino acids long, preferably at least 25 amino acid residues, more preferably at least 30 amino acid residues, up to 50 amino acid residues. Especially when amino acids such as Gly, Ser or Ala are involved, which are responsible for the flexibility of a linker, such a linker is advantageously used for the display of a potential binding site, which is close to the surface of the genetic package and which potential binding site may not be able to bind to its partner for sterical reasons.

The linker between the protein to be displayed and the anchor protein of the genetic package (in case of filamentous phage e.g. p3, p8, pX, pIX, pVII) is especially important if the potential binding site of the displayed molecule is in spatial vicinity of the phage particle. In antibody libraries utilizing variable domains and antigen binding sites formed by CDR-loops and display of the library members as amino-terminal fusion to p3 the potential antigen binding site is directed away from the phage particle. Therefore, the linker structure between library members and the phage coat protein is not important. Engineering the bottom loops of immunoglobulin domains and performing phage display may however be an inefficient process and decrease yields of antigen binding clones or even preclude it. Varying the linker between a library member protein and its fusion partner on the surface can solve or may at least reduce this problem.

In order to select for optimal linker sequences (in terms of length and flexibility as well as stability) a library of linkers can be prepared in which the anchor protein at the surface of the genetic replicable package is fused to a known binding protein which is for sterical reasons notoriously difficult to select for.

This library of sequences can be varied in length and amino acid content.

Selection methods of the linker library for optimal linkers depend on the application but basically it should be for selecting all properties one wishes to have in a certain methodology. Enrichment against an antigen that is difficult to select may yield linker sequences which allow library members a good access to the antigen. Incubation in protease solutions or under other harsh conditions or frequent passaging through host cells under proteolytic conditions (e.g. old microbial cultures) may be an appropriate selection for stable display linkers.

A library of linkers may be produced by any well known library technology. Synthetic linker sequence lengths may vary between 10-500 amino acids. Alternatively, linker can be complete proteins known to be of flexible nature.

The invention also provides a method of producing an oligomer of modular antibody domains binding to a target comprising the steps of:
 providing a library of oligomers of modular antibody domains produced according to the inventive method as described
 contacting said library with said target in the presence of a scaffold ligand,
 selecting a library member binding to said target in the presence of a scaffold ligand, and
 manufacturing a preparation of the functional oligomer.

The scaffold ligand can be selected from the group consisting of an effector molecule, FcRn, serum albumin, Protein A, Protein G, Protein L or a CDR target. As an example, the effector molecule can be selected from the group consisting of CD64, CD16, CD32, Fc receptors.

The oligomers can be dimers selected from the group of VH/VL, CH1/CL, CH2/CH2, CH3/CH3, Fc and Fab, or single chains thereof.

The method according to the invention can provide a library containing at least $10^2$ independent clones expressing functional oligomers of modular antibody domains or variants thereof. The library member can then be selected according to the requested binding affinity, preferably it has a target binding affinity of Kd<$10^{-8}$M. According to the invention it is also provided a pool of preselected independent clones, which is e.g. affinity matured, which pool comprises preferably at least 10, more preferably at least 100, more preferably at least 1000, more preferably at least 10000, even more than 100000 independent clones. Those libraries, which contain the preselected pools, are preferred sources to select the high affinity modular antibodies according to the invention.

Preferably the library is a yeast library and the yeast host cell exhibits at the surface of the cell the oligomers with the biological activity. The yeast host cell is preferably selected from the genera *Saccharomyces, Pichia, Hansenula, Schizisaccharomyces, Kluyveromyces, Yarrowia* and *Candida*. Most preferred, the host cell is *Saccharomyces cerevisiae*.

According to a specific embodiment of the invention, the target is a receptor of the erbB class. In this case, by the method of the invention an immunoglobulin can be obtained that binds to a receptor of the erbB class.

The invention further provides a high quality library containing at least $10^6$ independent clones of functional dimers of modular antibody domains or variants thereof, or the pools of optimized or preselected clones, e.g. the affinity matured clones, which pools are containing at least 10 independent clones that are binding to a target and to a scaffold ligand. The target can be a ligand binding to a parent molecule subject to amino acid variation. The parent molecule can be a functional Fc or a functional Fab, or part thereof.

According to a specific embodiment of the invention the parent molecules can be varied by random or site specific mutagenesis.

The library can contain functional dimers of modular antibody domains that are binding to a target and to a scaffold ligand, and at least 20%, preferably at least 30%, more preferred at least 40% of the functional dimers are binding to CD64. This is particularly preferred with a modular antibody that contains CH2 domains, such as an Fc scaffold.

Alternatively, the library can contain functional dimers of modular antibody domains that are binding to a target and to a scaffold ligand, and at least 20%, preferably at least 30%, more preferred at least 40% of the functional dimers are binding to protein A. This is particularly preferred with a modular antibody that contains CH2 and CH3 domains, such as an Fc scaffold.

Alternatively, the library can contain functional dimers of modular antibody domains that are binding to a target and to a scaffold ligand, and at least 20%, preferably at least 30%, more preferred at least 40% of the functional dimers are binding to the same CDR target. This is particularly preferred with modular antibodies containing a variable region, such as an Fab scaffold with specificity to a single CDR target.

FIGURES

FIG. 1:

Schematic presentation of the PCRs used for production of the fragments used for assembly of the library Fcab01. PCR primers are indicated by arrows with their respective 5'-3' orientation, and vertical lines indicate the approximate positions of the introduced restriction sites which were used for assembly of the mutated gene. The restriction sites are contained on the primers for ligations of the PCR fragments.

FIG. 2:

Amino acid sequence and secondary structure of a CH3 domain (IMGT numbering). The randomization scheme is provided for the libraries Fcab01 to Fcab06.

Randomized positions in the AB and EF loop are marked with a circle. X stands for all 20 amino acids (encoded by NNB), z only for Ala, Asp, Ser, Tyr (encoded by KMT; focused library).

DETAILED DESCRIPTION OF THE INVENTION

The oligomers of the modular antibody domains according to the present invention will be useful as stand-alone molecules, as well as fusion proteins or derivatives, most typically fused before or after modification in such a way as to be part of larger structures, e.g. of complete antibody molecules, or parts thereof. Immunoglobulins or fusion proteins as produced according to the invention thus also comprise Fc fragments, Fab fragments, Fv fragments, single domain antibodies, single chain antibodies, in particular single-chain Fv fragments, bi- or multispecific scFv, diabodies, unibodies, multibodies, multivalent or multimers of immunoglobulin domains and others. It will be possible to use the engineered proteins to produce molecules which are monospecific, bispecific, trispecific, and may even carry more specificities. By the invention it is possible to control and preselect the valency of binding at the same time according to the requirements of the planned use of such molecules.

Specific terms as used throughout the specification have the following meaning.

The term "immunoglobulin" as used according to the present invention is defined as polypeptides or proteins that may exhibit mono- or bi- or multi-specific, or mono-, bi- or multivalent binding properties, preferably at least two, more preferred at least three specific binding sites for epitopes of e.g. antigens, effector molecules or proteins either of pathogen origin or of human structure, like self-antigens including cell-associated or serum proteins. The term immunoglobulin as used according to the invention also includes functional fragments of an antibody, such as Fc, Fab, scFv, single chain dimers of CH1/CL domains, Fv, dimers like VH/VL, CH1/CL, CH2/CH2, CH3/CH3, or other derivatives or combinations of the immunoglobulins, like single chains of pairs of immunoglobulin domains. The definition further includes domains of the heavy and light chains of the variable region (such as dAb, Fd, Vl, Vk, Vh, VHH) and the constant region or individual domains of an intact antibody such as CH1, CH2, CH3, CH4, Cl and Ck, as well as mini-domains consisting of at least two beta-strands of an immunoglobulin domain connected by a structural loop.

"Modular antibodies" as used according to the invention are defined as antigen-binding molecules, like human antibodies, composed of at least one polypeptide module or protein domain, preferably in the natural form. The term "modular antibodies" includes antigen-binding molecules that are either immunoglobulins, immunoglobulin-like proteins, or other proteins exhibiting modular formats and antigen-binding properties similar to immunoglobulins or antibodies, which can be used as antigen-binding scaffolds, preferably based on human proteins.

The term "immunoglobulin-like molecule" as used according to the invention refers to any antigen-binding protein, in particular to a human protein, which has a domain structure that can be built in a modular way. Immunoglobulin-like molecules as preferably used for the present invention are T-cell receptors (TCR), fibronectin, transferrin, CTLA-4, single-chain antigen receptors, e.g. those related to T-cell receptors and antibodies, antibody mimetics, adnectins, anticalins, phylomers, repeat proteins such as ankyrin repeats, avimers, Versabodies™, scorpio toxin based molecules, and other non-antibody protein scaffolds with antigen binding properties.

Ankyrin repeat (AR), armadillo repeat (ARM), leucine-rich repeat (LRR) and tetratricopeptide repeat (TPR) proteins are the most prominent members of the protein class of repeat proteins. Repeat proteins are composed of homologous structural units (repeats) that stack to form elongated domains. The binding interaction is usually mediated by several adjacent repeats, leading to large target interaction surfaces.

Avimers contain A-domains as strings of multiple domains in several cell-surface receptors. Domains of this family bind naturally over 100 different known targets, including small molecules, proteins and viruses. Truncation analysis has shown that a target is typically contacted by multiple A-domains with each domain binding independently to a unique epitope. The avidity generated by combining multiple binding domains is a powerful approach to increase affinity and specificity, which these receptors have exploited during evolution.

Anticalins are engineered human proteins derived from the lipocalin scaffold with defined binding properties typical for humanized antibodies. Lipocalins comprise 160-180 amino acids and form conical beta-barrel proteins with a ligand-binding pocket surrounded by four loops. Small hydrophobic compounds are the natural ligands of lipocalins, and different lipocalin variants with new compound specificities (also termed 'anticalins') could be isolated after randomizing residues in this binding pocket.

Single chain or single domain antigen receptors contain a single variable domain and are 20% smaller than camelid single domain antibodies.

Phylomers are peptides derived from biodiverse natural protein fragments.

It is understood that the term "modular antibody", "immunoglobulin", "immunoglobulin-like proteins" includes a derivative thereof as well. A derivative is any combination of one or more modular antibodies of the invention and or a fusion protein in which any domain or minidomain of the modular antibody of the invention may be fused at any position of one or more other proteins (such as other modular antibodies, immunoglobulins, ligands, scaffold proteins, enzymes, toxins and the like). A derivative of the modular antibody of the invention may also be obtained by association or binding to other substances by various chemical techniques such as covalent coupling, electrostatic interaction, di-sulphide bonding etc. The other substances bound to the immunoglobulins may be lipids, carbohydrates, nucleic acids, organic and inorganic molecules or any combination thereof (e.g. PEG, prodrugs or drugs). A derivative would also comprise an antibody with the same amino acid sequence but made completely or partly from non-natural or chemically modified amino acids.

A "structural loop" or "non-CDR-loop" according to the present invention is to be understood in the following manner:

modular antibodies, immunoglobulins or immunoglobulin-like substances are made of domains with a so called immunoglobulin fold. In essence, strands of antiparallel beta sheets are connected by loops to form a compressed antiparallel beta barrel. In the variable region, some of the loops of the domains contribute essentially to the specificity of the antibody, i.e. the binding to an antigen by the natural binding site of an antibody. These loops are called CDR-loops. The CDR loops are located within the CDR loop region, which may in some cases include also the variable framework region (called "VFR") that is adjacent to the CDR loops. It is known that VFRs may contribute to the antigen binding pocket of an antibody, which generally is mainly determined by the CDR loops. Thus, those VFRs are considered as part of the CDR loop region, and would not be appropriately used for engineering new antigen binding sites. Contrary to those VFRs within the CDR loop region or located proximal to the CDR loops, other VFRs of variable domains would be particularly suitable for use according to the invention. Those are the structural loops of the VFRs located opposite to the CDR loop region, or at the C-terminal side of a variable immunoglobulin domain.

The term "antigen" or "target" as used according to the present invention shall in particular include all antigens and target molecules capable of being recognised by a binding site of a modular antibody. Specifically preferred antigens as targeted by the receptor molecule according to the invention are those antigens or molecules, which have already been proven to be or are capable of being immunologically or therapeutically relevant, especially those, for which a clinical efficacy has been tested.

The term "target" or "antigen" as used herein shall comprise molecules selected from the group consisting of allergens, tumor associated antigens, self antigens including cell surface receptors, enzymes, Fc-receptors, FcRn, HSA, IgG, interleukins or cytokines, proteins of the complement system, transport proteins, serum molecules, bacterial antigens, fungal antigens, protozoan antigens and viral antigens, also molecules responsible for transmissible spongiform encephalitis (TSE), such as prions, infective or not, and markers or molecules that relate to inflammatory conditions, such as pro-inflammatory factors, multiple sclerosis or alzheimer disease, or else haptens.

The term "cell surface antigens" shall include all antigens capable of being recognised by an antibody structure on the surface of a cell, and fragments of such molecules. Preferred cell surface antigens are those antigens, which have already been proven to be or which are capable of being immunologically or therapeutically relevant, especially those, for which a preclinical or clinical efficacy has been tested. Those cell surface molecules are specifically relevant for the purpose of the present invention, which mediate cell killing activity. Upon binding of the immunoglobulin according to the invention to preferably at least two of those cell surface molecules the immune system provides for cytolysis or cell death, thus a potent means for attacking human cells may be provided.

The antigen is either recognized as a whole target molecule or as a fragment of such molecule, especially substructures of targets, generally referred to as epitopes.

Substructures of antigens are generally referred to as "epitopes" (e.g. B-cell epitopes, T-cell epitopes), as long as they are immunologically relevant, i.e. are also recognisable by natural or monoclonal antibodies. The term "epitope" as used herein according to the present invention shall mean a molecular structure which may completely make up a specific binding partner or be part of a specific binding partner to a binding site of a modular antibody or an immunoglobulin of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

As used herein, the term "specifically binds" or "specific binding" refers to a binding reaction which is determinative of the cognate ligand of interest in a heterogeneous population of molecules. Thus, under designated conditions (e.g. immunoassay conditions), the modular antibody binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may also be integrated into the host chromosome. Alternatively, an expression system can be used for in vitro transcription/translation. The expression system preferably is employing a host cell that is either a eukaryotic or prokaryotic host cell, preferably a mammalian or yeast host cell, as well as a bacterial host cell.

The preferred expression system for the fusion proteins is a non-suppressor host cell, which would be sensitive to a stop codon, such as an amber stop codon, and would thus stop translation thereafter. In the absence of such a stop codon such non-suppressor host cells, preferably *E. coli*, are preferably used. In the presence of such a stop codon supressor host cells would be used.

All numbering of the amino acid sequences of the immunoglobulins is according to the IMGT numbering scheme (IMGT, the international ImMunoGeneTics, Lefranc et al., 1999, Nucleic Acids Res. 27: 209-212).

For the purposes of this invention, the term "binding agent" or "ligand" refers to a member of a binding pair, in particular binding polypeptides having the potential of serving as a binding domain for a binding partner. Examples of binding partners include pairs of binding agents with functional interactions, such as receptor binding to ligands, antibody binding to antigen or receptors, a drug binding to a target, and enzyme binding to a substrate The term "fusion protein" or "chimeric fusion protein" as used for the purpose of the invention shall mean the molecule composed of a genetic package, at least part of an outer surface structure, such as a coat protein or part thereof, optionally a linker sequence, and a binding agent. The fusion protein is encoded by a vector with the gene of the binding agent and information to display a copy of the binding agent at the surface of the genetic package.

The term "cytotoxic activity" as used for the purpose of the invention shall mean the activity on effector cells resulting in activation of cytotoxic T-cells or on cells, which mediate antibody-dependent cell cytotoxicity (ADCC), complement dependent cytotoxicity (CDC) and/or antibody-dependent cellular phagocytosis (ADCP). Modular antibodies according to the invention thus kill antibody-coated target cells, which they optionally bind with their Fc receptors.

"Scaffold" shall mean a temporary framework either natural or artificial used to support the molecular structure of a polypeptide in the construction of variants or a repertoire of the polypeptide. It is usually a modular system of polypeptide domains that maintains the tertiary structure or the function of the parent molecule. Exemplary scaffolds are modular antibodies, which may be mutagenized to produce variants within said scaffold, to obtain a library.

The term "scaffold ligand" as used for the purpose of the invention shall mean a ligand that binds to a scaffold or the backbone of modular antibodies, thus determining the molecular structure or primary function and specificity of said modular antibody. In preferred cases the scaffold ligand is a functional ligand, mediating a biological function upon binding, like an effector ligand. In an alternative embodiment the scaffold ligand is a functional ligand, which is a specific target bound by the CDR region, non-structural loop region or structural loop region. The same scaffold ligand can bind many variants of a modular antibody regardless of their target specificities. In general, the presence of scaffold ligand binding site indicates that the variant is expressed and folded correctly. Thus, binding of the scaffold ligand to its binding site provides a method for preselecting functional polypeptides from a repertoire of polypeptides. Designing variants of modular antibodies that keep the binding property to a scaffold ligand avoids the preparation of variants that are non-functional, for example as a result of the introduction of mutations, folding mutants or expression mutants which would be or are incapable of binding to substantially any target or effector ligand. Such non-functional mutants sometimes are generated by the normal randomisation and variation procedures employed in the construction of polypeptide repertoires. Providing functional mutants that bind to a scaffold ligand permits the person skilled in the art to prepare a library of modular antibodies which is enriched in functional, well folded and highly expressed library members.

The term "effector ligand" as used for the purpose of the invention shall mean a ligand mediating effector functions, like an effector molecule. Exemplary effector ligands are Fc receptors or Fc receptor-like molecules interfering with immunoglobulins. An Fc receptor is a protein found on the surface of certain cells—including natural killer cells, macrophages, neutrophils, and mast cells—that contribute to the protective functions of the immune system. Its name is derived from its binding specificity for a part of an antibody known as the Fc (Fragment-crystallizable) region. Fc receptors bind to antibodies that are attached to infected cells or invading pathogens. Their activity stimulates phagocytic or cytotoxic cells to destroy microbes, or infected cells by antibody-mediated cellular phagocytosis (ADCP) or antibody-dependent cell-mediated cytotoxicity (ADCC). There are several different types of Fc receptors, which are classified based on the type of antibody that they recognize; those that bind the most common class of antibody, IgG, are called Fc-gamma receptors (FcγR), those that bind IgA are called Fc-alpha receptors (FcαR) and those that bind IgE are called Fc-epsilon receptors (FcεR). Equivalent to an effector ligand and thus incorporated into the definition is any surrogate ligand that recognizes the same or similar binding site within the modular antibody, such as Protein A.

All FcγRs belong to the immunoglobulin superfamily and are the most important Fc receptors for inducing phagocytosis of opsonized (coated) microbes. This family includes several members that differ in their antibody affinities due to their different molecular structure: FcγRI (CD64), FcγRIIA (CD32a), FcγRIIB (CD32b), FcγRIIIA (CD16a), FcγRIIIB (CD16b). For instance, FcγRI binds to IgG more strongly than FcγRII and FcγRIII, and has an extracellular portion composed of three immunoglobulin (Ig)-like domains, one more domain than FcγRII and FcγRIII. These properties allow activation of FcγRI by a sole IgG molecule (or monomer), while the latter two Fcγ receptors must bind multiple IgG molecules within an immune complex to be activated.

Another FcR is expressed on multiple cell types and is similar in structure to MHC class I. This receptor also binds IgG and is involved in preservation of this antibody in order to increase its biological half-life in vivo. However, since this Fc receptor is also involved in transferring IgG from a mother either via the placenta to her fetus or in milk to her suckling infant, it is called the neonatal Fc receptor (FcRn). Recently this receptor has been implicated in being involved in homeostasis of IgG serum levels.

Antibody-Dependent Cell-Mediated Cytotoxicity (ADCC) is a mechanism of cell-mediated immunity whereby an effector cell of the immune system actively lyses a target cell that has been bound by specific antibodies. It is one of the mechanisms through which antibodies, as part of the humoral immune response, can act to limit and contain infection. Classical ADCC is mediated by natural killer (NK) cells; monocytes and eosinophils can also mediate ADCC. For example Eosinophils can kill certain parasitic worms known as helminths through ADCC. ADCC is part of the adaptive immune response due to its dependence on a prior antibody response.

The term "foreign" in the context of amino acids shall mean the newly introduced amino acids being naturally occurring, but foreign to the site of modification, or substitutes of naturally occurring amino acids. "Foreign" with reference to an antigen binding sites means that the antigen binding site is not naturally formed by the specific binding region of the agent, and a foreign binding partner, but not the natural binding partner of the agent, is bound by the newly engineered binding site.

The term "variable binding region" sometimes called "CDR region" as used herein refers to molecules with varying structures capable of binding interactions with antigens. Those molecules can be used as such or integrated within a larger protein, thus forming a specific region of such protein with binding function. The varying structures can be derived from natural repertoires of binding proteins such as immunoglobulins or phylomers or synthetic diversity, including repeat-proteins, avimers and anticalins. The varying structures can as well be produced by randomization techniques, in particular those described herein. These include mutagenized CDR or non-CDR regions, loop regions of immunoglobulin variable domains or constant domains.

Modified binding agents with different modifications at specific sites are referred to as "variants". Variants of a scaffold are preferably grouped to form libraries of binding agents, which can be used for selecting members of the library with predetermined functions. In accordance therewith, a loop region of a binding agent comprising positions within one or more loops potentially contributing to a binding site, is preferably mutated or modified to produce libraries, preferably by random, semi-random or, in particular, by site-directed random mutagenesis methods, in particular to delete, exchange or introduce randomly generated inserts into loops, preferably into structural loops. Alternatively preferred is the use of combinatorial approaches. Any of the known mutagenesis methods may be employed, among them cassette mutagenesis. These methods may be used to make amino acid modifications at desired positions of the immunoglobulin of the present invention. In some cases positions are chosen randomly, e.g. with either any of the possible amino acids or a selection of preferred amino acids to randomize loop sequences, or amino acid changes are made using simplistic rules. For example all residues may be mutated preferably to specific amino acids, such as alanine, referred to as amino acid or alanine scanning. Such methods may be coupled with more sophisticated engineering approaches that employ selection methods to screen higher levels of sequence diversity.

The preferred cytotoxic modular antibody according to the invention with a molecular weight of less than 60 kD or up to 60 kD has a small size as compared to full length antibodies. The preferred size is up to 55 kD. Modular antibody single domains usually have a molecular size of 10-15 kD, thus a molecule based on 4 modular antibody domains would have a molecular size of 40-60 kD, depending on the glycosylation or any additional conjugation of pharmacologically active substances, like toxins or peptides.

The preferred format is an oligomer, composed of modular antibody domains, preferably up to 4 domains, more preferred 3 domains, and even more preferred made up of 2 domains. Formats based on the combination of 5 modular antibody domains or more are commonly thought not to exert the specific advantages of small sized antibody fragments, which are e.g. ease of expression in various expression systems and tissue penetration.

It is feasible to provide the preferred modular antibody of the invention as a single domain antibody. However, antibody domains tend to dimerize upon expression, either as a homodimer, like an Fc, or a heterodimer, like an Fab. The dimeric structure is thus considered as a basis for the preferred stable molecule. The preferred dimers of immunoglobulin domains are selected from the group consisting of single domain dimers, like VH/VL, CH1/CL (kappa or lambda), CH2/CH2 and CH3/CH3. Dimers or oligomers of modular antibody domains can also be provided as single chain or two chain molecules, in particular those linking the C-terminus of one domain to the N-terminus of another.

Binding partners are agents that specifically bind to one another, usually through non-covalent interactions. Examples of binding partners include pairs of binding agents with functional interactions, such as receptor binding to ligands, antibody binding to antigen, a drug binding to a target, and enzyme binding to a substrate. Binding partners have found use in many therapeutic, diagnostic, analytical and industrial applications. Most prominent binding partners, also called binding pairs, are antibodies or immunoglobulins, fragments or derivatives thereof. In most cases the binding of such binding agents is required to mediate a biological effect or a function, a "functional interaction".

According to a specific embodiment of the present invention the binding agent is an immunoglobulin of human or murine origin, and may be employed for various purposes, in particular in pharmaceutical compositions. Of course, the modified immunoglobulin may also be a humanized or chimeric immunoglobulin.

The binding agent which is a human immunoglobulin is preferably selected or derived from the group consisting of IgA1, IgA2, IgD, IgE, IgG1, IgG2, IgG3, IgG4 and IgM. The murine immunoglobulin binding agent is preferably selected or derived from the group consisting of IgA, IgD, IgE, IgG1, IgG2A, IgG2B, IgG2C, IgG3 and IgM.

Such a binding agent comprises preferably a heavy and/or light chain or a part thereof. A modified immunoglobulin according to the invention may comprise a heavy and/or light chain, at least one variable and/or constant domain, or a part thereof including a minidomain.

A constant domain is an immunoglobulin fold unit of the constant part of an immunoglobulin molecule, also referred to as a domain of the constant region (e.g. CH1, CH2, CH3, CH4, Ck, Cl).

A variable domain is an immunoglobulin fold unit of the variable part of an immunoglobulin, also referred to as a domain of the variable region (e.g. Vh, Vk, Vl, Vd)

An exemplary modular antibody according to the invention consists of a constant domain selected from the group consisting of CH1, CH2, CH3, CH4, Igk-C, Igl-C, combinations, derivatives or a part thereof including a mini-domain, with at least one loop region, and is characterised in that said at least one loop region comprises at least one amino acid modification forming at least one modified loop region, wherein said at least one modified loop region binds specifically to at least one epitope of an antigen.

Another modular antibody according to the invention can consist of a variable domain of a heavy or light chain, combinations, derivatives or a part thereof including a minidomain, with at least one loop region, and is characterised in that said at least one loop region comprises at least one amino acid modification forming at least one modified loop region, wherein said at least one modified loop region binds specifically to at least one epitope of an antigen.

The modular antibody according to the present invention may comprise one or more domains (e.g. at least two, three, four, five, six, ten domains). If more than one domain is present in the modular antibody these domains may be of the same type or of varying types (e.g. CH1-CH1-CH2, CH3-CH3, $(CH2)_2$—$(CH3)_2$, with or without the hinge region). Of course also the order of the single domains may be of any kind (e.g. CH1-CH3-CH2, CH4-CH1-CH3-CH2).

The invention preferably refers to parts of antibodies, such as IgG, IgA, IgM, IgD, IgE and the like. The modular antibodies of the invention may also be a functional antibody fragment such as Fab, $Fab_2$, scFv, Fv, Fc, Fcab™, an antigen-binding Fc, or parts thereof, or other derivatives or combinations of the immunoglobulins such as minibodies, domains of the heavy and light chains of the variable region (such as dAb, Fd (binding site made up of one or more single domains), VL, including Vlambda (Vl) and Vkappa (Vk), VH, VHH) as well as mini-domains consisting of two beta-strands of an immunoglobulin domain connected by at least two structural loops, as isolated domains or in the context of naturally associated molecules. A particular embodiment of the present invention refers to the Fc fragment of an antibody molecule, either as antigen-binding Fc fragment (Fcab™) through modifications of the amino acid sequence or as conjugates or fusions to receptors, peptides or other antigen-binding modules, such as scFv.

The modular antibodies can be used as isolated polypeptides or as combination molecules, e.g. through recombination, fusion or conjugation techniques, with other peptides or polypeptides. The peptides are preferably homologous to immunoglobulin domain sequences, and are preferably at least 5 amino acids long, more preferably at least 10 or even at least 50 or 100 amino acids long, and constitute at least partially the loop region of the immunoglobulin domain. The preferred binding characteristics relate to predefined epitope binding, affinity and avidity.

The modular antibody according to the invention is possibly further combined with one or more modified modular antibodies or with unmodified modular antibodies, or parts thereof, to obtain a combination modular antibody. Combinations are preferably obtained by recombination techniques, but also by binding through adsorption, electrostatic interactions or the like, or else through conjugation or chemical binding with or without a linker. The preferred linker sequence is either a natural linker sequence or a functionally suitable artificial sequence.

In general the modular antibody according to the invention may be used as a building block to molecularly combine other modular antibodies or biologically active substances or molecules. It is preferred to molecularly combine at least one antibody binding to the specific partner via the variable or non-variable sequences, like structural loops, with at least one other binding molecule which can be an antibody, antibody fragment, a soluble receptor, a ligand or another antibody domain, or a binding moiety thereof. Other combinations refer to proteinaceous molecules, nucleic acids, lipids, organic molecules and carbohydrates.

The engineered molecules according to the present invention will be useful as stand-alone proteins as well as fusion proteins or derivatives, most typically fused in such a way as to be part of larger antibody structures or complete antibody molecules, or parts or fragments thereof, such as Fab fragments, Fc fragments, Fv fragments and others. It will be possible to use the engineered proteins to produce molecules which are monospecific, bispecific, trispecific, and maybe even carry more specificities at the same time, and it will be possible at the same time to control and preselect the valency of binding at the same time according to the requirements of the planned use of such molecules.

According to the present invention, the modular antibody optionally exerts one or more binding regions to antigens, including the binding site binding specifically to the cell surface target and the binding sites mediating effector function. Antigen binding sites to one or more antigens may be presented by the CDR-region or any other natural receptor binding structure, or be introduced into a structural loop region of an antibody domain, either of a variable or constant domain structure. The antigens as used for testing the binding properties of the binding sites may be naturally occurring molecules or chemically synthesized molecules or recombinant molecules, either in solution or in suspension, e.g. located on or in particles such as solid phases, on or in cells or on viral surfaces. It is preferred that the binding of an immunoglobulin to an antigen is determined when the antigen is still adhered or bound to molecules and structures in the natural context. Thereby it is possible to identify and obtain those modified immunoglobulins that are best suitable for the purpose of diagnostic or therapeutic use.

Modular antibody or immunoglobulin domains may be modified according to the present invention (as used herein the terms immunoglobulin and antibody are interchangeable) which modifications are preferably effected in immunoglobulin domains or parts thereof that contain a loop, either a CDR-loop or a non-CDR loop, structural loops being the preferred sites of modifications or mutagenesis. In some cases it is preferable to use a defined modified structural loop or a structural loop region, or parts thereof, as isolated molecules for binding or combination purposes.

It is particularly preferred that the modular antibody according to the invention is binding to said cell surface target through at least part of a structural loop and/or CDR loop.

In an alternate embodiment it is preferred that the modular antibody according to the invention is binding to said effector ligand, or a surrogate ligand for such an effector ligand, like protein A, through at least part of a structural loop and/or CDR loop, thus mediating the effector function.

In a preferred embodiment the binding agent is binding with its native or modified binding structure or newly formed binding site, specifically to at least two such epitopes that are identical or differ from each other, either of the same antigen or of different antigens.

In a preferred domain structure of a binding agent it is preferred to modify at least one loop region resulting in a substitution, deletion and/or insertion of one or more nucleotides or amino acids, preferably a point mutation, or even the exchange of whole loops, more preferred the change of at least 2, 3, 4, 5, 6, 7, 8, 9, 10, 11, 12, 13, 14 or 15, up to 30 amino acids. Thereby the modified sequence comprises amino acids not included in the conserved regions of the loops, the newly introduced amino acids being naturally occurring, but foreign to the site of modification, or substitutes of naturally occurring amino acids.

However, the maximum number of amino acids inserted into a loop region of a binding agent preferably may not exceed the number of 30, preferably 25, more preferably 20 amino acids at a maximum. The substitution and the insertion of the amino acids occurs preferably randomly or semi-randomly using all possible amino acids or a selection of preferred amino acids for randomization purposes, by methods known in the art and as disclosed in the present patent application.

The site of modification may be at a specific single loop or a loop region, in particular a structural loop or a structural loop region. A loop region usually is composed of at least one, preferably at least two, preferably at least 3 or at least 4 loops that are at the tip or the bottom of a domain, in proximity or adjacent to each other, and which may contribute to the binding of an antigen through forming an antigen binding site or antigen binding pocket. It is preferred that the one or more sites of modification are located within the area of 10 amino acids, more preferably within 20, 30, 40, 50, 60, 70, 80, 90 up to 100 amino acids, in particular within a structural region to form a surface or pocket where the antigen can sterically access the loop regions.

In this regard the preferred modifications are engineered in the loop regions of CH1, CH2, CH3 and CH4, in particular in the range of amino acids 7 to 21, amino acids 25 to 39, amino acids 41 to 81, amino acids 83 to 85, amino acids 89 to 103 and amino acids 106 to 117.

In another preferred embodiment a modification in the structural loop region comprising amino acids 92 to 98 is combined with a modification in the structural loop region comprising amino acids 8 to 20.

The above identified amino acid regions of the respective immunoglobulins comprise loop regions to be modified. Preferably, a modification in the structural loop region comprising amino acids 92 to 98 is combined with a modification in one or more of the other structural loops.

In a preferred embodiment a modification in the structural loop region comprising amino acids 92 to 98 is combined with a modification in the structural loop region comprising amino acids 41 to 45.2.

Most preferably each of the structural loops comprising amino acids 92 to 98, amino acids 41 to 45.2 and amino acids 8 to 20 contain at least one amino acid modification.

In another preferred embodiment each of the structural loops comprising amino acids 92 to 98, amino acids 41 to 45.2, and amino acids 8 to 20 contain at least one amino acid modification.

According to another preferred embodiment the amino acid residues in the area of positions 15 to 17, 29 to 34, 41 to 45.2, 84 to 85, 92 to 100, and/or 108 to 115 of CH3 are modified.

The preferred modifications of Igk-C and Igl-C of human origin are engineered in the loop regions in the area of amino acids 8 to 20, amino acids 26 to 36, amino acids 41 to 82, amino acids 83 to 88, amino acids 92 to 100, amino acids 107 to 124 and amino acids 123 to 126.

The preferred modifications of loop regions of Igk-C and Igl-C of murine origin are engineered at sites in the area of amino acids 8 to 20, amino acids 26 to 36, amino acids 43 to 79, amino acids 83 to 85, amino acids 90 to 101, amino acids 108 to 116 and amino acids 122 to 126.

Another preferred immunoglobulin preferably used as a therapeutic according to the invention consists of a variable domain of a heavy or light chain, or a part thereof including a minidomain, with at least one loop region, preferably a structural loop region, and is characterised in that said at least one loop region comprises at least one amino acid modification forming at least one modified loop region, wherein said at least one modified loop region forms a relevant binding site as described above.

According to a specific embodiment the immunoglobulin preferably used according to the invention may contain a modification within the variable domain, which is selected from the group of VH, Vkappa, Vlambda, VHH and combinations thereof. More specifically, they comprise at least one modification within amino acids 7 to 22, amino acids 39 to 55, amino acids 66 to 79, amino acids 77 to 89 or amino acids 89 to 104, where the numbering of the amino acid position of the domains is that of the IMGT.

In a specific embodiment, the immunoglobulin preferably used according to the invention is characterised in that the loop regions of VH or Vkappa or Vlambda of human origin comprise at least one modification within amino acids 7 to 22, amino acids 43 to 51, amino acids 67 to 77, amino acids 77 to 88, and amino acids 89 to 104, most preferably amino acid positions 12 to 17, amino acid positions 45 to 50, amino acid positions 68 to 77, amino acids 79 to 88, and amino acid positions 92 to 99, where the numbering of the amino acid position of the domains is that of the IMGT.

The structural loop regions of the variable domain of the immunoglobulin of human origin, as possible selected for modification purposes are preferably located in the area of amino acids 8 to 20, amino acids 44 to 50, amino acids 67 to 76, amino acids 78 to 87, and amino acids 89 to 101.

According to a preferred embodiment the structural loop regions of the variable domain of the immunoglobulin of murine origin as possible selected for modification purposes are preferably located in the area of amino acids 6 to 20, amino acids 43 to 52, amino acids 67 to 79, amino acids 79 to 87, and amino acids 91 to 100.

The immunoglobulin preferably used as a therapeutic according to the invention may also be of camelid origin. Camel antibodies comprise only one heavy chain and have the same antigen affinity as normal antibodies consisting of light and heavy chains. Consequently camel antibodies are much smaller than, e.g., human antibodies, which allows them to penetrate dense tissues to reach the antigen, where larger proteins cannot. Moreover, the comparative simplicity, high affinity and specificity and the potential to reach and interact with active sites, camel's heavy chain antibodies present advantages over common antibodies in the design, production and application of clinically valuable compounds.

According to another preferred embodiment of the present invention the structural loop regions of a modular antibody or an immunoglobulins of camelid origin are modified, e.g. within a VHH, in the region of amino acids 7 to 19, amino acids 43 to 55, amino acids 68 to 76, amino acids 80 to 87 and amino acids 91 to 101.

The preferred method of producing the modular antibody according to the invention refers to engineering a modular antibody that is binding specifically to at least one first epitope and comprising modifications in each of at least two structural loop regions, and determining the specific binding of said at least two loop regions to at least one second epitope, wherein the unmodified structural loop region (non-CDR region) does not specifically bind to said at least one second epitope. Thus, an antibody or antigen-binding structure specific for a first antigen may be improved by adding another valency or specificity against a second antigen, which specificity may be identical, either targeting different epitopes or the same epitope, to increase valency or to obtain bi-, oligo- or multispecific molecules.

On the other hand it is preferred to make use of those modular antibodies that contain native structures interacting with effector molecules or immune cells. Those native structures either remain unchanged or are modulated for an increased effector function. Binding sites for e.g. Fc receptors are described to be located in a CH2 and/or CH3 domain region, and may be mutagenized by well known techniques.

ADCC, antibody-dependent cell-mediated cytotoxicity is the killing of antibody-coated target cells by cells with Fc receptors that recognize the constant region of the bound antibody. Most ADCC is mediated by NK cells that have the Fc receptor FcgammaRIII or CD16 on their surface. Typical assays employ target cells, like Ramos cells, incubated with serially diluted antibody prior to the addition of freshly isolated effector cells. The ADCC assay is then further incubated for several hours and % cytotoxicity detected. Usually the Target:Effector ratio is about 1:16, but may be 1:1 up to 1:50.

Complement-dependent cytotoxicity (CDC) is a mechanism of killing cells in which antibody bound to the target cell surface fixes complement, which results in assembly of the membrane attack complex that punches holes in the target cell membrane resulting in subsequent cell lysis. The commonly used CDC assay follows the same procedure as for ADCC determination, however, with complement containing serum instead of effector cells.

The cytotoxic activity as determined by either of ADCC and CDC assay is proven for a modular antibody according to the invention, if there is a significant increase in the percentage of cytolysis as compared to a control. The absolute percentage increase preferably is higher than 5%, more preferably higher than 10%, even more preferred higher than 20%.

The antibody-dependent cellular phagocytosis, ADCP sometimes called ADPC, is usually investigated side by side with cytolysis of cultured human cells. Phagocytosis by phagocytes, usually human monocytes or monocyte-derived macrophages, as mediated by an antibody can be determined as follows. Purified monocytes may be cultured with cytokines to enhance expression of FcγRs or to induce differentiation into macrophages. ADCP and ADCC assays are then performed with target cells. Phagocytosis is determined as the percentage of positive cells measured by flow cytometry. The positive ADCP activity is proven with a significant uptake of the antibody-antigen complex by the phagocytes. The absolute percentage preferably is higher than 5%, more preferably higher than 10%, even more preferred higher than 20%.

In a typical assay PBMC or monoycytes or monocyte derived macrophages are resuspended in RF2 medium (RPMI 1640 supplemented with 2% FCS) in 96-well plates at a concentration of $1 \times 10^5$ viable cells in 100 ml/well. Appropriate target cells, expressing the target antigen, e.g. Her2/neu antigen and SKBR3 cells, are stained with PKH2 green fluorescence dye. Subsequently $1 \times 10^4$ PKH2-labeled target cells and an Her 2 specific (IgG1) antibody (or modular antibody) or mouse IgG1 isotype control (or modular antibody control) are added to the well of PBMC's in different concentrations (e.g. 1-100 µg/ml) and incubated in a final volume of 200 ml at 37° C. for 24 h. Following the incubation, PBMCs or monoycytes or monocyte derived macrophages and target cells are harvested with EDTA-PBS and transferred to 96-well V-bottomed plates. The plates are centrifuged and the supernatant is aspirated. Cells are counterstained with a 100-ml mixture of RPE-conjugated anti-CD11b, anti-CD14, and human IgG, mixed and incubated for 60 min on ice. The cells are washed and fixed with 2% formaldehyde-PBS. Two-color flow cytometric analysis is performed with e.g. a FACS Calibur under optimal gating. PKH2-labeled target cells (green) are detected in the FL-1 channel (emission wavelength, 530 nm) and RPE-labeled PBMC or monoycytes or monocyte derived macrophages (red) are detected in the FL-2 channel (emission wavelength, 575 nm). Residual target cells are defined as cells that are PKH2$^+$/RPE$^-$ Dual-labeled cells (PKH2$^+$/RPE$^-$) are considered to represent phagocytosis of targets by PBMC or monoycytes or monocyte derived macrophages. Phagocytosis of target cells is calculated with the following equation: percent phagocytosis=100×[(percent dual positive)/(percent dual positive+percent residual targets)]. All tests are usually performed in duplicate or triplicate and the results are expressed as mean 6 SD.

The effector function of the modular antibody according to the invention usually differs from any synthetic cytotoxic activity, e.g. through a toxin that may be conjugated to an immunoglobulin structure. Toxins usually do not activate effector molecules and the biological defence mechanism. Thus, the preferred cytotoxic activity of the modular antibodies according to the invention is a biological cytotoxic activity, which usually is immunostimulatory, leading to effective cytolysis.

The modular antibody according to the invention may specifically bind to any kind of binding molecules or structures, in particular to antigens, proteinaceous molecules, proteins, peptides, polypeptides, nucleic acids, glycans, carbohydrates, lipids, organic molecules, in particular small organic molecules, anorganic molecules, or combinations or fusions thereof, including PEG, prodrugs or drugs. The preferred modular antibody according to the invention may comprise at least two loops or loop regions whereby each of the loops or loop regions may specifically bind to different molecules or epitopes.

Preferably the target antigen is selected from cell surface antigens, including receptors, in particular from the group consisting of erbB receptor tyrosine kinases (such as EGFR, HER2, HER3 and HER4, in particular those epitopes of the extracellular domains of such receptors, e.g. the 4D5 epitope), molecules of the TNF-receptor superfamily, such as Apo-1 receptor, TNFR1, TNFR2, nerve growth factor receptor NGFR, CD40, T-cell surface molecules, T-cell receptors, T-cell antigen OX40, TACI-receptor, BCMA, Apo-3, DR4, DR5, DR6, decoy receptors, such as DcR1, DcR2, CAR1, HVEM, GITR, ZTNFR-5, NTR-1, TNFL1 but not limited to these molecules, B-cell surface antigens, such as CD10, CD19, CD20, CD21, CD22, antigens or markers of solid tumors or hematologic cancer cells, cells of lymphoma or leukaemia, other blood cells including blood platelets, but not limited to these molecules.

According to a further preferred embodiment the target antigen is selected from those antigens presented by cells, like epithelial cells, cells of solid tumors, infected cells, blood cells, antigen-presenting cells and mononuclear cells. Those target antigens expressed or overexpressed by cells are preferably targeted, which are selected from the group consisting of tumor associated antigens, in particular EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, allergy related molecules IgE, cKIT and Fc-epsilon-receptorI, IRp60, IL-5 receptor, CCR3, red blood cell receptor (CR1), human serum albumin, mouse serum albumin, rat serum albumin, Fc receptors, like neonatal Fc-gamma-receptor FcRn, Fc-gamma-receptors Fc-gamma RI, Fc-gamma-RII, Fc-gamma RIII, Fc-alpha-receptors, Fc-epsilon-receptors, fluorescein, lysozyme, toll-like receptor 9, erythropoietin, CD2, CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD64, CD80, CD147, GD3, IL-1, IL-1R, IL-2, IL-2, IL-4, IL-5, IL-6, IL-6, IL-8, IL-12, IL-15, IL-17, IL-18, IL-23, LIF, OSM, interferon alpha, interferon beta, interferon gamma; TNF-alpha, TNF-beta2, TNFalpha, TNFalphabeta, TNF-R1, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TALI, BAFF-R, EPO; LFA-3, ICAM-1, ICAM-3, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, GM-CSF, M-CSF, RANKL, VLA-1, VLA-4, L-selectin, anti-Id, E-selectin, HLA, HLA-DR, CTLA-4, T cell receptor, B7-1, B7-2, VNRintegrin, TGFbeta1, TGF-beta2, eotaxin1, BLyS (B-lymphocyte Stimulator), complement C5, IgE, IgA, IgD, IgM, IgG, factor VII, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrates such as blood group antigens and related carbohydrates, Galili-Glycosylation, Gastrin, Gastrin receptors, tumor associated carbohydrates, Hapten NP-cap or NIP-cap, T cell receptor alpha/beta, E-selectin, P-glycoprotein, MRP3, MRP5, glutathione-S-transferase pi (multi drug resistance proteins), alpha-granule membrane protein (GMP) 140, digoxin, placental alkaline phosphatase (PLAP) and testicular PLAP-like alkaline phosphatase, transferrin receptor, Heparanase I, human cardiac myosin, Glycoprotein IIb/IIIa (GPIIb/IIIa), human cytomegalovirus (HCMV) gH envelope glycoprotein, HIV gp120, HCMV, respiratory syncital virus RSV F, RSVF Fgp, VNRintegrin, Hep B gp120, CMV, gpI- IbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof.

Preferred modular antibodies according to the invention are binding said target antigen with a high affinity, in particular with a high on and/or a low off rate, or a high avidity of binding. Usually a binder is considered a high affinity binder with a Kd of $<10^{-9}$ M. Medium affinity binders with a Kd of less than $10^{-6}$ up to $10^{-9}$ M may be provided according to the invention as well, preferably in conjunction with an affinity maturation process.

Affinity maturation is the process by which antibodies with increased affinity for antigen are produced. With structural changes of an antibody, including amino acid mutagenesis or as a consequence of somatic mutation in immunoglobulin gene segments, variants of a binding site to an antigen are produced and selected for greater affinities. Affinity matured modular antibodies may exhibit a several logfold greater affinity than a parent antibody. Single parent antibodies may be subject to affinity maturation. Alternatively pools of modular antibodies with similar binding affinity to the target antigen may be considered as parent structures that are varied to obtain affinity matured single antibodies or affinity matured pools of such antibodies.

The preferred affinity matured variant of a modular antibody according to the invention exhibits at least a 10 fold increase in affinity of binding, preferably at least a 100 fold increase. The affinity maturation may be employed in the course of the selection campaigns employing respective libraries of parent molecules, either with modular antibodies having medium binding affinity to obtain the modular antibody of the invention having the specific target binding property of a $Kd<10^{-8}$ M and/or a potency of $IC50<10^{-8}$ M. Alternatively, the binding potency or affinity may be even more increased by affinity maturation of the modular antibody according to the invention to obtain the high values corresponding to a Kd or IC50 of less than $10^{-9}$ M, preferably less than $10^{-10}$ M or even less than $10^{-11}$ M, most preferred in the picomolar range.

The IC50, also called 50% saturation concentration, is a measure for the binding potency of a modular antibody. It is the molar concentration of a binder, which produces 50% of the maximum possible binding at equilibrium or under saturation. The potency of an antagonist is usually defined by its IC50 value. This can be calculated for a given antagonist by determining the concentration of antagonist needed to elicit half saturation of the maximum binding of an agonist. Elucidating an IC50 value is useful for comparing the potency of antibodies or antibody variants with similar efficacies; however the dose-response curves produced by both drug antagonists must be similar. The lower the IC50, the greater the potency of the antagonist, and the lower the concentration of drug that is required to inhibit the maximum biological response, like effector function or cytotoxic activity. Lower concentrations of drugs may also be associated with fewer side effects.

Usually the affinity of an antibody correlates well with the IC50. The affinity of an antagonist for its binding site ($K_i$), is understood as its ability to bind to a receptor, which determines the duration of binding and respective agonist activity. Measures to increase the affinity by affinity maturation usually also increase the potency of binding, resulting in the respective reduction of IC50 values in the same range of the Kd values.

The IC50 and Kd values may be determined using the saturation binding assays well-known in the art.

The modular antibody according to the invention is preferably conjugated to a label or reporter molecule, selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Modified immunoglobulins conjugated to labels or reporter molecules may be used, for instance, in assay systems or diagnostic methods.

The modular antibody according to the invention may be conjugated to other molecules which allow the simple detection of said conjugate in, for instance, binding assays (e.g. ELISA) and binding studies.

In a preferred embodiment, antibody variants are screened using one or more cell-based or in vivo assays. For such assays, purified or unpurified modified immunoglobulins are typically added exogenously such that cells are exposed to individual immunoglobulins or pools of immunoglobulins belonging to a library. These assays are typically, but not always, based on the function of the immunoglobulin; that is, the ability of the antibody to bind to its target and mediate some biochemical event, for example effector function, ligand/receptor binding inhibition, apoptosis, and the like. Such assays often involve monitoring the response of cells to the antibody, for example cell survival, cell death, change in cellular morphology, or transcriptional activation such as cellular expression of a natural gene or reporter gene. For example, such assays may measure the ability of antibody variants to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Modular antibodies may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

In a preferred embodiment, the DELFIART EuTDA-based cytotoxicity assay (Perkin Elmer, Mass.) may be used.

Alternatively, dead or damaged target cells may be monitored by measuring the release of one or more natural intracellular components, for example lactate dehydrogenase.

Transcriptional activation may also serve as a method for assaying function in cell-based assays. In this case, response may be monitored by assaying for natural genes or immunoglobulins which may be upregulated, for example the release of certain interleukins may be measured, or alternatively readout may be via a reporter construct. Cell-based assays may also involve the measure of morphological changes of cells as a response to the presence of modular antibodies. Cell types for such assays may be prokaryotic or eukaryotic, and a variety of cell lines that are known in the art may be employed. Alternatively, cell-based screens are performed using cells that have been transformed or transfected with nucleic acids encoding the variants. That is, antibody variants are not added exogenously to the cells. For example, in one embodiment, the cell-based screen utilizes cell surface display. A fusion partner can be employed that enables display of modified immunoglobulins on the surface of cells (Wittrup, 2001, Curr Opin Biotechnol, 12:395-399).

In a preferred embodiment, the immunogenicity of the modular antibodies may be determined experimentally using one or more cell-based assays. In a preferred embodiment, ex vivo T-cell activation assays are used to experimentally quantitate immunogenicity. In this method, antigen presenting cells and naive T cells from matched donors are challenged with a peptide or whole antibody of interest one or more times. Then, T cell activation can be detected using a number of methods, for example by monitoring production of cytokines or measuring uptake of tritiated thymidine. In the most preferred embodiment, interferon gamma production is monitored using Elispot assays.

The biological properties of the modular antibody according to the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic with the appropriate half-life, effector function, apoptotic activity, cytotoxic or cytolytic activity. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the modular antibody according to the invention. Tests of the substances in humans are ultimately required for approval as drugs, and thus of course these experiments are contemplated. Thus the modular antibodies of the present invention may be tested in humans to determine their therapeutic efficacy, toxicity, immunogenicity, pharmacokinetics, and/or other clinical properties. Especially those modular antibodies according to the invention that bind to single cell or a cellular complex through at least two binding motifs, preferably binding of at least three structures cross-linking target cells, would be considered effective in effector activity or preapoptotic or apoptotic activity upon cell targeting and cross-linking. Multivalent binding provides a relatively large association of binding partners, also called cross-linking, which is a prerequisite for apoptosis and cell death.

The modular antibody of the present invention may find use in a wide range of antibody products. In one embodiment the modular antibody of the present invention is used for therapy or prophylaxis, e.g. as an active or passive immunotherapy, for preparative, industrial or analytic use, as a diagnostic, an industrial compound or a research reagent, preferably a therapeutic. The modular antibody may find use in an antibody composition that is monoclonal or polyclonal. In a preferred embodiment, the modular antibodies of the present invention are used to capture or kill target cells that bear the target antigen, for example cancer cells. In an alternate embodiment, the modular antibodies of the present invention are used to block, antagonize, or agonize the target antigen, for example by antagonizing a cytokine or cytokine receptor.

In an alternately preferred embodiment, the modular antibodies of the present invention are used to block, antagonize, or agonize growth factors or growth factor receptors and thereby mediate killing the target cells that bear or need the target antigen.

In an alternately preferred embodiment, the modular antibodies of the present invention are used to block, antagonize, or agonize enzymes and substrate of enzymes.

In a preferred embodiment, a modular antibody is administered to a patient to treat a specific disorder. A "patient" for the purposes of the present invention includes both humans and other animals, preferably mammals and most preferably humans. By "specific disorder" herein is meant a disorder that may be ameliorated by the administration of a pharmaceutical composition comprising a modified immunoglobulin of the present invention.

In one embodiment, a modular antibody according to the present invention is the only therapeutically active agent administered to a patient. Alternatively, the modular antibody according the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The modular antibody may be administered concomitantly with one or more other therapeutic regimens. For example, a modular antibody of the present invention may be administered to the patient along with chemotherapy, radiation therapy, or both chemotherapy and radiation therapy. In one embodiment, the modular antibody of the present invention may be administered in conjunction with one or more antibodies, which may or may not comprise a modular antibody of the present invention. In accordance with another embodiment of the invention, the modular antibody of the present invention and one or more other anti-cancer therapies is employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the modular antibody of the present invention. In one embodiment, the modular antibody is administered with an anti-angiogenic agent, which is a compound that blocks, or interferes to some degree, the development of blood vessels. The anti-angiogenic factor may, for instance, be a small molecule or a protein, for example an antibody, Fc fusion molecule, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the modular antibody is administered with a therapeutic agent that induces or enhances adaptive immune response, for example an antibody that targets CTLA-4. In an alternate embodiment, the modified immunoglobulin is administered with a tyrosine kinase inhibitor, which is a molecule that inhibits to some extent tyrosine kinase activity of a tyrosine kinase. In an alternate embodiment, the modular antibody of the present invention are administered with a cytokine. By "cytokine" as used herein is meant a generic term for proteins released by one cell population that act on another cell as intercellular mediators including chemokines.

Pharmaceutical compositions are contemplated wherein modular antibodies of the present invention and one or more therapeutically active agents are formulated. Stable formulations of the modular antibodies of the present invention are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are preferably sterile. This is readily accomplished by filtration through sterile filtration membranes or other methods. The modular antibody and other therapeutically active agents disclosed herein may also be formulated as immunoliposomes, and/or entrapped in microcapsules.

Administration of the pharmaceutical composition comprising a modular antibody of the present invention, preferably in the form of a sterile aqueous solution, may be done in a variety of ways, including, but not limited to, orally, subcutaneously, intravenously, intranasally, intraotically, transdermally, mucosal, topically (e.g., gels, salves, lotions, creams, etc.), intraperitoneally, intramuscularly, intrapulmonary (e.g., AERx™ inhalable technology commercially available from Aradigm, or Inhance™ pulmonary delivery system commercially available from Inhale Therapeutics), vaginally, parenterally, rectally, or intraocularly.

A preferred method according to the invention refers to a randomly modified nucleic acid molecule coding for an immunoglobulin, immunoglobulin domain or a part thereof which comprises at least one nucleotide repeating unit within a structural loop coding region having the sequence 5'-NNS-3', 5'-NNN-3',5'-NNB-3' or 5'-NNK-3'. In some embodiments the modified nucleic acid comprises nucleotide codons selected from the group of TMT, WMT, BMT, RMC, RMG, MRT, SRC, KMT, RST, YMT, MKC, RSA, RRC, NNK, NNN, NNS or any combination thereof (the coding is according to IUPAC).

The modification of the nucleic acid molecule may be performed by introducing synthetic oligonucleotides into a larger segment of nucleic acid or by de novo synthesis of a complete nucleic acid molecule. Synthesis of nucleic acid may be performed with tri-nucleotide building blocks which would reduce the number of nonsense sequence combinations if a subset of amino acids is to be encoded (e.g. Yanez et al. Nucleic Acids Res. (2004) 32:e158; Virnekas et al. Nucleic Acids Res. (1994) 22:5600-5607).

The randomly modified nucleic acid molecule may comprise the above identified repeating units, which code for all known naturally occurring amino acids or a subset thereof. Those libraries that contain modified sequences wherein a specific subset of amino acids are used for modification purposes are called "focused" libraries. The members of such libraries have an increased probability of an amino acid of such a subset at the modified position, which is at least two times higher than usual, preferably at least 3 times or even at least 4 times higher. Such libraries have also a limited or lower number of library members, so that the number of actual library members reaches the number of theoretical library members. In some cases the number of library members of a focused library is not less than $10^3$ times the theoretical number, preferably not less than $10^2$ times, most preferably not less than 10 times.

Usually libraries according to the invention comprise at least 10 fusion proteins or potential binding agents or variants of scaffold proteins, preferably at least 100, more preferred at least 1000, more preferred at least $10^4$, more preferred at least $10^5$, more preferred at least $10^6$, more preferred at least $10^7$, more preferred at least $10^8$, more preferred at least $10^9$, more preferred at least $10^{10}$, more preferred at least $10^{11}$, up to $10^{12}$, in cases of in vitro display methods, such as ribosomal display, even higher number are feasible.

Various alternatives are available for the manufacture of the gene encoding the randomized library. It is possible to produce the DNA by a completely synthetic approach, in which the sequence is divided into overlapping fragments which are subsequently prepared as synthetic oligonucleotides. These oligonucleotides are mixed together, and annealed to each other by first heating to ca. 100° C. and then slowly cooling down to ambient temperature. After this annealing step, the synthetically assembled gene can be either cloned directly, or it can be amplified by PCR prior to cloning.

Alternatively, other methods for site directed mutagenesis can be employed for generation of the library insert, such as the Kunkel method (Kunkel TA. Rapid and efficient site-specific mutagenesis without phenotypic selection. Proc Natl Acad Sci USA. 1985 January; 82(2):488-92) or the DpnI method (Weiner M P, Costa G L, Schoettlin W, Cline J, Mathur E, Bauer J C. Site-directed mutagenesis of double-stranded DNA by the polymerase chain reaction. Gene. 1994 Dec. 30; 151 (1-2):119-23.).

For various purposes, it may be advantageous to introduce silent mutations into the sequence encoding the library insert. For example, restriction sites can be introduced which facilitate cloning or modular exchange of parts of the sequence. Another example for the introduction of silent mutations is the ability to "mark" libraries, that means to give them a specific codon at a selected position, allowing them (or selected clones derived from them) e.g. to be recognized during subsequent steps, in which for example different libraries with different characteristics can be mixed together and used as a mixture in the selection or panning procedure.

The invention also provides a method of producing an oligomer of modular antibody domains binding to a target comprising the steps of:
  providing a library of oligomers of modular antibody domains produced according to the inventive method as described
  contacting said library with said target in the presence of a scaffold ligand,
  selecting a library member binding to said target in the presence of a scaffold ligand, and
  manufacturing a preparation of the functional oligomer.

The scaffold ligand can be selected from the group consisting of an effector molecule, FcRn, Protein A and CDR target. As an example, the effector molecule can be selected from the group consisting of CD64, CD32, CD16, Fc receptors.

The oligomers can be dimers selected from the group of VH/VL, CH1/CL, CH2/CH2, CH3/CH3, Fc and Fab, or single chains thereof.

The method according to the invention can provide a library containing at least $10^2$ independent clones expressing functional oligomers of modular antibody domains or variants thereof.

Libraries as used according to the invention preferably comprise at least $10^2$ library members, more preferred at least $10^3$, more preferred at least $10^4$, more preferred at least $10^5$, more preferred at least $10^6$ library members, more preferred at least $10^7$, more preferred at least $10^8$, more preferred at least $10^9$, more preferred at least $10^{10}$, more preferred at least $10^{11}$, up to $10^{12}$ members of a library, preferably derived from a parent molecule, which is a functional modular antibody as a scaffold containing at least one specific function or binding moiety, and derivatives thereof to engineer a new binding site apart from the original functional binding region of said parent moiety.

Usually the libraries according to the invention further contain variants of the modular antibody, resulting from mutagenesis or randomization techniques. These variants include inactive or non-functional antibodies. Thus, it is preferred that any such libraries be screened with the appropriate assay for determining the functional effect. Preferred libraries, according to the invention, comprise at least $10^2$ variants of such modular antibodies, more preferred at least $10^3$, more preferred at least $10^4$, more preferred at least $10^5$, more preferred at least $10^6$, more preferred at least $10^7$, more preferred at least $10^8$, more preferred at least $10^9$, more preferred at least $10^{10}$, more preferred at least $10^{11}$, up to $10^{12}$ variants or higher to provide a highly diverse repertoire of antibodies for selecting the best suitable binders. Any such synthetic libraries may be generated using mutagenesis methods as disclosed herein.

Preferably the library is a yeast library and the yeast host cell exhibits at the surface of the cell the oligomers, or monomers that form oligomers, with the biological activity. The yeast host cell is preferably selected from the genera *Saccharomyces, Pichia, Hansenula, Schizisaccharomyces, Kluyveromyces, Yarrowia* and *Candida*. Most preferred, the host cell is *Pichia* or *Saccharomyces cerevisiae*.

The invention further provides a high quality library containing at least $10^2$ independent clones of functional dimers of modular antibody domains or variants thereof that are binding to a target and to a scaffold ligand. The target can be a ligand binding to a parent molecule subject to amino acid variation. The parent molecule can be a functional oligomer, in particular a functional Fc or a functional Fab, or part thereof.

As is well-known in the art, there is a variety of display and selection technologies that may be used for the identification and isolation of proteins with certain binding characteristics and affinities, including, for example, display technologies such as cellular and non-cellular, in particular mobilized display systems. Among the cellular systems the phage display, virus display, yeast or other eukaryotic cell display, such as mammalian or insect cell display, may be used. Mobilized systems are relating to display systems in the soluble form, such as in vitro display systems, among them ribosome display, mRNA display or nucleic acid display.

Methods for production and screening of antibody variants are well-known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76.

A library according to the invention may be designed as a dedicated library that contains at least 50% specific formats, preferably at least 60%, more preferred at least 70%, more preferred at least 80%, more preferred at least 90%, or those that mainly consist of specific antibody formats. Such a preferred library mainly contains the same kind of library members having similar structural features. Specific antibody formats are preferred, such that the preferred library according to the invention is selected from the group consisting of a VH library, VHH library, Vkappa library, Vlambda library, Fab library, a CH1/CL library, an Fc library and a CH3 library. Libraries characterized by the content of composite molecules containing more than one antibody domains, such as an IgG library or Fc library are specially preferred. Other preferred libraries are those containing T-cell receptors, forming T-cell receptor libraries. Further preferred libraries are epitope or peptide libraries, wherein the fusion protein comprises a molecule with a variant of an epitope, also enabling the selection of competitive molecules having similar binding function, but different functionality. Exemplary is a TNFalpha library, wherein trimers of the TNFalpha fusion protein are displayed by a single genetic package.

Another important aspect of the invention is that each potential binding domain remains physically associated with the particular DNA or RNA molecule which encodes it, and in addition, the fusion proteins oligomerize at the surface of a genetic package to present the binding polypeptide in the native and functional oligomeric structure. Once successful binding domains are identified, one may readily obtain the gene for expression, recombination or further engineering purposes. The form that this association takes is a "replicable genetic package", such as a virus, cell or spore which replicates and expresses the binding domain-encoding gene, and transports the binding domain to its outer surface. Another form is an in-vitro replicable genetic package such as ribosomes that link coding RNA with the translated protein. In ribosome display the genetic material is replicated by enzymatic amplification with polymerases.

Those cells or viruses or nucleic acid bearing the binding agents which recognize the target molecule are isolated and, if necessary, amplified. The genetic package preferably is M13 phage, and the protein includes the outer surface transport signal of the M13 gene III protein.

Preferably in the method of this invention the vector or plasmid of the genetic package is under tight control of the transcription regulatory element, and the culturing conditions are adjusted so that the amount or number of vector or phagemid particles displaying less than two copies of the fusion protein on the surface of the particle is less than about 20%. More preferably, the amount of vector or phagemid particles displaying less than two copies of the fusion protein is less than 10% the amount of particles displaying one or more copies of the fusion protein. Most preferably the amount is less than 1%.

The expression vector preferably used according to the invention is capable of expressing a binding polypeptide, and may be produced as follows: First a binding polypeptide gene library is synthesized by introducing a plurality of polynucleotides encoding different binding sequences. The plurality of polynucleotides may be synthesized in an appropriate amount to be joined in operable combination into a vector that can be propagated to express a fusion protein of said binding polypeptide. Alternatively the plurality of polynucleotides can also be amplified by polymerase chain reaction to obtain enough material for expression. However, this would only be advantageous if the binding polypeptide would be encoded by a large polynucleotide sequence, e.g. longer than 200 base pairs or sometimes longer than 300 base pairs. Thus, a diverse synthetic library is preferably formed, ready for selecting from said diverse library at least one expression vector capable of producing binding polypeptides having the desired preselected function and binding property, such as specificity.

The foregoing description will be more fully understood with reference to the following examples. Such examples are, however, merely representative of methods of practicing one or more embodiments of the present invention and should not be read as limiting the scope of invention.

EXAMPLES

Example 1

Construction of the Non-Focussed Fcab Library (Fcab01) and Phage Surface Display The crystal structure of an IgG1 Fc fragment, which is published in the Brookhaven Database as entry 1OQO.pdb was used to aid in the design of the Fcab library.

The sequence which was used as the basis for construction of the Fcab library is given in SEQ ID No. 1. In this sequence, the first amino acid corresponds to Glu 216 of human IgG1

(EU numbering; according to the IMGT database (http://imgt.cines.fr/textes/IMGTrepertoire/Proteins/protein/human/IGH/IGHC/Hu_IGHCallgenes.html; lookup 2007 Jun. 25), it is the first residue of the human IgG1 hinge region, which is given as: (E)PKSCDKTHTCPPCP) of the heavy constant chain hinge region of human IgG1.) The second-last residue of SEQ ID No. 1 corresponds to Gly 446 of human IgG1 (EU numbering; IMGT: residue number 129 of the CH3 domain of human IgG1).

After detailed analysis of the structure of 1oqo.pdb and by visual inspection of the residues forming the loops which connect the beta strands, it was decided to randomize residues 144, 145 and 146, which are part of the loop connecting beta strand A-B as well as 198, 199, 200, 203 and 204, which are part of the loop connecting beta strand E-F of SEQ ID No. 1. In addition to the mutated residues, 5 residues were inserted at residue number 198 of SEQ ID No. 1. In SEQ ID No. 2, the sequence of the library insert of library Fcab01 is given in which all randomized residue positions as well as the 5 inserted residues are designated with the letter X.

The engineered gene was produced by a series of PCR reactions using degenerate primers followed by ligation of the resulting PCR products. To facilitate ligation, some of the codons of the nucleotide sequence coding for SEQ ID No. 1 were modified to produce restriction sites without changing the amino acid sequences (silent mutations). For insertion into the cloning vector pHEN1 (Nucleic Acids Res. 1991 Aug. 11; 19(15):4133-7. Multi-subunit proteins on the surface of filamentous phage: methodologies for displaying antibody (Fab) heavy and light chains. Hoogenboom H R, Griffiths A D, Johnson K S, Chiswell D J, Hudson P, Winter G.) in frame with the pelB secretion signal, the NcoI restriction site close to the 3' end of the pelB secretion signal was used. For the randomized residues, the codon NNS (IUPAC code, where S means nucleotides C and G) was chosen which encodes all 20 naturally occurring amino acids, but avoids 2 out of 3 stop codons. Other codons such as for example the NNB (B meaning nucleotides T, C and G) can also be used. The engineered sequence is given as a nucleotide sequence in SEQ ID No. 3. This sequence also includes the restriction sites used for cloning into the phagmid display vector pHEN1, namely an NcoI site at the 5' end and a NotI site at the 3' end.

The sequences of the PCR primers used for assembly of the mutated CH3 domain are given in SEQ ID No. 4 through SEQ ID No. 9.

(PCR primer EPKSNCO)
SEQ ID No. 4
ccatggccgagcccaaatcttgtgacaaaactc (PCR primer CH3LSAC)
SEQ ID No. 5
agtcgagctcgtcacgggatggggcaggg (PCR primer CH3CSAC)
SEQ ID No. 6
gtacgagctcnnsnnsnnscaagtcagcctgacctgcctgg (PCR primer CH3CHIN)
SEQ ID No. 7
tgccaagcttgctgtagaggaagaaggagccg (PCR primer CH3RHIN)
SEQ ID No. 8
tgccaagcttaccgtgnnsnnsnnsaggtggnnsnnsggggaacgtcttct catgctccg (PCR primer CH3RNOT)
SEQ ID No. 9
agttgcggccgctttacccggagacagggagag FIG. 1 shows a schematic presentation of the PCR fragments generated for assembly of the mutated gene, and the primers used therefore.

cDNA of the heavy chain of the human monoclonal antibody 3D6 (Felgenhauer M, Kohl J, Rüker F. Nucleotide sequences of the cDNAs encoding the V-regions of H- and L-chains of a human mono-clonal antibody specific to HIV-1-gp41. Nucleic Acids Res. 1990 Aug. 25; 18(16):4927.) was used as template for the PCR reactions. The 3 PCR products were digested with SacI and/or HindIII respectively and ligated together. The ligation product was further digested with NcoI and NotI and ligated into the surface display phagmid vector pHEN1, which had previously been digested with NcoI and NotI. The ligation product was then transformed into E. coli by electroporation. A number of selected clones were controlled by restriction analysis and by DNA sequencing and were found to contain the insert as planned, including the correctly inserted randomized sequences. For the following steps of phage preparation, standard protocols were followed. Briefly, the ligation mixture was transformed into E. coli TG1 cells by electroporation. Subsequently, phage particles were rescued from E. coli TG1 cells with helper phage M13-KO7. Phage particles were then precipitated from culture supernatant with PEG/NaCl in 2 steps, dissolved in water and used for selection by panning or, alternatively, they were stored at minus 80° C.

Example 2

Construction of the Focussed Fcab Library (Fcab02) And Phage Surface Display

As described in example 1, an Fcab library was prepared in which the randomized library positions are fully randomized, i.e. they are encoded by a codon such as NNS, NNB, NNK, NNN or others are used.

For clarity, the meaning of the letters such as N, B, S or K is defined by the IUPAC nucleotide ambiguity code, which is given in the following table:

TABLE 1

IUPAC nucleotide ambiguity code

| Symbol | Meaning | Nucleic Acid |
|--------|---------|--------------|
| A | A | Adenine |
| C | C | Cytosine |
| G | G | Guanine |
| T | T | Thymine |
| U | U | Uracil |
| M | A or C | |
| R | A or G | |
| W | A or T | |
| S | C or G | |
| Y | C or T | |

TABLE 1-continued

IUPAC nucleotide ambiguity code

| Symbol | Meaning | Nucleic Acid |
|---|---|---|
| K | G or T | |
| V | A or C or G | |
| H | A or C or T | |
| D | A or G or T | |
| B | C or G or T | |
| X | G or A or T or C | |
| N | G or A or T or C | |

Source: Nomenclature for incompletely specified bases in nucleic acid sequences: recommendations 1984. A Cornish-Bowden, Nucleic Acids Res. 1985 May 10; 13(9): 3021-3030.

These codons given above are designed such that all 20 amino acids are encoded by them. It may be preferable to choose subsets out of the possible amino acids. Examples can be found in the literature (Fellouse F A, Li B, Compaan D M, Peden A A, Hymowitz S G, Sidhu S S. Molecular recognition by a binary code. J Mol Biol. 2005 May 20; 348(5):1153-62. Epub 2005 Apr. 1.; Fellouse F A, Wiesmann C, Sidhu S S. Synthetic antibodies from a four-amino-acid code: a dominant role for tyrosine in antigen recognition. Proc Natl Acad Sci USA. 2004 Aug. 24; 101(34):12467-72. Epub 2004 Aug. 11.). Focused libraries which for example allow for only 4 different amino acid types can be constructed e.g. by employing the codon KMT, which codes for the amino acids Ser, Tyr, Ala and Asp.

A focused Fcab library, designated Fcab02, has been constructed in the same way as described in example 1, except that the NNS codons were replaced by KMT codons.

Therefore, the letter "X" in SEQ ID No. 2 now means "S, Y, A and D" (Ser, Tyr, Ala and Asp) in order to describe the focused library Fcab02

Example 3

Construction of a Phage Surface Display Library With Additional Amino Acid Residues Between the Library Insert (Binding Partner) and p3

In order to investigate accessibility of the potential binding site of the displayed protein a binding assay is performed: the phage suspension is reacted with anti-myc mAb 9E10-coated microplates (or immunotubes). After washing, the bound phages are detected with anti-M13-enzyme conjugate. As a control, helper phage—which does not display the protein fusion and the myc-tag is reacted with the plates. Other controls are reaction of phages with non-coated plates and reaction of phages with antiserum recognizing the p3-fusion partner of the phages.

Ideally, the anti-myc-reactivity of phages displaying the p3-fusion protein should give very clear ELISA readouts whereas helper phage reactions to anti-myc-mAb should not be above background (non-coated plates). The structure of a CH3 dimer displayed at the surface of an M13 phage through binding to protein III as an anchor is such, that each CH3 is anchored to protein III using various linker length and compositions. Thus, the CH3 dimer is preferably displayed by two anchors.

Linker Optimization:

The linker between the protein to be displayed and the anchor protein of the genetic package (in case of filamentous phage e.g. p3, p8, pX, pIX, pVII) is especially important if the potential binding site of the displayed molecule is in spatial vicinity of the phage particle. In antibody libraries utilizing variable domains and antigen binding sites formed by CDR-loops and display of the library members as amino-terminal fusion to p3 the potential antigen binding site is directed away from the phage particle. Therefore, the linker structure between library members and the phage coat protein is less important. Engineering the bottom loops of immunoglobulin domains and performing phage display may however be an inefficient process and decrease yields of antigen binding clones or even preclude it. Varying the linker between a library member protein and its fusion partner on the surface can solve or may at least reduce this problem. In order to select for optimal linker sequences (in terms of length and flexibility as well as stability) a library of linkers can be prepared in which the anchor protein at the surface of the genetic replicable package is fused to a known binding protein which is for sterical reasons notoriously difficult to select for.

This library of sequences can be varied in length and amino acid content.

Selection methods of the linker library for optimal linkers depend on the application but basically it should be for selecting all properties one wishes to have in a certain methodology. Enrichment against a difficult to select for antigen may yield linker sequences which allow library members a good access to the antigen. Incubation in protease solutions or under other harsh conditions or frequent passaging through host cells under proteolytic conditions (e.g. old microbial cultures) may be an appropriate selection for stable display linkers.

A library of linkers may be produced by any well known library technology. Synthetic linker sequence lengths may vary between 10-500 amino acids. Alternatively, linker can be complete proteins known to be of flexible nature.

Linker Optimization Fcab01:

As an example, library Fcab01 (as described in example 1) can be used. Originally, this library is cloned in the phagmid display vector pHEN1, using NcoI and NotI restriction sites. When cloned in this manner, 18 amino acid residues are in between the C-terminal amino acid residue of the Fcab01 library insert and the N-terminal amino acid residue of phage M13 p3. The sequence of this junction region is given in SEQ ID No.10 SPGKAAAEQKLISEEDLNGAATVES—and is explained as follows: the first 4 residues, SPGK (SEQ ID No. 83), are the 4 C-terminal residues of the Fcab01 library insert, followed by the amino acid sequence AAA, which is the amino acid residues encoded by the NotI restriction site, followed by the sequence EQKLISEEDL (SEQ ID No. 84), which is the myc epitope, followed by NGAA (SEQ ID No. 85), after which there is an amber stop codon, which is translated to Glutamine (Q) in amber suppressor strains of *E. coli* such as TG1. The C-terminal 4 residues of SEQ ID No.10, TVES (SEQ ID No. 86), are the N-terminal 4 residues of phage M13 p3 as present in the vector pHEN1.

In order to construct a phage which displays an Fcab insert with an increased distance between the Fcab (the binding partner) and the body of the phage (the genetic package), 5 additional residues were inserted at the C-terminus of the Fcab insert FcabRGD4, directly upstream of the NotI cloning site, resulting in the clone FcabRGD4L. FcabRGD4 is an Fcab that has an integrin-binding RGD motif inserted in the EF-loop of the CH3 domain and which binds to αvβ3-integrin in ELISA. As an increased-length linker sequence, the amino acid sequence EGGGS, which appears 8 times in the phage M13 p3 sequence was used. The resulting amino acid sequence of FcabRGD4L as expressed after cloning in pHEN1 is given in SEQ ID No. 11. In SEQ ID No. 11, amino acid residues 198-204 represent the RGD motif, amino acid residue 237 is the C-terminal residue of the Fcab insert, residues 238-242 represent the inserted linker sequence (which is the difference to unmodified pHEN1), which is followed by myc tag, amber stop codon and the p3 sequence.

For cloning of the construct, the FcabRGD4 sequence was amplified from pHENFcabRGD4 (SEQ ID No. 12) using PCR primers EPKSNCO (SEQ ID No. 4) and CH3rlink actagcggccgcagagccaccaccctccttacccggagacagggagag (SEQ ID No. 13) and cloned via NcoI and NotI restriction sites into the vector pHEN1. The resulting vector, pHENFcabRGD4L (SEQ ID. No. 14) has the additional linker sequence at nucleotide positions 3057-3071.

The two phagemid vectors, pHENFcabRGD4 and pHENFcabRGD4L were transformed into *E. coli* TG1. Subsequently, phage particles were rescued from *E. coli* TG1 cells with helper phage M13-KO7. Phage particles were then precipitated from culture supernatant with PEG/NaCl in 2 steps, dissolved in water and used for ELISA.

Phage ELISA was Performed as Follows:

The phage suspension is reacted with αvβ3-integrin-coated microplates (or immunotubes). After washing, the bound phages are detected with anti-M13-enzyme conjugate. As controls, helper phage—which does not display the protein fusion and the myc-tag is reacted with the plates as well as phage particles carrying wtFcab on their surface. Other controls are reaction of phages with non-coated plates and reaction of phages with antiserum recognizing the Fcab-fusion partner of the phages. Phage particles with the increased-length linker resulting from pHENFcabRGD4L react more readily with αvβ3-integrin than phage particles with the original linker as contained in pHENFcabRGD4, and therefore give a stronger signal in ELISA.

Phage selections can be performed in which phage particles with wtFcab are mixed with small amounts of phage particles carrying either FcabRGD4 or FcabRGD4L. After several (typically 3-5) rounds of panning, preferentially phages displaying FcabRGD4L are selected.

Example 4

Fcab Library Design ("Fcab" is a Registered Trademark of F-Star Biotechnologische Forschungs-und Entwicklungsges.m.b.H.)

Figure 2:
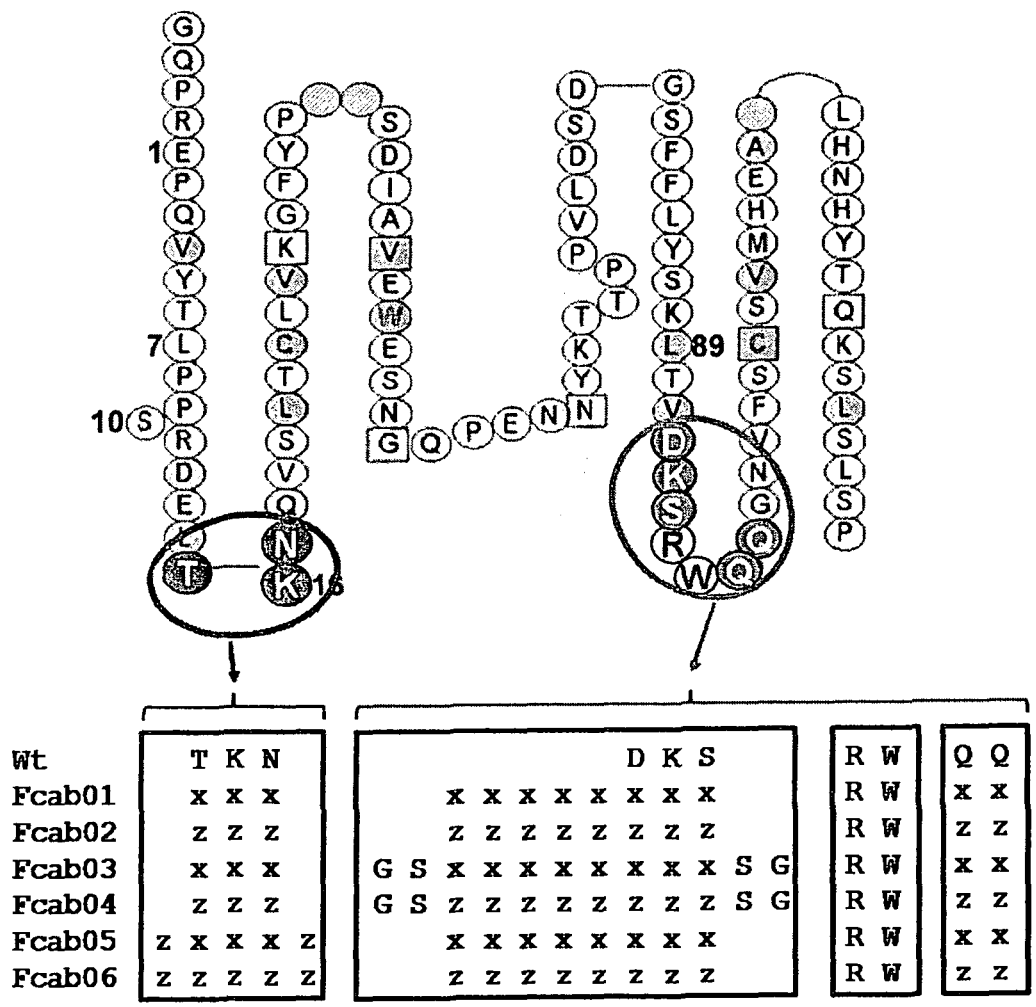

Design of Fcab Libraries (illustrated in FIG. 2): amino acid positions in non CDR-loops of CH3 constant domains of antibodies are considered for randomization. Especially loops A-B, C-D and E-F are considered as they are on one side of the domain. Some of the design criteria for randomization at a certain position are described herein.

Amino acids frequently involved in antigen antibody interactions are described herein to be included in a focused library. Here the amino acids Ala, Asp, Ser and Tyr are used to design the focused library.

Libraries with restricted amino acid utilization have been shown to be sufficient to generate binders against virtually any antigen (Sidhu & Fellhouse, NATURE CHEMICAL BIOLOGY VOLUME 2 page 682ff; Koide et al PNAS, volume 104 p 6632-6637). The advantage of such restricted (or focused) libraries is that they can be covered completely by current technologies. Ideally, the amino acid utilization reflects a natural amino acid utilization of ligand receptor binding. However, even libraries utilizing only 2 amino acids (Tyrosine and Serine) have been reported to yield good selection results (in terms of frequency of binders against different binders and in terms of affinity).

Loop Flexibility:

Certain loop structures may be required by the scaffold protein in order to keep the overall natural structure. Randomizing many amino acid positions in loops and even elongation of loops may be facilitated by building certain sequences either on one or on both sides of the randomized positions. These sequences may be flexible sequences in order to allow to compensate for any tensions with certain library sequences in such a position.

TABLE 2

Exemplary Fcab ™ libraries, focused and non-focused

|  | # of randomized positions | Theoretical diversity on amino acid level | Number of independent bacterial clones |
|---|---|---|---|
| Fcab01 | 13 | $8.2 \times 10^{16}$ | $0.6 \times 10^9$ |
| Fcab02 | 13, focused | $6.7 \times 10^7$ | $0.6 \times 10^9$ |
| Fcab03 | 13 | $8.2 \times 10^{16}$ | $1.0 \times 10^9$ |
| Fcab04 | 13, focused | $6.7 \times 10^7$ | $0.8 \times 10^9$ |
| Fcab05 | 15 | $1.3 \times 10^{18}$ | $0.8 \times 10^9$ |
| Fcab06 | 15, focused | $1.3 \times 10^9$ | $1.0 \times 10^9$ |

Fcab01 library is described in the examples above. The sequence space of the focused library designs Fcab02, Fcab04 and Fcab06 are covered by the actual bacterial library sizes of approximately 10e9. In contrast, the completely randomized libraries Fcab01, Fcab03 and Fcab05 are actually grossly underrepresented.

Example 5

Cloning of Yeast Display Libraries by Homologous Recombination

Vector pYD1 (Invitrogen) is used as the basic vector. The vector is modified as follows, in order to remove an XhoI site: pYD1 is cleaved with XhoI, treated with Klenow fragment of DNA polymerase and religated. The resulting sequence is given in pYD1dX (SEQ ID No. 15).

pYD1dX contains a unique BamHI restriction site at position 921/925 and a unique NotI restriction site at position 963/967. It is opened with these two restriction enzymes.

An insert encoding CH1-hinge-CH2-CH3 from human IgG1 is prepared by PCR from cDNA encoding the heavy chain of a human IgG1 monoclonal antibody. In this insert, a point mutation is introduced using standard procedures to mutate the C-terminal Cystein residue of the CH1 domain to a Serine. The insert is amplified using PCR primers that attached a BamHI and a Not restriction site to both ends respectively. These restriction sites are then used for cloning the insert into pYD1dX to yield the display vector pYD1dXFc (SEQ Id No. 16). The mutated codon at the C-terminus of the CH1 domain (Cys to Ser) is at positions 1233-1235 in the sequence pYD1DxFc. The stop codon of the insert is at position 1917/1919.

This vector is used as a positive control for the display of human CH1-hinge-CH2-CH3 on the surface of yeast and as a starting point for the construction of the vector pYD1CH12 (see below).

Cloning of Libraries

Cloning of libraries in which mutations are introduced into structural loops of CH3 domains is performed in yeast by homologous recombination (gap repair). For this purpose, a recipient vector is prepared that lacks the CH3 domain: pYD1dXFc is cleaved with XhoI (position 1603/1607) and NotI (position 1921/1925), the large fragment is prepared by preparative gel electrophoresis, treated with Klenow fragment of DNA polymerase and re-ligated. This procedure reconstitutes a unique XhoI site (position 1603/1607) and yielded vector pYD1CH12 (SEQ ID No. 17). pYD1CH12 is subsequently cleaved with XhoI and is used as recipient vector for gap repair in yeast.

As a source of insert, Fcab libraries Fcab01 (SEQ ID No. 18), Fcab02 (SEQ ID No. 19), Fcab03 (SEQ ID No. 20), Fcab04 (SEQ ID No. 21), Fcab05 (SEQ ID No. 22) and Fcab06 (SEQ ID No. 23) are used. These libraries are prepared by standard DNA synthesis, and contain randomized residues as well as inserted residues in the AB loop (between residues 359 and 361 (EU numbering)) as well as in the EF loop (between residues 413 and 419 (EU numbering)) of the CH3 domain of human IgG1. From this synthetic DNA, the insert for gap repair in yeast is amplified by PCR using PCR primer pair gapch35 caacaaggccctgcctgccccccat cgagaagac-catctccaaggccaagggccagcctcgagaaccacaggtgtacaccctgcc (SEQ ID No. 24) and gapfcs3 gagaccgaggagagggttagggatag-gcttacct tcgaagggccctctagactcgatc-gagcggccgctcatttacccggagacagggagagctc ttc (SEQ ID No. 25). 100 µg of XhoI cleaved vector pYD1CH12 and 100 µg of insert are mixed and transformed in *Saccharomyces* strain EBY100 (Invitrogen) using the Lithium acetate procedure according to the following protocol, which is upscaled by a factor 100 to transform the required amount of cells and of DNA. Briefly, for a single transformation of 1 µg vector DNA and 1 µg insert DNA, 10 ml of YPD (2% peptone, 2% dextrose (D-glucose)) are inoculated with a yeast colony and shaken overnight at 30° C. The OD600 of the overnight culture is determined and the culture diluted to an OD600 of 0.4 in 50 ml of YPD and grown for an additional 6 hours. Cells are pelleted at 2500 rpm and resuspended in 40 ml distilled water. Cells are pelleted again at 2500 rpm and resuspended in 100 mM LiAc, followed by incubation at 30° C. for 30 minutes. 1 µg vector DNA, 1 µg insert and 50 µl denatured sheared salmon sperm DNA (2 mg/ml) are mixed with 300 µl of the yeast suspension. 700 µl of a solution of 200 mM Li-acetate and 40% PEG-3350 are added and mixed with the yeast/DNA suspension, followed by incubation at 30° C. for 30 minutes. 88 µl DMSO are added, mixed and the mixture is incubated at 42° C. for 40 minutes, followed by centrifugation in a micro-centrifuge for 10 seconds. The supernatant is then removed, the cell pellet is resuspended in 1 ml distilled water. The pellet is then resuspended in 50-100 µl TE and plated on minimal dextrose plates containing leucine (10 g/l yeast nitrogen base, 20 g/l dextrose, 0.1 g/l leucine, 15 g/l agar). After incubation of the plates at 30° C. for 2 to 4 days single colonies appeared that are subsequently harvested.

Cultivation—Induction

The harvested yeast libraries (yFcab libraries) are inoculated in 10 ml SD-CAA medium (10 g/l yeast nitrogen base, 10 g/l casamino acids, and 20 g/l dextrose, 0.1 g/l leucine, 9.67 g/l NaH2PO4.2H2O and 10.19 g/l Na2HPO4.7H2O) and grown on a shaker at 250 rpm at 28° C. for 6-8 hours. The OD600 of the culture is determined, and the culture is diluted to an OD600 of 0.2, and grown under the same conditions until an OD600 of 1-2 is reached. Cells are harvested by centrifugation (3000 rpm/5 min/4° C.) and resuspended in induction medium SG/R-CAA (10 g/l yeast nitrogen base, 10 g/l casamino acids, and 20 g/l galactose, 10 g/l raffinose, 0.1 g/l leucine, 9.67 g/l NaH2PO4.2H2O and 10.19 g/l Na2HPO4.7H2O). Cultures are induced by incubation for 2 days on a shaker at 250 rpm at 20° C. and subsequently analysed and sorted.

Quality Control of yFcab Libraries.

yFcab libraries are tested for their expression level and quality of expressed Fcab's two days after induction with SD-CAA medium. The expression level is tested using a polyclonal anti human IgG-Fc antiserum (Sigma). For this purpose 0.5×10e6 library cells are diluted in 1 ml staining buffer (SB), which comprises PBS with 2% BSA. Cells are pelleted and stained with 100 µl SB containing 1/2000 diluted anti human IgG-Fc-PE antiserum (Sigma) for 30 min on ice, washed twice with SB and subsequently analyzed in the FACS. In general 70%-80% of all cells in each library express Fcabs on their cell surface. To test correct folding of Fcabs, staining with Protein A is performed. Again 0.5×10e6 library cells are diluted in 1 ml staining buffer SB, cells are pelleted and stained with 100 µl SB containing 1 µg/ml Prot-A-FITC (Fluka) for 30' on ice, washed twice with SB and subsequently analyzed in the FACS. In general, the yFcab libraries as described above show ≥40% Prot A positive cells. In order to test whether the Fcabs are expressed as dimers on the surface of the cells a staining with human CD64 is performed. The affinity of CD64 is too low for efficient monomeric binding therefore CD64 complexes with dimers are used. For this purpose e.g. 1 µg recombinant CD64 from R&D Systems (containing a HIS-tag) is mixed with 1 µg anti Penta HIS-alexafluor 488 (from Qiagen) in 1 ml SB (total volume). yFcab libraries are tested for binding to CD64 by incubating the 5×10e5 cells with 100 µl of the complex-mixture for 30 minutes on ice, as control the cells are incubated with equivalent of the anti HIS-alexafluor 488 alone (1/200 dilution in SB). After incubation the cells are washed twice with ice cold SB and analysed in the FACS. In general >50% of all cells in each library express dimeric Fcabs on their cell surface.

Biotinylation of Antigen (Her2)

Recombinant antigen e.g. Her2 (Bendermedsystems) was done with the EZ link system of Pierce according to the manufacturers instruction. In short, the antigen is dialyzed against PBS, diluted to 1 mg/ml in PBS and mixed with 10 mM sulfo-LC-LC-biotin (EZ link, Pierce), which was predissolved in water. The final ratio between antigen and biotin is 1:3 and the mixture is incubated at room temperature from 30'. Afterwards the mixture is "dialyzed" against PBS using Vivaspin MWCO3000 (Sartorius) columns (5×8', 4000 rpm). Finally the concentration of the biotinylated antigen (Her2) is tested by HPLC and aliquots are stored at −20° C.

The quality of the biotinylated antigen is tested by ELISA. First the plates are coated with an anti-Her2 antibody (e.g. Herceptin) at 10 µg/ml in PBS, 100 µl/well overnight at 4° C., after this the plate is washed 3× with washing buffer (WB) (PBS+0.05% Tween20) and blocked by blocking buffer (BB) (PBS+2% BSA) 1 h at room temperature. After 3× washing with WB, different concentrations of Her2-biotin are added in 100 µl/well BB for 1 h at room temperature, followed by 3× washing with WB. Finally the plate is incubated with 1:25000 streptavidin-HRP (GE healthcare) in BB for 1 h at room temperature and washed 3× with WB. Colour is developed by adding 100 µl/well of the substrate TMB (Sigma) after ~10 minutes the reaction is stopped by adding 100 µl/well of 30% $H_2SO_4$. The results is analysed with an ELISA reader at 450-630 nm.

Example 6

Production of Antigen Specific (Her2) Fcabs

Selection of Antigen Specific (Her2) Fcabs Using FACS First Selection Round:

Two days before FACSorting a yeast library containing $2.5 \times 10e8$ individual Fcab clones is induced with SG/R-CAA medium to express the Fcabs on their cell surface as described above. After two days, the amount of cells covering e.g. 10 times the library ($=2.5 \times 10e9$) is incubated for 30 minutes on ice with 500 nM biotinylated antigen (Her2) in 2 ml SB. Then the cells are washed once with cold SB and subsequently incubated for 30' on ice with streptavidin-PE (from R&D systems) diluted 1:100 in SB. The cells are washed twice with ice cold SB and diluted to an end concentration of $1 \times 10e9$ cells/ml. Control stainings with $5 \times 10e6$ cell/ml in 100 µl are made with streptavidin-PE only, in the absence of antigen. Both the complete library and the control stainings are analysed in e.g. a FACS ARIA from BD. To set the gates for sorting the control cells are used. First a FSC/SSC gate (G1) is set to identify healthy yeast cells, from G1 a FSC-width versus FSC-area plot is made and only non-aggregating cells are selected in a new gate (G2). Cells in G2 are subsequently analysed for reactivity with streptavidin-PE using FSC versus FL-2 (PE channel). G3 is set to include 0.1% of (false) positive cells. Subsequently, at least $5 \times 10e8$ stained cells (twice the library size ideally more) are analysed with the settings as indicated above and the cells in G3 are sorted into a tube containing 2-3 ml SD-CAA medium. Roughly $5 \times 10e5$ cells (Pool1) are harvested in the first round of selection and propagated for 1 to 2 days, after which the cells can be stored at $-80°$ C. and aliquots can be induced to express the Fcabs as described above. After two more days the next selection round can take place.

Second Selection Round:

Pool1 selected in round 1 are induced to express the Fcab on their surface as described above. At least $5 \times 10e6$ cells (comprising multiple copies of Pool1) are incubated for 30' on ice with 500 nM biotinylated antigen (Her2) in 1 ml SB. Then the cells are washed once with cold SB and subsequently incubated for 30' on ice with streptavidin-PE (from R&D systems) diluted 1 in 100 in SB together with 2 µg/ml Protein A-FITC (Fluke). Next the cells are washed twice with ice cold SB and diluted to an end concentration of $\sim 2 \times 10e6$ cells/ml. In addition, control stainings are made in which $5 \times 10e6$ cells/ml of Pool1 in 100 µl cells are incubated with a mixture of Prot A and streptavidin-PE as indicated above, but without the incubation with the antigen (Her2). In addition, $5 \times 10e5$ cell in 100 µl of a yeast clone expressing Fcab wt non randomized Fc fragment) is stained with Prot A-FITC as described above in the absence of streptavidin-PE. Fcab-wt expressing cells are analysed in e.g. a FACS ARIA from BD to set gates for sorting. First a FSC/SSC gate (G1) is set to identify healthy yeast cells, from G1 a FSC-width versus FSC-area plot is made and only non aggregating cells are selected in new gate (G2).

Cells in G2 are subsequently analysed for Protein A expression using FSC versus FL-1 (FITC). G3 is set to cover strong Prot A positive cells (50-60% of parent gate) and G4 is set to cover weak Prot A positive cells (20-30% of parent cells). G3+G4 will include roughly 70-80% of all cells in G2. Now the Pool cells stained for streptavidin-PE in the presence of Prot A-FITC are used to set the rest of the sorting gates. First G1 and G2 are checked with the Pool cells and if necessary adjusted. Pool cells will have lesser events in G3 and maybe also in G4 indicating that not all cells in Pool1 express Fcabs that are folded as the Fcab-wt. Using the control stained Pool cells a new gate is prepared both for G3 and G4. The new gates are set in a plot FSC and FL-2 (PE). Gate (G5) is prepared that includes 0.1% (false) streptavidin positive cells in G3 and the same is done for cells in G4 resulting in G6. In the next step at least $5 \times 10e6$ cells stained for Her2-biotin+streptavidin-PE and Prot A-FITC are sorted by the FACS-ARIA. Cells are collected from G5 (Pool2.1 and G6 (Pool2.2) in separate tubes containing 2-3 ml yeast culture medium. Between 10 and 1000 clones can be expected from both gates. Both new pools are propagated for 1 or 2 days and stored at $-80°$ C. Cells from 2.1 and 2.2 may be either used for direct further sorting in a third round or they may be subjected, (preferably after mixing the two clone together again) to a round of additional randomization of the AB loop (affinity maturation) before they are further sorted in FACS.

Affinity Maturation for Selected Clones/Pools

For affinity maturation, diversity is introduced in selected clones or in pools of selected clones in the AB loop. For this purpose, a PCR is made with a primer that contained degenerate codons at positions 359, 360 and 361 (EU numbering) (primer Abmut, gaaccacaggtgtacaccctgc-ccccatcccgggatgagctgnnbnnbnnbca ggtcagcctgacctgcc tggt-caaag, SEQ ID No. 26) or alternatively with a primer that contained degenerate codons at positions 358, 359, 360, 361 and 362 (EU numbering) (primer Abmut2LR, gaaccacaggtg-tacaccctgcccccatcccgggatgagnnbnnbnnbnnbgtcagc ctgacctgcctggtcaaag, SEQ ID No. 27). The second primer used in these PCRs is gapfcs3 in both cases. In order to create flanking sequences for efficient gap repair in yeast, the resulting PCR products are further amplified with the primer pair gapch35 and gapfsc3 and subsequently transformed in *Saccharomyces cerevisiae* strain EBY100 by Lithiumacetate transformation together with XhoI cleaved pYD1CH12 as described above. As alternative primers for randomization of the described residues in the AB loop, primers such as Abmut1L (gaaccacaggtgtacaccctgc-ccccatcccgggatgagnnbnnbnnbnnbcaggtcagc ctgacctgcctggt-caaag, SEQ ID No. 28) or Abmut1R (gaaccacaggtgta caccct-gcccccatcccgggatgagctgnnbnnbnnbnnbgtcagcctgacctgcctggtc aaag, SEQ ID No. 29) can also be used. In an analogous manner, residues in the EF loop can be randomized e.g. by total randomization or by randomization using spiked oligonucleotides as primers or by similar mutagenesis techniques. The Abmut primer will result in 8000 new variants (Pool2.3) of each clone and the Abmut2LR primer with lead to $3 \times 10e6$ new variants (Pool2.4). Therefore Pools 2.3. and 2.4 will both results in new libraries of approximately 10e8 individual since the starting material (Pool2.1+2.2) already contains approximately 10-1000 clones.

Third Selection Round

Affinity matured pools 2.3 and 2.4 and if necessary Pool2.1 (only the Prot A positive cells are preferred) are induced to express Fcabs on their cell surface as described above and subsequently sorted as described for "Second selection round", with exception that the Pools 2.3 and 2.4 are much bigger and therefore staining volumes for the pools are equal to those of the library staining described in "First selection round". In the third selection round, only Her2 positive/Prot A positive cells are sorted. Pools derived from these selections contain typically >20% Her2/Prot A positive cells. If not then a fourth and fifth (or even more) round(s) of selection combining Prot A with Her2 can be performed.

Clone Analyses:

Individual clones from pools containing Her2/Prot A cells (>20% is preferred) are prepared either by plating the pools on agar plates with SD-CAA medium or by sorting the singles cells (=clones) directly from the FACS ARIA onto the plates without generating a pool. Clones are allowed to grow and are transferred to liquid cultures and stored in −80° C. Aliquots of the clones are subsequently induced to express Fcabs on their cell surface as described above and screened for a number of parameters in the FACS. These parameters may be: a dose response range of the antigen used for selection (Her2) with and without the presence of Prot A-FITC, CD64 staining as described above. In addition using similar staining protocols a number of irrelevant biotinylated antigen can be screened to identify non-cross reacting Fcabs.

It is to be expected that, after several rounds of selecting antigen (Her2)+Prot A positive cells, a large percentage of clones show >25% antigen (Her2) positivity when stained with 500 nM antigen (Her2) and >70% Prot A positivity when stained with 2 μg/ml Prot A-FITC. In most of the cases these clones will also show >50% CD64 binding. Thus mimicking the Prot A and CD64 levels of non-randomized Fc fragments (Fcab wt) expressed on yeast.

Clones selected as described above with characteristics as described above are now ready to be produced as soluble molecules. This can be done by transient transfection or by stable transfection of the Fcab DNA into new host cells. For this purpose the DNA from individual yeast clones is isolated using standard procedures. The relevant DNA coding for the complete CH3 domain or only the part of the CH3 domain that is randomized in the library is amplified by PCR and transferred into a new expression vector containing the missing part of the Fcab+a suitable promoter and one of more selection markers such as G418, that allows selection of transfected cells out of a pool of non transfected cells. The new vector is then e.g. transiently transfected into a new host cell such as HEK293 or CHO. The host cells are allowed to recover and are subsequently cultured for a number of days. The supernatant of the cultures with contain the soluble Fcab which can be used for further testing with or without purification over e.g. Prot A. Stable cell lines can also be made by standard procedures.

TABLE 2

Sequences of selected Her2 clones: with reference to numbering of Seq. ID No. 1

| Clone name | AB loop AA143ff | EF Loop AA198ff |
|---|---|---|
| Fcab wt | LTKNQ (SEQ ID No. 87) | -----DKSRWQQ (SEQ ID No. 88) |
| y-Her.C2-P3.1-1 | LDNSQ (SEQ ID No. 30) | IRSSVGSRRWWS (SEQ ID No. 51) |
| y-Her.C2-P3.1-3 | YEGSS (SEQ ID No. 31) | ARYSPRMLRWAH (SEQ ID No. 52) |
| y-Her.C2-P3.1-5 | YMSAD (SEQ ID No. 32) | SRRDSSLLRWAH (SEQ ID No. 53) |
| y-Her.C2-P3.1-6 | YRRGD (SEQ ID No. 33) | APGSKGYRRWAL (SEQ ID No. 54) |
| y-Her.C2-P3.1-8 | LMSRQ (SEQ ID No. 34) | DKPFWGTSRWSR (SEQ ID No. 55) |
| y-Her.C2-P3.1-16 | LHLAQ (SEQ ID No. 35) | SINDLINHRWPY (SEQ ID No. 56) |
| y-Her.C2-P3.1-18 | YLSKD (SEQ ID No. 36) | MWGSRDYWRWSH (SEQ ID No. 57) |
| y-Her.C2-P3.2-3 | YRSGS (SEQ ID No. 37) | NSGSAMMVRWAH (SEQ ID No. 58) |
| y-Her.C2-P3.2-9 | LRDGQ (SEQ ID No. 38) | QRSRLSRQRWWR (SEQ ID No. 59) |
| y-Her.C2.P4.2-1 | YSANT (SEQ ID No. 39) | ARYSPRMLRWAH (SEQ ID No. 60) |
| y-Her.C2.P4.2-3 | YASNT (SEQ ID No. 40) | ARYSPRMLRWAH (SEQ ID No. 61) |
| y-Her.C2.P4.2-4 | YSDGD (SEQ ID No. 41) | ARYSPRMLRWAH (SEQ ID No. 62) |
| y-Her.C2.P4.2-5 | YSGGS (SEQ ID No. 42) | ARYSPRMLRWAH (SEQ ID No. 63) |
| y-Her.C2.P4.2-6 | YGRDS (SEQ ID No. 43) | ARYSPRMLRWAH (SEQ ID No. 64) |
| y-Her.C2.P4.2-8 | YAGGT (SEQ ID No. 44) | ARYSPRMLRWAH (SEQ ID No. 65) |
| y-Her.C2.P4.2-10 | YSSDS (SEQ ID No. 45) | ARYSPRMLRWAH (SEQ ID No. 66) |
| y-Her.C2.P4.2-12 | YHSGS (SEQ ID No. 46) | ARYSPRMLRWAH (SEQ ID No. 67) |
| y-Her.C2.P4.2-15 | YLTNS (SEQ ID No. 47) | ARYSPRMLRWAH (SEQ ID No. 68) |
| y-Her.C2.P4.2-18 | YGSEE (SEQ ID No. 48) | ARYSPRMLRWAH (SEQ ID No. 69) |
| y-Her.C2.P4.2-19 | YRSGE (SEQ ID No. 49) | ARYSPRMLRWAH (SEQ ID No. 70) |
| y-Her.C2.P4.2-20 | YGTDD (SEQ ID No. 50) | ARYSPRMLRWAR (SEQ ID No. 71) |

Example 7

Yeast Display of 4D5 Fab

For the display of a Fab fragment on yeast, the yeast display vector pYD1 (Invitrogen) (SEQ ID No. 72) is modified as follows:

A NheI restriction site is introduced by site directed mutagenesis at position 581/586 to yield the modified vector pYD1Nhe (SEQ ID No. 73). This vector is restricted with NheI and PmeI, to yield 3 fragments. The largest fragment is the remaining vector backbone, in which a synthetic oligonucleotide linker is inserted to yield the vector pYD1lnk (SEQ ID No. 74). A cassette which includes the MATα transcription termination region is then amplified by PCR from the vector pYD1 and is cloned into pYD1lnk via BamHI and PstI restriction and ligation. The resulting vector is pYD1mata (SEQ ID No. 75). A cassette that contains the GAL1 promoter, the gene coding for Aga2 and a synthetic linker with NotI and SfiI cloning sites is amplified by PCR from pYD1 and cloned in pYD1mata via EcoRI and PacI restriction to yield the vector pYD1gal (SEQ.ID No. 76).

As an example for a Fab to be displayed on yeast, the genes coding for VH-CH1 and VL-CL respectively of the antibody 4D5 (Herceptin) are made synthetically (sequences 4D5H (SEQ ID No. 77) and 4D5L (SEQ ID No. 78)).

4D5H is flanked by SfiI and NotI restriction sites, and cloned into the vector pYD1gal to yield the vector pYD4D5hc (SEQ ID No. 79). In this vector, the N-terminus of 4D5H is fused to the C-terminus of Aga2, and at the C-terminus of 4D5H, a hexahistidine tag is attached, followed by the stop codon. The amino acid sequence of VH-CH1 of 4D5 is given in 4D5hp (SEQ ID No. 80).

4D5L is flanked by NcoI and AscI restriction sites, and cloned into the vector pYD4D5hc to yield the vector pYD4D5hl (SEQ ID No. 81). 4D5L is preceded by an Aga2 secretion signal, and carries a stop codon after the C-terminal Cysteine residue of the CL domain. The amino acid sequence of VL-CL of 4D5 is given in 4D5lp (SEQ ID No. 82).

For display of the 4D5 Fab, the vector pYD4D5hl is transformed into the yeast strain EBY100 (Invitrogen), transformants are selected on minimal medium without tryptophan, and expression of the recombinant protein is induced by growth on galactose containing medium according to standard protocols (Invitrogen).

Example 8

Construction of a Library with Randomized Residues in Structural Loops of the CL Domain of 4D5 Fab As first step in the yeast display library construction, the wildtype CL (C kappa) domain is cut out from the display vector pYD4D5hl with restriction enzymes BsiWI and AscI. A synthetic gene encoding human C kappa domain flanked by BsiWI and AscI sites (in the context according to pYD4D5hl) is prepared in which random mutations and insertions respectively are introduced in the AB and EF loops. In this particular example, insertions of 3, 4 or 5 NNB codons are made between amino acid positions 16 and 17 of the human C kappa domain, and residue positions 92, 93, 94, 95, 97, 98 and 99 are replaced by NNB codons. (IMGT numbering, see FIG. 2). An NNB codon contains all 4 nucleotides at positions 1 and 2, and C, G and T at position 3. NNB therefore encodes all 20 naturally encoded amino acids.

The library is prepared and selected following standard procedures.

As a scaffold ligand the CDR target Her2neu and 4D5 epitope is used. Those members of the library are selected for production of a cytotoxic modular antibody according to the invention, that have a binding site engineered into the CL domain, which is specifically binding to an effector molecule, such as an Fcgamma receptor, or a half-life prolonging protein, such as serum albumin. The resulting Fab is tested for (i) Her2neu binding with a Kd<$10^{-8}$ M and an IC50<$10^{-8}$ M, and (ii) effector function using a CDC and/or ADCC assay, and alternatively to determine albumin binding.

The invention claimed is:

1. A method of producing a functional binding agent, wherein the functional binding agent binds to a target antigen, wherein the functional binding agent is an antibody Fc fragment consisting of a CH2 domain and a CH3 domain, comprising the steps of:
   a) providing a library of said antibody Fc fragments,
   b) contacting said library with said target antigen in the presence of a scaffold ligand, wherein said target antigen and said scaffold ligand are different molecules, wherein said scaffold ligand is selected from the group consisting of CD64, CD16, CD32, FcRn and Protein A,
   c) selecting a library member binding to said target antigen in the presence of said scaffold ligand to obtain a functional binding agent, and
   d) producing a preparation of the functional binding agent.

2. The method of claim 1, wherein said library contains at least $10^2$ independent clones expressing functional binding agents.

3. The method of claim 1, wherein the functional binding agent has a target binding affinity of $Kd<10^{-8}M$.

4. The method of claim 1, wherein said target antigen is a receptor of the erbB class.

5. The method of claim 1, further comprising the steps of:
   e) affinity maturating the functional binding agent by amino acid variation to obtain an affinity matured pool of binding agents, and
   f) selecting a member of said pool which binds to the target antigen in the presence of the scaffold ligand to obtain an affinity matured functional binding agent.

6. The method of claim 5, wherein the affinity matured functional binding agent exhibits at least a 10 fold increase in affinity of binding to the target antigen compared to the functional binding agent.

* * * * *

SEQUENCE LISTING

```
<160> NUMBER OF SEQ ID NOS: 88

<210> SEQ ID NO 1
<211> LENGTH: 232
<212> TYPE: PRT
<213> ORGANISM: human

<400> SEQUENCE: 1

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 2
<211> LENGTH: 237
<212> TYPE: PRT
<213> ORGANISM: artificial
<220> FEATURE:
<223> OTHER INFORMATION: human IgG including randomized amino acid
      modifications
<220> FEATURE:
<221> NAME/KEY: misc_feature
<222> LOCATION: (144)..(146)
<223> OTHER INFORMATION: Xaa can be any naturally occurring amino acid
<220> FEATURE:
<221> NAME/KEY: misc_feature
<222> LOCATION: (198)..(205)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Xaa
130                 135                 140

Xaa Xaa Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Xaa Xaa Xaa Xaa Xaa Xaa Xaa Xaa Arg Trp Xaa
        195                 200                 205

Xaa Gly Asn

<210> SEQ ID NO 3
<211> LENGTH: 728
<212> TYPE: DNA
<213> ORGANISM: artificial
<220> FEATURE:
<223> OTHER INFORMATION: DNA Sequence for Cloning of modified IgG
<220> FEATURE:
<221> NAME/KEY: misc_feature
<222> LOCATION: (438)..(439)
<223> OTHER INFORMATION: n is a, c, g, or t
<220> FEATURE:
<221> NAME/KEY: misc_feature
<222> LOCATION: (441)..(442)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t
<220> FEATURE:
<221> NAME/KEY: misc_feature
<222> LOCATION: (600)..(601)
<223> OTHER INFORMATION: n is a, c, g, or t
<220> FEATURE:
<221> NAME/KEY: misc_feature
<222> LOCATION: (603)..(604)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (609)..(610)
<223> OTHER INFORMATION: n is a, c, g, or t
<220> FEATURE:
<221> NAME/KEY: misc_feature
<222> LOCATION: (612)..(613)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (618)..(619)
<223> OTHER INFORMATION: n is a, c, g, or t
<220> FEATURE:
<221> NAME/KEY: misc_feature
<222> LOCATION: (621)..(622)
<223> OTHER INFORMATION: n is a, c, g, or t
<220> FEATURE:
<221> NAME/KEY: misc_feature
<222> LOCATION: (630)..(631)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t

<400> SEQUENCE: 3

```
ccatggccga gcccaaatct tgtgacaaaa ctcacacatg cccaccgtgc ccagcacctg      60
aactcctggg gggaccgtca gtcttcctct tccccccaaa acccaaggac accctcatga     120
tctcccggac ccctgaggtc acatgcgtgg tggtggacgt gagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca gcccccatcg     360
agaaaaccat ctccaaagcc aaagggcagc ctcgagaacc acaggtgtac accctgcccc     420
catcccgtga cgagctcnns nnsnnscaag tcagcctgac ctgcctggtc aaaggcttct     480
```

```
atcccagcga catcgccgtg gagtgggaga gcaatgggca gccggagaac aactacaaga    540
ccacgcctcc cgtgctggac tccgacggct ccttcttcct ctacagcaag cttaccgtgn    600
nsnnsnnsnn snnsnnsnns nnsaggtggn nsnnsgggaa cgtcttctca tgctccgtga    660
tgcatgaggc tctgcacaac cactacacac agaagagcct ctccctgtct ccgggtaaag    720
cggccgca                                                             728

<210> SEQ ID NO 4
<211> LENGTH: 33
<212> TYPE: DNA
<213> ORGANISM: artificial
<220> FEATURE:
<223> OTHER INFORMATION: PCR primer EPKSNCO

<400> SEQUENCE: 4
ccatggccga gcccaaatct tgtgacaaaa ctc                                  33

<210> SEQ ID NO 5
<211> LENGTH: 30
<212> TYPE: DNA
<213> ORGANISM: artificial
<220> FEATURE:
<223> OTHER INFORMATION: PCR primer CH3LSAC

<400> SEQUENCE: 5
agtcgagctc gtcacgggat gggggcaggg                                     30

<210> SEQ ID NO 6
<211> LENGTH: 41
<212> TYPE: DNA
<213> ORGANISM: artificial
<220> FEATURE:
<223> OTHER INFORMATION: PCR primer CH3CSAC
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 6
gtacgagctc nnsnnsnnsc aagtcagcct gacctgcctg g                        41

<210> SEQ ID NO 7
<211> LENGTH: 32
<212> TYPE: DNA
<213> ORGANISM: artificial
<220> FEATURE:
<223> OTHER INFORMATION: PCR primer CH3CHIN

<400> SEQUENCE: 7
tgccaagctt gctgtagagg aagaaggagc cg                                  32

<210> SEQ ID NO 8
<211> LENGTH: 59
<212> TYPE: DNA
<213> ORGANISM: artificial
<220> FEATURE:
<223> OTHER INFORMATION: PCR primer CH3RHIN
<220> FEATURE:
<221> NAME/KEY: misc_feature
```

```
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 8
tgccaagctt accgtgnnsn nsnnsaggtg gnnsnnsggg aacgtcttct catgctccg      59

<210> SEQ ID NO 9
<211> LENGTH: 33
<212> TYPE: DNA
<213> ORGANISM: artificial
<220> FEATURE:
<223> OTHER INFORMATION: PCR primer CH3RNOT

<400> SEQUENCE: 9
agttgcggcc gctttacccg gagacaggga gag                                 33

<210> SEQ ID NO 10
<211> LENGTH: 25
<212> TYPE: PRT
<213> ORGANISM: artificial
<220> FEATURE:
<223> OTHER INFORMATION: junction region

<400> SEQUENCE: 10

Ser Pro Gly Lys Ala Ala Ala Glu Gln Lys Leu Ile Ser Glu Glu Asp
1               5                   10                  15

Leu Asn Gly Ala Ala Thr Val Glu Ser
            20                  25

<210> SEQ ID NO 11
<211> LENGTH: 662
<212> TYPE: PRT
<213> ORGANISM: artificial
<220> FEATURE:
<223> OTHER INFORMATION: amino acid sequence of FcabRGD4L

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Gly Cys Arg Gly Asp Cys Leu Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys Glu Gly Gly
225                 230                 235                 240

Gly Ser Ala Ala Ala Glu Gln Lys Leu Ile Ser Glu Glu Asp Leu Asn
                245                 250                 255

Gly Ala Ala Thr Val Glu Ser Cys Leu Ala Lys Pro His Thr Glu Asn
            260                 265                 270

Ser Phe Thr Asn Val Trp Lys Asp Asp Lys Thr Leu Asp Arg Tyr Ala
        275                 280                 285

Asn Tyr Glu Gly Cys Leu Trp Asn Ala Thr Gly Val Val Val Cys Thr
    290                 295                 300

Gly Asp Glu Thr Gln Cys Tyr Gly Thr Trp Val Pro Ile Gly Leu Ala
305                 310                 315                 320

Ile Pro Glu Asn Glu Gly Gly Ser Glu Gly Gly Ser Glu Gly
                325                 330                 335

Gly Gly Ser Glu Gly Gly Thr Lys Pro Pro Glu Tyr Gly Asp Thr
            340                 345                 350

Pro Ile Pro Gly Tyr Thr Tyr Ile Asn Pro Leu Asp Gly Thr Tyr Pro
        355                 360                 365

Pro Gly Thr Glu Gln Asn Pro Ala Asn Pro Asn Pro Ser Leu Glu Glu
    370                 375                 380

Ser Gln Pro Leu Asn Thr Phe Met Phe Gln Asn Asn Arg Phe Arg Asn
385                 390                 395                 400

Arg Gln Gly Ala Leu Thr Val Tyr Thr Gly Thr Val Thr Gln Gly Thr
                405                 410                 415

Asp Pro Val Lys Thr Tyr Tyr Gln Tyr Thr Pro Val Ser Ser Lys Ala
            420                 425                 430

Met Tyr Asp Ala Tyr Trp Asn Gly Lys Phe Arg Asp Cys Ala Phe His
        435                 440                 445

Ser Gly Phe Asn Glu Asp Pro Phe Val Cys Glu Tyr Gln Gly Gln Ser
    450                 455                 460

Ser Asp Leu Pro Gln Pro Pro Val Asn Ala Gly Gly Ser Gly Gly
465                 470                 475                 480

Gly Ser Gly Gly Gly Ser Glu Gly Gly Ser Glu Gly Gly Ser
                485                 490                 495

Glu Gly Gly Gly Ser Glu Gly Gly Ser Gly Gly Ser Gly Ser
            500                 505                 510

Gly Asp Phe Asp Tyr Glu Lys Met Ala Asn Ala Asn Lys Gly Ala Met
```

-continued

```
                     515                 520                 525
Thr Glu Asn Ala Asp Glu Asn Ala Leu Gln Ser Asp Ala Lys Gly Lys
    530                 535                 540

Leu Asp Ser Val Ala Thr Asp Tyr Gly Ala Ala Ile Asp Gly Phe Ile
545                 550                 555                 560

Gly Asp Val Ser Gly Leu Ala Asn Gly Asn Gly Ala Thr Gly Asp Phe
                565                 570                 575

Ala Gly Ser Asn Ser Gln Met Ala Gln Val Gly Asp Gly Asp Asn Ser
            580                 585                 590

Pro Leu Met Asn Asn Phe Arg Gln Tyr Leu Pro Ser Leu Pro Gln Ser
        595                 600                 605

Val Glu Cys Arg Pro Tyr Val Phe Gly Ala Gly Lys Pro Tyr Glu Phe
    610                 615                 620

Ser Ile Asp Cys Asp Lys Ile Asn Leu Phe Arg Gly Val Phe Ala Phe
625                 630                 635                 640

Leu Leu Tyr Val Ala Thr Phe Met Tyr Val Phe Ser Thr Phe Ala Asn
                645                 650                 655

Ile Leu His Lys Glu Ser
            660
```

<210> SEQ ID NO 12
<211> LENGTH: 5200
<212> TYPE: DNA
<213> ORGANISM: artificial
<220> FEATURE:
<223> OTHER INFORMATION: vector pHENFcabRGD4

<400> SEQUENCE: 12

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt tgccttcct gtttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga ccaccgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc attttttaatt taaaaggatc taggtgaaga    1140
tcctttttga taatctcatg accaaaatcc cttaacgtga gttttcgttc cactgagcgt    1200
```

```
cagaccccgt agaaaagatc aaaggatctt cttgagatcc ttttttttctg cgcgtaatct    1260
gctgcttgca aacaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg atttttgtga tgctcgtcag    1800
gggggcggag cctatggaaa aacgccagca acgcggcctt tttacggttc ctggccttttt   1860
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt aagcttgcat gcaaattcta tttcaaggag acagtcataa    2280
tgaaatacct attgcctacg gcagccgctg gattgttatt actcgcggcc cagccggcca    2340
tggccgagcc caaatcttgt gacaaaactc acacatgccc accgtgccca gcacctgaac    2400
tcctgggggg accgtcagtc ttcctcttcc ccccaaaacc caaggacacc ctcatgatct    2460
cccggacccc tgaggtcaca tgcgtggtgg tggacgtgag ccacgaagac cctgaggtca    2520
agttcaactg gtacgtggac ggcgtggagg tgcataatgc caagacaaag ccgcgggagg    2580
agcagtacaa cagcacgtac cgtgtggtca gcgtcctcac cgtcctgcac caggactggc    2640
tgaatggcaa ggagtacaag tgcaaggtct ccaacaaagc cctcccagcc cccatcgaga    2700
aaaccatctc caaagccaaa gggcagcccc gagaaccaca ggtgtacacc ctgccccca    2760
cccgggatga gctgaccaag aaccaggtca gcctgacctg cctggtcaaa ggcttctatc    2820
ccagcgacat cgccgtggag tgggagagca atgggcagcc ggagaacaac tacaagacca    2880
cgcctcccgt gctggactcc gacggctcct tcttcctcta cagcaagctt accgtggggtt   2940
gccgcggtga ttgtctgagc aggtggcagc aggggaacgt cttctcatgc tccgtgatgc    3000
atgaggctct gcacaaccac tacacgcaga agagcctctc cctgtctccg ggtaaagcgg    3060
ccgcagaaca aaaactcatc tcagaagagg atctgaatgg ggccgcatag actgttgaaa    3120
gttgtttagc aaaaccctca tacagaaaatt catttactaa cgtctggaaa gacgacaaaa    3180
ctttagatcg ttacgctaac tatgagggct gtctgtggaa tgctacaggc gttgtggttt    3240
gtactggtga cgaaactcag tgttacggta catgggttcc tattgggctt gctatccctg    3300
aaaatgaggg tggtggctct gagggtggcg gttctgaggg tggcggttct gagggtggcg    3360
gtactaaacc tcctgagtac ggtgatacac ctattccggg ctatacttat atcaaccctc    3420
tcgacggcac ttatccgcct ggtactgagc aaaaccccgc taatcctaat ccttctcttg    3480
aggagtctca gcctcttaat actttcatgt ttcagaataa taggttccga aataggcagg    3540
gtgcattaac tgtttatacg ggcactgtta ctcaaggcac tgaccccgtt aaaacttatt    3600
```

| | |
|---|---|
| accagtacac tcctgtatca tcaaaagcca tgtatgacgc ttactggaac ggtaaattca | 3660 |
| gagactgcgc tttccattct ggctttaatg aggatccatt cgtttgtgaa tatcaaggcc | 3720 |
| aatcgtctga cctgcctcaa cctcctgtca atgctggcgg cggctctggt ggtggttctg | 3780 |
| gtggcggctc tgagggtggc ggctctgagg gtggcggttc tgagggtggc ggctctgagg | 3840 |
| gtggcggttc cggtggcggc tccggttccg gtgattttga ttatgaaaaa atggcaaacg | 3900 |
| ctaataaggg ggctatgacc gaaaatgccg atgaaaacgc gctacagtct gacgctaaag | 3960 |
| gcaaacttga ttctgtcgct actgattacg gtgctgctat cgatggtttc attggtgacg | 4020 |
| tttccggcct tgctaatggt aatggtgcta ctggtgattt tgctggctct aattcccaaa | 4080 |
| tggctcaagt cggtgacggt gataattcac ctttaatgaa taatttccgt caatatttac | 4140 |
| cttctttgcc tcagtcggtt gaatgtcgcc cttatgtctt tggcgctggt aaaccatatg | 4200 |
| aattttctat tgattgtgac aaaataaact tattccgtgg tgtctttgcg tttcttttat | 4260 |
| atgttgccac ctttatgtat gtattttcga cgtttgctaa catactgcat aaggagtctt | 4320 |
| aataagaatt cactggccgt cgttttacaa cgtcgtgact gggaaaaccc tggcgttacc | 4380 |
| caacttaatc gccttgcagc acatcccct ttcgccagct ggcgtaatag cgaagaggcc | 4440 |
| cgcaccgatc gcccttccca cagttgcgc agcctgaatg gcgaatggcg cctgatgcgg | 4500 |
| tattttctcc ttacgcatct gtgcggtatt tcacaccgca cgtcaaagca accatagtac | 4560 |
| gcgccctgta gcggcgcatt aagcgcggcg ggtgtggtgg ttacgcgcag cgtgaccgct | 4620 |
| acacttgcca gcgccctagc gcccgctcct ttcgctttct tcccttcctt tctcgccacg | 4680 |
| ttcgccggct ttccccgtca agctctaaat cgggggctcc ctttagggtt ccgatttagt | 4740 |
| gctttacggc acctcgaccc caaaaaactt gatttgggtg atggttcacg tagtgggcca | 4800 |
| tcgccctgat agacggtttt tcgccctttg acgttggagt ccacgttctt taatagtgga | 4860 |
| ctcttgttcc aaactggaac aacactcaac cctatctcgg gctattcttt tgatttataa | 4920 |
| gggattttgc cgatttcggc ctattggtta aaaaatgagc tgatttaaca aaaatttaac | 4980 |
| gcgaatttta caaaatatt aacgtttaca attttatggt gcactctcag tacaatctgc | 5040 |
| tctgatgccg catagttaag ccagccccga cacccgccaa cacccgctga cgcgccctga | 5100 |
| cgggcttgtc tgctcccggc atccgcttac agacaagctg tgaccgtctc cgggagctgc | 5160 |
| atgtgtcaga ggttttcacc gtcatcaccg aaacgcgcga | 5200 |

```
<210> SEQ ID NO 13
<211> LENGTH: 48
<212> TYPE: DNA
<213> ORGANISM: artificial
<220> FEATURE:
<223> OTHER INFORMATION: CH3rlink

<400> SEQUENCE: 13
```

| | |
|---|---|
| actagcggcc gcagagccac caccctcctt acccggagac agggagag | 48 |

```
<210> SEQ ID NO 14
<211> LENGTH: 5215
<212> TYPE: DNA
<213> ORGANISM: artificial
<220> FEATURE:
<223> OTHER INFORMATION: vector pHENFcabRGD4L

<400> SEQUENCE: 14
```

| | |
|---|---|
| gacgaaaggg cctcgtgata cgcctatttt tataggttaa tgtcatgata ataatggttt | 60 |

| | |
|---|---|
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc atttttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca acaaaaaaa ccaccgctac cagcggtggt ttgtttgccg gatcaagagc | 1320 |
| taccaactct ttttccgaag gtaactggct tcagcagagc gcagatacca aatactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg tcgggctga acggggggtt | 1560 |
| cgtgcacaca gcccagcttg gagcgaacga cctacaccga actgagatac ctacagcgtg | 1620 |
| agcattgaga aagcgccacg cttcccgaag ggagaaaggc ggacaggtat ccggtaagcg | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttgtga tgctcgtcag | 1800 |
| gggggcggag cctatggaaa aacgccagca acgcggcctt tttacggttc ctggccttt | 1860 |
| gctggccttt tgctcacatg ttctttcctg cgttatcccc tgattctgtg ataaccgta | 1920 |
| ttaccgcctt tgagtgagct gataccgctc gccgcagccg aacgaccgag cgcagcgagt | 1980 |
| cagtgagcga ggaagcggaa gagcgcccaa tacgcaaacc gcctctcccc gcgcgttggc | 2040 |
| cgattcatta atgcagctgg cacgacaggt ttcccgactg gaaagcgggc agtgagcgca | 2100 |
| acgcaattaa tgtgagttag ctcactcatt aggcaccca ggctttacac tttatgcttc | 2160 |
| cggctcgtat gttgtgtgga attgtgagcg ataacaatt tcacacagga aacagctatg | 2220 |
| accatgatta cgccaagctt aagcttgcat gcaaattcta tttcaaggag acagtcataa | 2280 |
| tgaaatacct attgcctacg gcagccgctg gattgttatt actcgcggcc cagccggcca | 2340 |
| tggccgagcc caaatcttgt gacaaaactc acacatgccc accgtgccca gcacctgaac | 2400 |
| tcctgggggg accgtcagtc ttcctcttcc ccccaaaacc caaggacacc ctcatgatct | 2460 |

```
cccggacccc tgaggtcaca tgcgtggtgg tggacgtgag ccacgaagac cctgaggtca   2520
agttcaactg gtacgtggac ggcgtggagg tgcataatgc caagacaaag ccgcgggagg   2580
agcagtacaa cagcacgtac cgtgtggtca gcgtcctcac cgtcctgcac caggactggc   2640
tgaatggcaa ggagtacaag tgcaaggtct ccaacaaagc cctcccagcc cccatcgaga   2700
aaaccatctc caaagccaaa gggcagcccc gagaaccaca ggtgtacacc ctgcccccat   2760
cccgggatga gctgaccaag aaccaggtca gcctgacctg cctggtcaaa ggcttctatc   2820
ccagcgacat cgccgtggag tgggagagca atgggcagcc ggagaacaac tacaagacca   2880
cgcctcccgt gctggactcc gacggctcct tcttcctcta cagcaagctt accgtgggtt   2940
gccgcggtga ttgtctgagc aggtggcagc aggggaacgt cttctcatgc tccgtgatgc   3000
atgaggctct gcacaaccac tacacgcaga agagcctctc cctgtctccg ggtaaggagg   3060
gtggtggctc tgcggccgca gaacaaaaac tcatctcaga gaggatctg aatggggccg   3120 catagactgt tgaaagttgt ttagcaaaac ctcatacaga aaattcattt actaacgtct   3180
ggaaagacga caaaacttta gatcgttacg ctaactatga gggctgtctg tggaatgcta   3240
caggcgttgt ggtttgtact ggtgacgaaa ctcagtgtta cggtacatgg gttcctattg   3300
ggcttgctat ccctgaaaat gagggtggtg gctctgaggg tggcggttct gagggtggcg   3360
gttctgaggg tggcggtact aaacctcctg agtacggtga tacacctatt ccgggctata   3420
cttatatcaa ccctctcgac ggcacttatc cgcctggtac tgagcaaaac cccgctaatc   3480
ctaatccttc tcttgaggag tctcagcctc ttaatacttt catgtttcag aataataggt   3540
tccgaaatag cagggtgca ttaactgttt atacgggcac tgttactcaa ggcactgacc   3600
ccgttaaaac ttattaccag tacactcctg tatcatcaaa agccatgtat gacgcttact   3660
ggaacggtaa attcagagac tgcgctttcc attctggctt taatgaggat ccattcgttt   3720
gtgaatatca aggccaatcg tctgacctgc ctcaacctcc tgtcaatgct ggcggcggct   3780
ctggtggtgg ttctggtggc ggctctgagg gtggcggctc tgagggtggc ggttctgagg   3840
gtggcggctc tgagggtggc ggttccggtg gcggctccgg ttccggtgat tttgattatg   3900
aaaaaatggc aaacgctaat aagggggcta tgaccgaaaa tgccgatgaa aacgcgctac   3960
agtctgacgc taaaggcaaa cttgattctg tcgctactga ttacggtgct gctatcgatg   4020
gtttcattgg tgacgtttcc ggccttgcta atggtaatgg tgctactggt gattttgctg   4080
gctctaattc ccaaatggct caagtcggtg acggtgataa ttcaccttta atgaataatt   4140
tccgtcaata tttaccttct ttgcctcagt cggttgaatg tcgcccttat gtctttggcg   4200
ctggtaaacc atatgaattt tctattgatt gtgacaaaat aaacttattc cgtggtgtct   4260
ttgcgtttct tttatatgtt gccaccttta tgtatgtatt ttcgacgttt gctaacatac   4320
tgcataagga gtcttaataa gaattcactg gccgtcgttt tacaacgtcg tgactgggaa   4380
aaccctggcg ttacccaact taatcgcctt gcagcacatc cccctttcgc cagctggcgt   4440
aatagcgaag aggcccgcac cgatcgccct tcccaacagt tgcgcagcct gaatggcgaa   4500
tggcgcctga tgcggtattt tctccttacg catctgtgcg gtatttcaca ccgcacgtca   4560
aagcaaccat agtacgcgcc ctgtagcggc gcattaagcg cggcgggtgt ggtggttacg   4620
cgcagcgtga ccgctacact tgccagcgcc ctagcgcccg ctcctttcgc tttcttccct   4680
tcctttctcg ccacgttcgc cggctttccc cgtcaagctc taaatcgggg gctcccttta   4740
gggttccgat ttagtgcttt acggcacctc gaccccaaaa aacttgattt gggtgatggt   4800
```

| | |
|---|---|
| tcacgtagtg ggccatcgcc ctgatagacg gtttttcgcc ctttgacgtt ggagtccacg | 4860 |
| ttctttaata gtggactctt gttccaaact ggaacaacac tcaaccctat ctcgggctat | 4920 |
| tcttttgatt tataagggat tttgccgatt tcggcctatt ggttaaaaaa tgagctgatt | 4980 |
| taacaaaaat ttaacgcgaa ttttaacaaa atattaacgt ttacaatttt atggtgcact | 5040 |
| ctcagtacaa tctgctctga tgccgcatag ttaagccagc ccgacaccc gccaacaccc | 5100 |
| gctgacgcgc cctgacgggc ttgtctgctc ccggcatccg cttacagaca agctgtgacc | 5160 |
| gtctccggga gctgcatgtg tcagaggttt tcaccgtcat caccgaaacg cgcga | 5215 |

<210> SEQ ID NO 15
<211> LENGTH: 5013
<212> TYPE: DNA
<213> ORGANISM: artificial
<220> FEATURE:
<223> OTHER INFORMATION: vector pYD1dX

<400> SEQUENCE: 15

| | |
|---|---|
| acggattaga agccgccgag cgggtgacag ccctccgaag gaagactctc ctccgtgcgt | 60 |
| cctcgtcttc accggtcgcg ttcctgaaac gcagatgtgc ctcgcgccgc actgctccga | 120 |
| acaataaaga ttctacaata ctagctttta tggttatgaa gaggaaaaat tggcagtaac | 180 |
| ctggccccac aaaccttcaa atgaacgaat caaattaaca accataggat gataatgcga | 240 |
| ttagtttttt agccttattt ctggggtaat taatcagcga agcgatgatt tttgatctat | 300 |
| taacagatat ataaatgcaa aaactgcata accactttaa ctaatacttt caacattttc | 360 |
| ggtttgtatt acttcttatt caatgtaat aaaagtatca acaaaaaatt gttaatatac | 420 |
| ctctatactt taacgtcaag gagaaaaaac cccggatcgg actactagca gctgtaatac | 480 |
| gactcactat agggaatatt aagctaattc tacttcatac attttcaatt aagatgcagt | 540 |
| tacttcgctg ttttttcaata ttttctgtta ttgcttcagt tttagcacag gaactgacaa | 600 |
| ctatatgcga gcaaatcccc tcaccaactt tagaatcgac gccgtactct ttgtcaacga | 660 |
| ctactatttt ggccaacggg aaggcaatgc aaggagtttt tgaatattac aaatcagtaa | 720 |
| cgtttgtcag taattgcggt tctcaccct caacaactag caaaggcagc ccataaaaca | 780 |
| cacagtatgt ttttaagctt ctgcaggcta gtggtggtgg tggttctggt ggtggtggtt | 840 |
| ctggtggtgg tggttctgct agcatgactg gtggacagca aatgggtcgg gatctgtacg | 900 |
| acgatgacga taaggtacca ggatccagtg tggtggaatt ctgcagatat ccagcacagt | 960 |
| ggcggccgct cgatcgagtc tagagggccc ttcgaaggta agcctatccc taaccctctc | 1020 |
| ctcggtctcg attctacgcg taccggtcat catcaccatc accattgagt ttaaacccgc | 1080 |
| tgatctgata acaacagtgt agatgtaaca aaatcgactt tgttcccact gtactttag | 1140 |
| ctcgtacaaa atacaatata cttttcattt ctccgtaaac aacatgtttt cccatgtaat | 1200 |
| atcctttct attttcgtt ccgttaccaa ctttacacat actttatata gctattcact | 1260 |
| tctatacact aaaaaactaa gacaatttta attttgctgc ctgccatatt tcaatttgtt | 1320 |
| ataaattcct ataatttatc ctattagtag ctaaaaaaag atgaatgtga atcgaatcct | 1380 |
| aagagaattg ggcaagtgca caaacaatac ttaaataaat actactcagt aataacctat | 1440 |
| ttcttagcat ttttgacgaa atttgctatt tgttagagt cttttacacc atttgtctcc | 1500 |
| acacctccgc ttcatcaac accaataacg ccatttaatc taagcgcatc accaacattt | 1560 |
| tctggcgtca gtccaccagc taacataaaa tgtaagctct cggggctctc ttgccttcca | 1620 |
| acccagtcag aaatcgagtt ccaatccaaa agttcacctg tcccacctgc ttctgaatca | 1680 |

```
aacaagggaa taaacgaatg aggtttctgt gaagctgcac tgagtagtat gttgcagtct    1740
tttggaaata cgagtctttt aataactggc aaaccgagga actcttggta ttcttgccac    1800
gactcatctc cgtgcagttg gacgatatca atgccgtaat cattgaccag agccaaaaca    1860
tcctccttag gttgattacg aaacacgcca accaagtatt tcggagtgcc tgaactattt    1920
ttatatgctt ttacaagact tgaaattttc cttgcaataa ccgggtcaat tgttctcttt    1980
ctattgggca cacatataat acccagcaag tcagcatcgg aatctagagc acattctgcg    2040
gcctctgtgc tctgcaagcc gcaaactttc accaatggac cagaactacc tgtgaaatta    2100
ataacagaca tactccaagc tgcctttgtg tgcttaatca cgtatactca cgtgctcaat    2160
agtcaccaat gccctccctc ttggccctct ccttttcttt tttcgaccga atttcttgaa    2220
gacgaaaggg cctcgtgata cgcctatttt tataggttaa tgtcatgata taatggtttt    2280
cttaggacgg atcgcttgcc tgtaacttac acgcgcctcg tatcttttaa tgatggaata    2340
atttgggaat ttactctgtg tttatttatt tttatgtttt gtatttggat tttagaaagt    2400
aaataaagaa ggtagaagag ttacggaatg aagaaaaaaa aataaacaaa ggtttaaaaa    2460
atttcaacaa aaagcgtact ttacatatat atttattaga caagaaaagc agattaaata    2520
gatatacatt cgattaacga taagtaaaat gtaaaatcac aggattttcg tgtgtggtct    2580
tctacacaga caagatgaaa caattcggca ttaatacctg agagcaggaa gagcaagata    2640
aaaggtagta tttgttggcg atcccccctag agtcttttac atcttcggaa aacaaaaact    2700
attttttctt taatttcttt ttttactttc tattttaat ttatatattt atattaaaaa    2760
atttaaatta taattatttt tatagcacgt gatgaaaagg acccaggtgg cacttttcgg    2820
ggaaatgtgc gcggaacccc tatttgttta tttttctaaa tacattcaaa tatgtatccg    2880
ctcatgagac aataaccctg ataaatgctt caataatatt gaaaaggaa gagtatgagt    2940 attcaacatt tccgtgtcgc ccttattccc ttttttgcgg catttttgcct tcctgttttt    3000 gctcacccag aaacgctggt gaaagtaaaa gatgctgaag atcagttggg tgcacgagtg    3060
ggttacatcg aactggatct caacagcggt aagatccttg agagttttcg ccccgaagaa    3120
cgttttccaa tgatgagcac ttttaaagtt ctgctatgtg gcgcggtatt atcccgtgtt    3180
gacgccgggc aagagcaact cggtcgccgc atacactatt ctcagaatga cttggttgag    3240
tactcaccag tcacagaaaa gcatcttacg gatggcatga cagtaagaga attatgcagt    3300
gctgccataa ccatgagtga taacactgcg gccaacttac ttctgacaac gatcggagga    3360
ccgaaggagc taaccgcttt tttgcacaac atggggatc atgtaactcg ccttgatcgt    3420
tgggaaccgg agctgaatga agccatacca aacgacgagc gtgacaccac gatgcctgta    3480
gcaatggcaa caacgttgcg caaactatta actggcgaac tacttactct agcttcccgg    3540
caacaattaa tagactggat ggaggcggat aaagttgcag gaccacttct gcgctcggcc    3600
cttccggctg gctggtttat tgctgataaa tctggagccg gtgagcgtgg gtctcgcggt    3660
atcattgcag cactggggcc agatggtaag ccctcccgta tcgtagttat ctacacgacg    3720
ggcagtcagg caactatgga tgaacgaaat agacagatcg ctgagatagg tgcctcactg    3780
attaagcatt ggtaactgtc agaccaagtt tactcatata tactttagat tgatttaaaa    3840
cttcattttt aatttaaaag gatctaggtg aagatccttt ttgataatct catgaccaaa    3900
atcccttaac gtgagttttc gttccactga gcgtcagacc ccgtagaaaa gatcaaagga    3960
tcttcttgag atcctttttt tctgcgcgta atctgctgct tgcaaacaaa aaaaccaccg    4020
```

```
ctaccagcgg tggtttgttt gccggatcaa gagctaccaa ctcttttcc gaaggtaact      4080
ggcttcagca gagcgcagat accaaatact gtccttctag tgtagccgta gttaggccac      4140
cacttcaaga actctgtagc accgcctaca tacctcgctc tgctaatcct gttaccagtg      4200
gctgctgcca gtggcgataa gtcgtgtctt accgggttgg actcaagacg atagttaccg      4260
gataaggcgc agcggtcggg ctgaacgggg ggttcgtgca cacagcccag cttggagcga      4320
acgacctaca ccgaactgag atacctacag cgtgagcatt gagaaagcgc cacgcttccc      4380
gaagggagaa aggcggacag gtatccggta agcggcaggg tcggaacagg agagcgcacg      4440
agggagcttc cagggggaa cgcctggtat ctttatagtc ctgtcgggtt cgccacctc       4500
tgacttgagc gtcgattttt gtgatgctcg tcagggggc cgagcctatg gaaaaacgcc      4560
agcaacgcgg ccttttacg gttcctggcc ttttgctggc cttttgctca catgttcttt       4620
cctgcgttat cccctgattc tgtggataac cgtattaccg cctttgagtg agctgatacc      4680
gctcgccgca gccgaacgac cgagcgcagc gagtcagtga gcgaggaagc ggaagagcgc      4740
ccaatacgca aaccgcctct ccccgcgcgt tggccgattc attaatgcag ctggcacgac      4800
aggtttcccg actggaaagc gggcagtgag cgcaacgcaa ttaatgtgag ttacctcact      4860
cattaggcac cccaggcttt acactttatg cttccggctc ctatgttgtg tggaattgtg      4920
agcggataac aatttcacac aggaaacagc tatgaccatg attacgccaa gctcggaatt      4980
aaccctcact aaagggaaca aaagctggct agt                                  5013

<210> SEQ ID NO 16
<211> LENGTH: 5971
<212> TYPE: DNA
<213> ORGANISM: artificial
<220> FEATURE:
<223> OTHER INFORMATION: vector pYD1dXFc
<400> SEQUENCE: 16
acggattaga agccgccgag cgggtgacag ccctccgaag gaagactctc ctccgtgcgt        60
cctcgtcttc accggtcgcg ttcctgaaac gcagatgtgc ctcgcgccgc actgctccga       120
acaataaaga ttctacaata ctagctttta tggttatgaa gaggaaaaat tggcagtaac       180
ctggccccac aaaccttcaa atgaacgaat caaattaaca accataggat gataatgcga       240
ttagtttttt agccttattt ctgggtaat taatcagcga agcgatgatt tttgatctat        300
taacagatat ataaatgcaa aaactgcata accactttaa ctaatacttt caacattttc       360
ggtttgtatt acttcttatt caatgtaat aaaagtatca acaaaaaatt gttaatatac        420
ctctatactt taacgtcaag gagaaaaaac cccggatcgg actactagca gctgtaatac       480
gactcactat agggaatatt aagctaattc tacttcatac attttcaatt aagatgcagt       540
tacttcgctg ttttcaata ttttctgtta ttgcttcagt tttagcacag gaactgacaa       600
ctatatgcga gcaaatcccc tcaccaactt tagaatcgac gccgtactct ttgtcaacga       660
ctactatttt ggccaacggg aaggcaatgc aaggagtttt tgaatattac aaatcagtaa       720
cgtttgtcag taattgcggt tctcacccct caacaactag caaaggcagc cccataaaca       780
cacagtatgt ttttaagctt ctgcaggcta gtggtggtgg tggttctggt ggtggtggtt       840
ctggtggtgg tggttctgct agcatgactg gtggacagca aatgggtcgg gatctgtacg      900
acgatgacga taaggtacca ggatccgcta gcaccaaggg cccagcgtg ttccctctgg        960
ccccagctc caagagcacc tccggcggca ccgccgccct gggctgcctg gtgaaggatt      1020
acttcccaga gcccgtgacc gtgagctgga acagcggcgc cctgaccagc ggcgtgcaca      1080
```

```
cctttcccgc cgtgctgcag tccagcggcc tgtactccct gagcagcgtg gtgaccgtgc    1140
ccagcagcag cctgggcacc cagacctaca tctgcaatgt gaaccacaag cccagcaata    1200
ccaaggtgga taagaaggtg gagcccaaga gcagcgacaa gacacacacg tgtcccccat    1260
gtcccgcccc tgagctgctg ggcggccctt ccgtgttcct gttccctccc aagccaaagg    1320
acaccctgat gatctcccgg acccctgagg tgacctgtgt ggtggtggac gtgagccacg    1380
aggacccaga ggtgaagttc aactggtacg tggacggcgt ggaggtgcac aacgccaaga    1440
ccaagcctag agaggagcag tacaacagca cctaccgcgt ggtgagcgtg ctgaccgtgc    1500
tgcaccagga ttggctgaat ggcaaggagt acaagtgcaa ggtgagcaac aaggccctgc    1560
ctgcccccat cgagaagacc atctccaagg ccaagggcca gcctcgagaa ccacaggtgt    1620
acaccctgcc cccatcccgg gatgagctga ccaagaacca ggtcagcctg acctgcctgg    1680
tcaaaggctt ctatcccagc gacatcgccg tggagtggga gagcaatggg cagccggaga    1740
acaactacaa gaccacgcct cccgtgctgg actccgacgg ctccttcttc ctctacagca    1800
agctcaccgt ggacaagagc aggtggcagc aggggaacgt cttctcatgc tccgtgatgc    1860
atgaggctct gcacaaccac tacacacaga agagcctctc cctgtctccg ggtaaatgag    1920
cggccgctcg atcgagtcta gagggccctt cgaaggtaag cctatcccta accctctcct    1980
cggtctcgat tctacgcgta ccggtcatca tcaccatcac cattgagttt aaacccgctg    2040
atctgataac aacagtgtag atgtaacaaa atcgactttg ttcccactgt acttttagct    2100
cgtacaaaat acaatatact tttcatttct ccgtaaacaa catgttttcc catgtaatat    2160
cctttctat ttttcgttcc gttaccaact ttacacatac tttatatagc tattcacttc    2220
tatacactaa aaaactaaga caattttaat tttgctgcct gccatatttc aatttgttat    2280
aaattcctat aatttatcct attagtagct aaaaaaagat gaatgtgaat cgaatcctaa    2340
gagaattggg caagtgcaca aacaatactt aaataaatac tactcagtaa taacctattt    2400
cttagcattt ttgacgaaat ttgctatttt gttagagtct tttacaccat ttgtctccac    2460
acctccgctt acatcaacac caataacgcc atttaatcta agcgcatcac caacatttc    2520
tggcgtcagt ccaccagcta acataaaatg taagctctcg gggctctctt gccttccaac    2580
ccagtcagaa atcgagttcc aatccaaaag ttcacctgtc ccacctgctt ctgaatcaaa    2640
caagggaata aacgaatgag gtttctgtga agctgcactg agtagtatgt tgcagtcttt    2700
tggaaatacg agtcttttaa taactggcaa accgaggaac tcttggtatt cttgccacga    2760
ctcatctccg tgcagttgga cgatatcaat gccgtaatca ttgaccagag ccaaaacatc    2820
ctccttaggt tgattacgaa acacgccaac caagtatttc ggagtgcctg aactatttt    2880
atatgctttt acaagacttg aaattttcct tgcaataacc gggtcaattg ttctcttttct    2940
attgggcaca catataatac ccagcaagtc agcatcggaa tctagagcac attctgcggc    3000
ctctgtgctc tgcaagccgc aaactttcac caatggacca gaactacctg tgaaattaat    3060
aacagacata ctccaagctg cctttgtgtg cttaatcacg tatactcacg tgctcaatag    3120
tcaccaatgc cctccctctt ggccctctcc ttttctttt tcgaccgaat tcttgaaga    3180
cgaaagggcc tcgtgatacg cctatttta taggttaatg tcatgataat aatgttttct    3240
taggacggat cgcttgcctg taacttacac gcgcctcgta tcttttaatg atggaataat    3300
ttgggaattt actctgtgtt tatttatttt tatgttttgt atttggattt tagaaagtaa    3360
ataaagaagg tagaagagtt acggaatgaa gaaaaaaaaa taaacaaagg tttaaaaaat    3420
```

```
ttcaacaaaa agcgtacttt acatatatat ttattagaca agaaaagcag attaaataga   3480
tatacattcg attaacgata agtaaaatgt aaaatcacag gattttcgtg tgtggtcttc   3540
tacacagaca agatgaaaca attcggcatt aatacctgag agcaggaaga gcaagataaa   3600
aggtagtatt tgttggcgat cccctagag tcttttacat cttcggaaaa caaaaactat    3660
tttttcttta atttcttttt ttactttcta ttttttaattt atatatttat attaaaaaat  3720
ttaaattata attatttta tagcacgtga tgaaaaggac ccaggtggca cttttcgggg    3780
aaatgtgcgc ggaacccta tttgtttatt tttctaaata cattcaaata tgtatccgct    3840
catgagacaa taaccctgat aaatgcttca ataatattga aaaggaaga gtatgagtat    3900 tcaacatttc cgtgtcgccc ttattccctt ttttgcggca ttttgccttc ctgtttttgc   3960
tcacccagaa acgctggtga agtaaaaga tgctgaagat cagttgggtg cacgagtggg    4020
ttacatcgaa ctggatctca acagcggtaa gatccttgag agttttcgcc ccgaagaacg   4080
ttttccaatg atgagcactt ttaaagttct gctatgtggc gcggtattat cccgtgttga   4140
cgccgggcaa gagcaactcg gtcgccgcat acactattct cagaatgact tggttgagta   4200
ctcaccagtc acagaaaagc atcttacgga tggcatgaca gtaagagaat tatgcagtgc   4260
tgccataacc atgagtgata acactgcggc caacttactt ctgacaacga tcggaggacc   4320
gaaggagcta accgctttt tgcacaacat ggggatcat gtaactcgcc ttgatcgttg    4380
ggaaccggag ctgaatgaag ccataccaaa cgacgagcgt gacaccacga tgcctgtagc   4440
aatggcaaca acgttgcgca aactattaac tggcgaacta cttactctag cttcccggca   4500
acaattaata gactggatgg aggcggataa agttgcagga ccacttctgc gctcggccct   4560
tccggctggc tggtttattg ctgataaatc tggagccggt gagcgtgggt ctcgcggtat   4620
cattgcagca ctggggccag atggtaagcc ctcccgtatc gtagttatct acacgacggg   4680
cagtcaggca actatggatg aacgaaatag acagatcgct gagataggtg cctcactgat   4740
taagcattgg taactgtcag accaagttta ctcatatata ctttagattg atttaaaact   4800 tcattttaa tttaaaagga tctaggtgaa gatcctttt gataatctca tgaccaaaat    4860
cccttaacgt gagttttcgt tccactgagc gtcagacccc gtagaaaaga tcaaaggatc   4920
ttcttgagat ccttttttc tgcgcgtaat ctgctgcttg caaacaaaaa aaccaccgct    4980
accagcggtg gtttgtttgc cggatcaaga gctaccaact cttttccga aggtaactgg    5040 cttcagcaga gcgcagatac caaatactgt ccttctagtg tagccgtagt taggccacca   5100
cttcaagaac tctgtagcac cgcctacata cctcgctctg ctaatcctgt taccagtggc   5160
tgctgccagt ggcgataagt cgtgtcttac cgggttggac tcaagacgat agttaccgga   5220
taaggcgcag cggtcgggct gaacgggggg ttcgtgcaca cagcccagct tggagcgaac   5280
gacctacacc gaactgagat acctacagcg tgagcattga gaaagcgcca cgcttcccga   5340
agggagaaag gcggacaggt atccggtaag cggcagggtc ggaacaggag agcgcacgag   5400
ggagcttcca gggggaacg cctggtatct ttatagtcct gtcgggtttc gccacctctg    5460
acttgagcgt cgatttttgt gatgctcgtc aggggggccg agcctatgga aaaacgccag   5520
caacgcggcc tttttacggt tcctggcctt tgctggcct tttgctcaca tgttctttcc   5580
tgcgttatcc cctgattctg tggataaccg tattaccgcc tttgagtgag ctgataccgc   5640
tcgccgcagc cgaacgaccg agcgcagcga gtcagtgagc gaggaagcgg aagagcgccc   5700
aatacgcaaa ccgcctctcc ccgcgcgttg gccgattcat taatgcagct ggcacgacag   5760
gtttcccgac tggaaagcgg gcagtgagcg caacgcaatt aatgtgagtt acctcactca   5820
```

```
ttaggcaccc caggctttac actttatgct tccggctcct atgttgtgtg gaattgtgag    5880
cggataacaa tttcacacag gaaacagcta tgaccatgat tacgccaagc tcggaattaa    5940
ccctcactaa agggaacaaa agctggctag t                                   5971
```

<210> SEQ ID NO 17
<211> LENGTH: 5657
<212> TYPE: DNA
<213> ORGANISM: artificial
<220> FEATURE:
<223> OTHER INFORMATION: pYD1CH12

<400> SEQUENCE: 17

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgcttcagt tttagcacag gaactgacaa     600
ctatatgcga gcaaatcccc tcaccaactt tagaatcgac gccgtactct tgtcaacga      660 ctactatttt ggccaacggg aaggcaatgc aaggagtttt tgaatattac aaatcagtaa     720
cgtttgtcag taattgcggt tctcaccct caacaactag caaaggcagc cccataaaca      780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccgcta gcaccaaggg ccccagcgtg ttccctctgg     960
cccccagctc caagagcacc tccggcggca ccgccgccct gggctgcctg gtgaaggatt    1020
acttcccaga gccgtgacc gtgagctgga cagcggcgc cctgaccagc ggcgtgcaca    1080
cctttcccgc cgtgctgcag tccagcggcc tgtactccct gagcagcgtg gtgaccgtgc    1140
ccagcagcag cctgggcacc cagacctaca tctgcaatgt gaaccacaag cccagcaata    1200
ccaaggtgga taagaaggtg gagcccaaga gcagcgacaa gacacacacg tgtcccccat    1260
gtcccgcccc tgagctgctg ggcggcccctt ccgtgttcct gttccctccc aagccaaagg    1320
acaccctgat gatctcccgg acccctgagg tgacctgtgt ggtggtggac gtgagccacg    1380
aggacccaga ggtgaagttc aactggtacg tggacggcgt ggaggtgcac aacgccaaga    1440
ccaagcctag agaggagcag tacaacagca cctaccgcgt ggtgagcgtg ctgaccgtgc    1500
tgcaccagga ttggctgaat ggcaaggagt acaagtgcaa ggtgagcaac aaggccctgc    1560
ctgcccccat cgagaagacc atctccaagg ccaagggcca gcctcgaggc cgctcgatcg    1620
agtctagagg gcccttcgaa ggtaagccta tccctaaccc tctcctcggt ctcgattcta    1680
cgcgtaccgg tcatcatcac catcaccatt gagtttaaac ccgctgatct gataacaaca    1740
gtgtagatgt aacaaaatcg actttgttcc cactgtactt ttagctcgta caaaatacaa    1800 tatactttc atttctccgt aaacaacatg ttttcccatg taatatcctt ttctattttt    1860
```

```
cgttccgtta ccaactttac acatacttta tatagctatt cacttctata cactaaaaaa    1920
ctaagacaat tttaattttg ctgcctgcca tatttcaatt tgttataaat tcctataatt    1980
tatcctatta gtagctaaaa aagatgaat  gtgaatcgaa tcctaagaga attgggcaag    2040
tgcacaaaca atacttaaat aaatactact cagtaataac ctatttctta gcattttga    2100 cgaaatttgc tattttgtta gagtcttta  caccatttgt ctccacacct ccgcttacat    2160
caacaccaat aacgccattt aatctaagcg catcaccaac attttctggc gtcagtccac    2220
cagctaacat aaaatgtaag ctctcggggc tctcttgcct tccaacccag tcagaaatcg    2280
agttccaatc caaagttca  cctgtcccac ctgcttctga atcaaacaag ggaataaacg    2340
aatgaggttt ctgtgaagct gcactgagta gtatgttgca gtcttttgga aatacgagtc    2400
ttttaataac tggcaaaccg aggaactctt ggtattcttg ccacgactca tctccgtgca    2460
gttggacgat atcaatgccg taatcattga ccagagccaa acatcctcc  ttaggttgat    2520 tacgaaacac gccaaccaag tatttcggag tgcctgaact attttatat  gcttttacaa    2580 gacttgaaat tttccttgca ataaccgggt caattgttct ctttctattg ggcacacata    2640
taatacccag caagtcagca tcggaatcta gagcacattc tgcggcctct gtgctctgca    2700
agccgcaaac tttcaccaat ggaccagaac tacctgtgaa attaataaca gacatactcc    2760
aagctgcctt tgtgtgctta atcacgtata ctcacgtgct caatagtcac caatgccctc    2820
cctcttggcc ctctcctttt ctttttcga  ccgaatttct tgaagacgaa agggcctcgt    2880
gatacgccta ttttatagg  ttaatgtcat gataataatg gtttcttagg acggatcgct    2940
tgcctgtaac ttcacgcgc  ctcgtatctt taatgatgg  aataatttgg gaatttactc    3000
tgtgtttatt tattttatg  ttttgtattt ggattttaga agtaaataa  agaaggtaga    3060 agagttacgg aatgaagaaa aaaaaataaa caaaggttta aaaaatttca acaaaaagcg    3120
tactttacat atatatttat tagacaagaa aagcagatta aatagatata cattcgatta    3180
acgataagta aaatgtaaaa tcacaggatt ttcgtgtgtg gtcttctaca cagacaagat    3240
gaaacaattc ggcattaata cctgagagca ggaagagcaa gataaaaggt agtatttgtt    3300
ggcgatcccc ctagagtctt ttacatcttc ggaaaacaaa aactattttt tctttaattt    3360
ctttttttac tttctatttt taatttatat atttatatta aaaaatttaa attataatta    3420
tttttatagc acgtgatgaa aaggaccag  gtggcacttt tcggggaaat gtgcgcggaa    3480
cccctatttg tttattttc  taaatacatt caaatatgta tccgctcatg agacaataac    3540
cctgataaat gcttcaataa tattgaaaaa ggaagagtat gagtattcaa catttccgtg    3600
tcgcccttat tccctttttt gcggcatttt gccttcctgt ttttgctcac ccagaaacgc    3660
tggtgaaagt aaaagatgct gaagatcagt tgggtgcacg agtgggttac atcgaactgg    3720
atctcaacag cggtaagatc cttgagagtt ttcgccccga agaacgtttt ccaatgatga    3780
gcacttttaa agttctgcta tgtggcgcgg tattatcccg tgttgacgcc gggcaagagc    3840
aactcggtcg ccgcatacac tattctcaga atgacttggt tgagtactca ccagtcacag    3900
aaaagcatct tacgatggc  atgacagtaa gagaattatg cagtgctgcc ataaccatga    3960
gtgataacac tgcggccaac ttacttctga caacgatcgg aggaccgaag gagctaaccg    4020
cttttttgca acatgggg   gatcatgtaa ctcgccttga tcgttgggaa ccggagctga    4080
atgaagccat accaaacgac gagcgtgaca ccacgatgcc tgtagcaatg gcaacaacgt    4140
tgcgcaaact attaactggc gaactactta ctctagcttc ccggcaacaa ttaatagact    4200
ggatggaggc ggataaagtt gcaggaccac ttctgcgctc ggcccttccg gctggctggt    4260
```

```
ttattgctga taaatctgga gccggtgagc gtgggtctcg cggtatcatt gcagcactgg   4320
ggccagatgg taagccctcc cgtatcgtag ttatctacac gacgggcagt caggcaacta   4380
tggatgaacg aaatagacag atcgctgaga taggtgcctc actgattaag cattggtaac   4440
tgtcagacca agtttactca tatatacttt agattgattt aaaacttcat ttttaattta   4500
aaaggatcta ggtgaagatc cttttgata atctcatgac caaaatccct aacgtgagt    4560 tttcgttcca ctgagcgtca gacccctag aaaagatcaa aggatcttct tgagatcctt    4620
tttttctgcg cgtaatctgc tgcttgcaaa caaaaaaacc accgctacca gcggtggttt   4680
gtttgccgga tcaagagcta ccaactcttt ttccgaaggt aactggcttc agcagagcgc   4740
agataccaaa tactgtcctt ctagtgtagc cgtagttagg ccaccacttc aagaactctg   4800
tagcaccgcc tacatacctc gctctgctaa tcctgttacc agtggctgct gccagtggcg   4860
ataagtcgtg tcttaccggg ttggactcaa gacgatagtt accggataag cgcagcggt    4920 cgggctgaac ggggggttcg tgcacacagc ccagcttgga gcgaacgacc tacaccgaac   4980
tgagatacct acagcgtgag cattgagaaa gcgccacgct tcccgaaggg agaaaggcgg   5040
acaggtatcc ggtaagcggc agggtcggaa caggagagcg cacgagggag cttccagggg   5100
ggaacgcctg gtatctttat agtcctgtcg ggtttcgcca cctctgactt gagcgtcgat   5160
ttttgtgatg ctcgtcaggg gggccgagcc tatggaaaaa cgccagcaac gcggcctttt   5220
tacggttcct ggccttttgc tggccttttg ctcacatgtt ctttcctgcg ttatcccctg   5280
attctgtgga taaccgtatt accgcctttg agtgagctga taccgctcgc cgcagccgaa   5340
cgaccgagcg cagcgagtca gtgagcgagg aagcggaaga gcgcccaata cgcaaaccgc   5400
ctctccccgc gcgttggccg attcattaat gcagctggca cgacaggttt cccgactgga   5460
aagcgggcag tgagcgcaac gcaattaatg tgagttacct cactcattag gcaccccagg   5520
ctttacactt tatgcttccg gctcctatgt tgtgtggaat tgtgagcgga taacaatttc   5580
acacaggaaa cagctatgac catgattacg ccaagctcgg aattaaccct cactaaaggg   5640
aacaaaagct ggctagt                                                  5657
```

```
<210> SEQ ID NO 18
<211> LENGTH: 738
<212> TYPE: DNA
<213> ORGANISM: artificial
<220> FEATURE:
<223> OTHER INFORMATION: Fcab01
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (617)..(618)
```

```
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t

<400> SEQUENCE: 18
ggcccagccg gccatggccg agcccaaatc ttgtgacaaa actcacacat gcccaccgtg      60
cccagcacct gaactcctgg ggggaccgtc agtcttcctc ttccccccaa acccaagga     120 caccctcatg atctcccgga cccctgaggt cacatgcgtg gtggtggacg tgagccacga     180
agaccctgag gtcaagttca actggtacgt ggacggcgtg gaggtgcata atgccaagac     240
aaagccgcgg gaggagcagt acaacagcac gtaccgtgtg gtcagcgtcc tcaccgtcct     300
gcaccaggac tggctgaatg gcaaggagta caagtgcaag gtctccaaca aagcccctcc     360
agcccccatc gagaaaacca tctccaaagc caaagggcag cctcgagaac acaggtgta     420 caccctgccc ccatcccggg atgaactgnn bnnbnnbcag gtcagcctga cctgcctggt     480
caaaggcttc tatcccagcg acatcgccgt ggagtgggag agcaatgggc agccggagaa     540
caactacaag accacgcctc ccgtgctgga ctccgacggc tccttcttcc tctacagcaa     600
gctcaccgtg nnbnnbnnbn nbnnbnnbnn bnnbaggtgg nnbnnbggga acgtcttctc     660
atgctccgtg atgcatgagg ctctgcacaa ccactacacg cagaagagcc tctccctgtc     720
tccgggtaaa gcggccgc                                                  738

<210> SEQ ID NO 19
<211> LENGTH: 738
<212> TYPE: DNA
<213> ORGANISM: artificial
<220> FEATURE:
<223> OTHER INFORMATION: Fcab02

<400> SEQUENCE: 19
ggcccagccg gccatggccg agcccaaatc ttgtgacaaa actcacacat gcccaccgtg      60
cccagcacct gaactcctgg ggggaccgtc agtcttcctc ttccccccaa acccaagga     120 caccctcatg atctcccgga cccctgaggt cacatgcgtg gtggtggacg tgagccacga     180
agaccctgag gtcaagttca actggtacgt ggacggcgtg gaggtgcata atgccaagac     240
aaagccgcgg gaggagcagt acaacagcac gtaccgtgtg gtcagcgtcc tcaccgtcct     300
gcaccaggac tggctgaatg gcaaggagta caagtgcaag gtctccaaca aagcccctcc     360
```

```
agcccccatc gagaaaacca tctccaaagc caaagggcag cctcgagaac cacaggtgta      420
caccctgccc ccatcccggg atgagctgkm tkmtkmtcag gtgagcctga cctgcctggt      480
caaaggcttc tatcccagcg acatcgccgt ggagtgggag agcaatgggc agccggagaa      540
caactacaag accacgcctc ccgtgctgga ctccgacggc tccttcttcc tctacagcaa      600
gctcaccgtg kmtkmtkmtk mtkmtkmtkm tkmtaggtgg kmtkmtggga acgtcttctc      660
atgctccgtg atgcatgagg ctctgcacaa ccactacacg cagaagagcc tctccctgtc      720
tccgggtaaa gcggccgc                                                   738
```

<210> SEQ ID NO 20
<211> LENGTH: 750
<212> TYPE: DNA
<213> ORGANISM: artificial
<220> FEATURE:
<223> OTHER INFORMATION: Fcab03
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (635)..(636)
<223> OTHER INFORMATION: n is a, c, g, or t
<220> FEATURE:
<221> NAME/KEY: misc_feature
<222> LOCATION: (638)..(639)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t

<400> SEQUENCE: 20

```
ggcccagccg gccatggccg agcccaaatc ttgtgacaaa actcacacat gcccaccgtg       60
```

| | |
|---|---|
| cccagcacct gaactcctgg ggggaccgtc agtcttcctc ttccccccaa acccaagga | 120 |
| caccctcatg atctcccgga cccctgaggt cacatgcgtg gtggtggacg tgagccacga | 180 |
| agaccctgag gtcaagttca actggtacgt ggacggcgtg gaggtgcata atgccaagac | 240 |
| aaagccgcgg gaggagcagt acaacagcac gtaccgtgtg gtcagcgtcc tcaccgtcct | 300 |
| gcaccaggac tggctgaatg caaggagta caagtgcaag gtctccaaca aagcccctccc | 360 |
| agccccatc gagaaaacca tctccaaagc caagggcag cctcgagaac acaggtgta | 420 |
| caccctgccc ccttcccggg atgagctgnn bnnbnnbcag gtcagcctga cctgcctggt | 480 |
| caaaggcttc tatcccagcg acatcgccgt ggagtgggag agcaatgggc agccggagaa | 540 |
| caactacaag accacgcctc ccgtgctgga ctccgacggc tccttcttcc tctacagcaa | 600 |
| gctcaccgtg ggttctnnbn nbnnbnnbnn bnnbnnbnnb agcggcaggt ggnnbnnbgg | 660 |
| gaacgtcttc tcatgctccg tgatgcatga ggctctgcac aaccactaca cgcagaagag | 720 |
| cctctccctg tctccgggta aagcggccgc | 750 |

<210> SEQ ID NO 21
<211> LENGTH: 750
<212> TYPE: DNA
<213> ORGANISM: artificial
<220> FEATURE:
<223> OTHER INFORMATION: Fcab04

<400> SEQUENCE: 21

| | |
|---|---|
| ggcccagccg gccatggccg agcccaaatc ttgtgacaaa actcacacat gcccaccgtg | 60 |
| cccagcacct gaactcctgg ggggaccgtc agtcttcctc ttccccccaa acccaagga | 120 |
| caccctcatg atctcccgga cccctgaggt cacatgcgtg gtggtggacg tgagccacga | 180 |
| agaccctgag gtcaagttca actggtacgt ggacggcgtg gaggtgcata atgccaagac | 240 |
| aaagccgcgg gaggagcagt acaacagcac gtaccgtgtg gtcagcgtcc tcaccgtcct | 300 |
| gcaccaggac tggctgaatg caaggagta caagtgcaag gtctccaaca aagcccctccc | 360 |
| agccccatc gagaaaacca tctccaaagc caagggcag cctcgagaac acaggtgta | 420 |
| caccctgccc ccatctcggg atgagctgkm tkmtkmtcag gtcagcctga cctgcctggt | 480 |
| caaaggcttc tatcccagcg acatcgccgt ggagtgggag agcaatgggc agccggagaa | 540 |
| caactacaag accacgcctc ccgtgctgga ctccgacggc tccttcttcc tctacagcaa | 600 |
| gctcaccgtg ggttctkmtk mtkmtkmtkm tkmtkmtkmt agcggcaggt ggkmtkmtgg | 660 |
| gaacgtcttc tcatgctccg tgatgcatga ggctctgcac aaccactaca cgcagaagag | 720 |
| cctctccctg tctccgggta aagcggccgc | 750 |

<210> SEQ ID NO 22
<211> LENGTH: 738
<212> TYPE: DNA
<213> ORGANISM: artificial
<220> FEATURE:
<223> OTHER INFORMATION: Fcab05
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t

```
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t

<400> SEQUENCE: 22
ggcccagccg gccatggccg agcccaaatc ttgtgacaaa actcacacat gcccaccgtg    60
cccagcacct gaactcctgg ggggaccgtc agtcttcctc ttccccccaa acccaagga   120 caccctcatg atctcccgga cccctgaggt cacatgcgtg gtggtggacg tgagccacga   180
agaccctgag gtcaagttca actggtacgt ggacggcgtg gaggtgcata atgccaagac   240
aaagccgcgg gaggagcagt acaacagcac gtaccgtgtg gtcagcgtcc tcaccgtcct   300
gcaccaggac tggctgaatg gcaaggagta caagtgcaag gtctccaaca agccctccc   360 agcccccatc gagaaaacca tctccaaagc caaagggcag cctcgagaac acaggtgta   420 caccctgccc ccatcccgtg atgagkmtnn bnnbnnbkmt gtcagcctga cctgcctggt   480
caaaggcttc tatcccagcg acatcgccgt ggagtgggag agcaatgggc agccggagaa   540
caactacaag accacgcctc ccgtgctgga ctccgacggc tccttcttcc tctacagcaa   600
gctcaccgtg nnbnnbnnbn nbnnbnnbnn bnnbaggtgg nnbnnbggga acgtcttctc   660
atgctccgtg atgcatgagg ctctgcacaa ccactacacg cagaagagcc tctccctgtc   720
tccgggtaaa gcggccgc                                                738

<210> SEQ ID NO 23
<211> LENGTH: 738
<212> TYPE: DNA
<213> ORGANISM: artificial
<220> FEATURE:
<223> OTHER INFORMATION: Fcab06

<400> SEQUENCE: 23
```

```
ggcccagccg gccatggccg agcccaaatc ttgtgacaaa actcacacat gcccaccgtg    60
cccagcacct gaactcctgg ggggaccgtc agtcttcctc ttccccccaa aacccaagga   120
caccctcatg atctcccgga cccctgaggt cacatgcgtg gtggtggacg tgagccacga   180
agaccctgag gtcaagttca actggtacgt ggacggcgtg gaggtgcata atgccaagac   240
aaagccgcgg gaggagcagt acaacagcac gtaccgtgtg gtcagcgtcc tcaccgtcct   300
gcaccaggac tggctgaatg caaggagta caagtgcaag gtctccaaca aagccctccc   360
agcccccatc gagaaaacca tctccaaagc caaagggcag cctcgagaac cacaggtgta   420
caccctgccc ccatcccggg acgagkmtkm tkmtkmtkmt gtcagcctga cctgcctggt   480
caaaggcttc tatcccagcg acatcgccgt ggagtgggag agcaatgggc agccggagaa   540
caactacaag accacgcctc ccgtgctgga ctccgacggc tccttcttcc tctacagcaa   600
gctcaccgtg kmtkmtkmtk mtkmtkmtkm tkmtaggtgg kmtkmtggga acgtcttctc   660
atgctccgtg atgcatgagg ctctgcacaa ccactacacg cagaagagcc tctccctgtc   720
tccgggtaaa gcggccgc                                                 738

<210> SEQ ID NO 24
<211> LENGTH: 85
<212> TYPE: DNA
<213> ORGANISM: artificial
<220> FEATURE:
<223> OTHER INFORMATION: PCR primer gapch35

<400> SEQUENCE: 24
caacaaggcc ctgcctgccc ccatcgagaa gaccatctcc aaggccaagg gccagcctcg    60
agaaccacag gtgtacaccc tgccc                                          85

<210> SEQ ID NO 25
<211> LENGTH: 99
<212> TYPE: DNA
<213> ORGANISM: artificial
<220> FEATURE:
<223> OTHER INFORMATION: PCR primer gapfcs3

<400> SEQUENCE: 25
gagaccgagg agagggttag ggataggctt accttcgaag ggccctctag actcgatcga    60
gcggccgctc atttacccgg agacagggag aggctcttc                           99

<210> SEQ ID NO 26
<211> LENGTH: 79
<212> TYPE: DNA
<213> ORGANISM: artificial
<220> FEATURE:
<223> OTHER INFORMATION: primer Abmut
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 26
gaaccacagg tgtacaccct gccccatcc cgggatgagc tgnnbnnbnn bcaggtcagc    60
ctgacctgcc tggtcaaag                                                79
```

```
<210> SEQ ID NO 27
<211> LENGTH: 79
<212> TYPE: DNA
<213> ORGANISM: artificial
<220> FEATURE:
<223> OTHER INFORMATION: primer Abmut2LR
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 27
gaaccacagg tgtacaccct gcccccatcc cgggatgagn nbnnbnnbnn bnnbgtcagc      60
ctgacctgcc tggtcaaag                                                  79

<210> SEQ ID NO 28
<211> LENGTH: 79
<212> TYPE: DNA
<213> ORGANISM: artificial
<220> FEATURE:
<223> OTHER INFORMATION: primer Abmut1L
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 28
gaaccacagg tgtacaccct gcccccatcc cgggatgagn nbnnbnnbnn bcaggtcagc      60
ctgacctgcc tggtcaaag                                                  79

<210> SEQ ID NO 29
<211> LENGTH: 79
<212> TYPE: DNA
<213> ORGANISM: artificial
<220> FEATURE:
<223> OTHER INFORMATION: primer Abmut1R
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
```

```
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 29
gaaccacagg tgtacaccct gcccccatcc cgggatgagc tgnnbnnbnn bnnbgtcagc    60
ctgacctgcc tggtcaaag                                                 79

<210> SEQ ID NO 30
<211> LENGTH: 5
<212> TYPE: PRT
<213> ORGANISM: artificial
<220> FEATURE:
<223> OTHER INFORMATION: AB-loop sequence AA143ff

<400> SEQUENCE: 30

Leu Asp Asn Ser Gln
1               5

<210> SEQ ID NO 31
<211> LENGTH: 5
<212> TYPE: PRT
<213> ORGANISM: artificial
<220> FEATURE:
<223> OTHER INFORMATION: AB-loop sequence AA143ff

<400> SEQUENCE: 31

Tyr Glu Gly Ser Ser
1               5

<210> SEQ ID NO 32
<211> LENGTH: 5
<212> TYPE: PRT
<213> ORGANISM: artificial
<220> FEATURE:
<223> OTHER INFORMATION: AB-loop sequence AA143ff

<400> SEQUENCE: 32

Tyr Met Ser Ala Asp
1               5

<210> SEQ ID NO 33
<211> LENGTH: 5
<212> TYPE: PRT
<213> ORGANISM: artificial
<220> FEATURE:
<223> OTHER INFORMATION: AB-loop sequence AA143ff

<400> SEQUENCE: 33

Tyr Arg Arg Gly Asp
1               5

<210> SEQ ID NO 34
<211> LENGTH: 5
<212> TYPE: PRT
<213> ORGANISM: artificial
<220> FEATURE:
<223> OTHER INFORMATION: AB-loop sequence AA143ff

<400> SEQUENCE: 34

Leu Met Ser Arg Gln
```

```
<210> SEQ ID NO 35
<211> LENGTH: 5
<212> TYPE: PRT
<213> ORGANISM: artificial
<220> FEATURE:
<223> OTHER INFORMATION: AB-loop sequence AA143ff

<400> SEQUENCE: 35

Leu His Leu Ala Gln
1               5

<210> SEQ ID NO 36
<211> LENGTH: 5
<212> TYPE: PRT
<213> ORGANISM: artificial
<220> FEATURE:
<223> OTHER INFORMATION: AB-loop sequence AA143ff

<400> SEQUENCE: 36

Tyr Leu Ser Lys Asp
1               5

<210> SEQ ID NO 37
<211> LENGTH: 5
<212> TYPE: PRT
<213> ORGANISM: artificial
<220> FEATURE:
<223> OTHER INFORMATION: AB-loop sequence AA143ff

<400> SEQUENCE: 37

Tyr Arg Ser Gly Ser
1               5

<210> SEQ ID NO 38
<211> LENGTH: 5
<212> TYPE: PRT
<213> ORGANISM: artificial
<220> FEATURE:
<223> OTHER INFORMATION: AB-loop sequence AA143ff

<400> SEQUENCE: 38

Leu Arg Asp Gly Gln
1               5

<210> SEQ ID NO 39
<211> LENGTH: 5
<212> TYPE: PRT
<213> ORGANISM: artificial
<220> FEATURE:
<223> OTHER INFORMATION: AB-loop sequence AA143ff

<400> SEQUENCE: 39

Tyr Ser Ala Asn Thr
1               5

<210> SEQ ID NO 40
<211> LENGTH: 5
<212> TYPE: PRT
<213> ORGANISM: artificial
<220> FEATURE:
<223> OTHER INFORMATION: AB-loop sequence AA143ff

<400> SEQUENCE: 40

Tyr Ala Ser Asn Thr
1               5
```

```
<210> SEQ ID NO 41
<211> LENGTH: 5
<212> TYPE: PRT
<213> ORGANISM: artificial
<220> FEATURE:
<223> OTHER INFORMATION: AB-loop sequence AA143ff

<400> SEQUENCE: 41

Tyr Ser Asp Gly Asp
1               5

<210> SEQ ID NO 42
<211> LENGTH: 5
<212> TYPE: PRT
<213> ORGANISM: artificial
<220> FEATURE:
<223> OTHER INFORMATION: AB-loop sequence AA143ff

<400> SEQUENCE: 42

Tyr Ser Gly Gly Ser
1               5

<210> SEQ ID NO 43
<211> LENGTH: 5
<212> TYPE: PRT
<213> ORGANISM: artificial
<220> FEATURE:
<223> OTHER INFORMATION: AB-loop sequence AA143ff

<400> SEQUENCE: 43

Tyr Gly Arg Asp Ser
1               5

<210> SEQ ID NO 44
<211> LENGTH: 5
<212> TYPE: PRT
<213> ORGANISM: artificial
<220> FEATURE:
<223> OTHER INFORMATION: AB-loop sequence AA143ff

<400> SEQUENCE: 44

Tyr Ala Gly Gly Thr
1               5

<210> SEQ ID NO 45
<211> LENGTH: 5
<212> TYPE: PRT
<213> ORGANISM: artificial
<220> FEATURE:
<223> OTHER INFORMATION: AB-loop sequence AA143ff

<400> SEQUENCE: 45

Tyr Ser Ser Asp Ser
1               5

<210> SEQ ID NO 46
<211> LENGTH: 5
<212> TYPE: PRT
<213> ORGANISM: artificial
<220> FEATURE:
<223> OTHER INFORMATION: AB-loop sequence AA143ff

<400> SEQUENCE: 46

Tyr His Ser Gly Ser
1               5
```

```
<210> SEQ ID NO 47
<211> LENGTH: 5
<212> TYPE: PRT
<213> ORGANISM: artificial
<220> FEATURE:
<223> OTHER INFORMATION: AB-loop sequence AA143ff

<400> SEQUENCE: 47

Tyr Leu Thr Asn Ser
1               5

<210> SEQ ID NO 48
<211> LENGTH: 5
<212> TYPE: PRT
<213> ORGANISM: artificial
<220> FEATURE:
<223> OTHER INFORMATION: AB-loop sequence AA143ff

<400> SEQUENCE: 48

Tyr Gly Ser Glu Glu
1               5

<210> SEQ ID NO 49
<211> LENGTH: 5
<212> TYPE: PRT
<213> ORGANISM: artificial
<220> FEATURE:
<223> OTHER INFORMATION: AB-loop sequence AA143ff

<400> SEQUENCE: 49

Tyr Arg Ser Gly Glu
1               5

<210> SEQ ID NO 50
<211> LENGTH: 5
<212> TYPE: PRT
<213> ORGANISM: artificial
<220> FEATURE:
<223> OTHER INFORMATION: AB-loop sequence AA143ff

<400> SEQUENCE: 50

Tyr Gly Thr Asp Asp
1               5

<210> SEQ ID NO 51
<211> LENGTH: 12
<212> TYPE: PRT
<213> ORGANISM: artificial
<220> FEATURE:
<223> OTHER INFORMATION: EF-loop sequence AA198ff

<400> SEQUENCE: 51

Ile Arg Ser Ser Val Gly Ser Arg Arg Trp Trp Ser
1               5                   10

<210> SEQ ID NO 52
<211> LENGTH: 12
<212> TYPE: PRT
<213> ORGANISM: artificial
<220> FEATURE:
<223> OTHER INFORMATION: EF-loop sequence AA198ff

<400> SEQUENCE: 52

Ala Arg Tyr Ser Pro Arg Met Leu Arg Trp Ala His
1               5                   10
```

```
<210> SEQ ID NO 53
<211> LENGTH: 12
<212> TYPE: PRT
<213> ORGANISM: artificial
<220> FEATURE:
<223> OTHER INFORMATION: EF-loop sequence AA198ff

<400> SEQUENCE: 53

Ser Arg Arg Asp Ser Ser Leu Leu Arg Trp Ala His
1               5                   10

<210> SEQ ID NO 54
<211> LENGTH: 12
<212> TYPE: PRT
<213> ORGANISM: artificial
<220> FEATURE:
<223> OTHER INFORMATION: EF-loop sequence AA198ff

<400> SEQUENCE: 54

Ala Pro Gly Ser Lys Gly Tyr Arg Arg Trp Ala Leu
1               5                   10

<210> SEQ ID NO 55
<211> LENGTH: 12
<212> TYPE: PRT
<213> ORGANISM: artificial
<220> FEATURE:
<223> OTHER INFORMATION: EF-loop sequence AA198ff

<400> SEQUENCE: 55

Asp Lys Pro Phe Trp Gly Thr Ser Arg Trp Ser Arg
1               5                   10

<210> SEQ ID NO 56
<211> LENGTH: 12
<212> TYPE: PRT
<213> ORGANISM: artificial
<220> FEATURE:
<223> OTHER INFORMATION: EF-loop sequence AA198ff

<400> SEQUENCE: 56

Ser Ile Asn Asp Leu Ile Asn His Arg Trp Pro Tyr
1               5                   10

<210> SEQ ID NO 57
<211> LENGTH: 12
<212> TYPE: PRT
<213> ORGANISM: artificial
<220> FEATURE:
<223> OTHER INFORMATION: EF-loop sequence AA198ff

<400> SEQUENCE: 57

Met Trp Gly Ser Arg Asp Tyr Trp Arg Trp Ser His
1               5                   10

<210> SEQ ID NO 58
<211> LENGTH: 12
<212> TYPE: PRT
<213> ORGANISM: artificial
<220> FEATURE:
<223> OTHER INFORMATION: EF-loop sequence AA198ff

<400> SEQUENCE: 58

Asn Ser Gly Ser Ala Met Met Val Arg Trp Ala His
1               5                   10

<210> SEQ ID NO 59
```

```
<211> LENGTH: 12
<212> TYPE: PRT
<213> ORGANISM: artificial
<220> FEATURE:
<223> OTHER INFORMATION: EF-loop sequence AA198ff

<400> SEQUENCE: 59

Gln Arg Ser Arg Leu Ser Arg Gln Arg Trp Trp Arg
1               5                   10

<210> SEQ ID NO 60
<211> LENGTH: 12
<212> TYPE: PRT
<213> ORGANISM: artificial
<220> FEATURE:
<223> OTHER INFORMATION: EF-loop sequence AA198ff

<400> SEQUENCE: 60

Ala Arg Tyr Ser Pro Arg Met Leu Arg Trp Ala His
1               5                   10

<210> SEQ ID NO 61
<211> LENGTH: 12
<212> TYPE: PRT
<213> ORGANISM: artificial
<220> FEATURE:
<223> OTHER INFORMATION: EF-loop sequence AA198ff

<400> SEQUENCE: 61

Ala Arg Tyr Ser Pro Arg Met Leu Arg Trp Ala His
1               5                   10

<210> SEQ ID NO 62
<211> LENGTH: 12
<212> TYPE: PRT
<213> ORGANISM: artificial
<220> FEATURE:
<223> OTHER INFORMATION: EF-loop sequence AA198ff

<400> SEQUENCE: 62

Ala Arg Tyr Ser Pro Arg Met Leu Arg Trp Ala His
1               5                   10

<210> SEQ ID NO 63
<211> LENGTH: 12
<212> TYPE: PRT
<213> ORGANISM: artificial
<220> FEATURE:
<223> OTHER INFORMATION: EF-loop sequence AA198ff

<400> SEQUENCE: 63

Ala Arg Tyr Ser Pro Arg Met Leu Arg Trp Ala His
1               5                   10

<210> SEQ ID NO 64
<211> LENGTH: 12
<212> TYPE: PRT
<213> ORGANISM: artificial
<220> FEATURE:
<223> OTHER INFORMATION: EF-loop sequence AA198ff

<400> SEQUENCE: 64

Ala Arg Tyr Ser Pro Arg Met Leu Arg Trp Ala His
1               5                   10

<210> SEQ ID NO 65
<211> LENGTH: 12
```

```
<212> TYPE: PRT
<213> ORGANISM: artificial
<220> FEATURE:
<223> OTHER INFORMATION: EF-loop sequence AA198ff

<400> SEQUENCE: 65

Ala Arg Tyr Ser Pro Arg Met Leu Arg Trp Ala His
1               5                   10

<210> SEQ ID NO 66
<211> LENGTH: 12
<212> TYPE: PRT
<213> ORGANISM: artificial
<220> FEATURE:
<223> OTHER INFORMATION: EF-loop sequence AA198ff

<400> SEQUENCE: 66

Ala Arg Tyr Ser Pro Arg Met Leu Arg Trp Ala His
1               5                   10

<210> SEQ ID NO 67
<211> LENGTH: 12
<212> TYPE: PRT
<213> ORGANISM: artificial
<220> FEATURE:
<223> OTHER INFORMATION: EF-loop sequence AA198ff

<400> SEQUENCE: 67

Ala Arg Tyr Ser Pro Arg Met Leu Arg Trp Ala His
1               5                   10

<210> SEQ ID NO 68
<211> LENGTH: 12
<212> TYPE: PRT
<213> ORGANISM: artificial
<220> FEATURE:
<223> OTHER INFORMATION: EF-loop sequence AA198ff

<400> SEQUENCE: 68

Ala Arg Tyr Ser Pro Arg Met Leu Arg Trp Ala His
1               5                   10

<210> SEQ ID NO 69
<211> LENGTH: 12
<212> TYPE: PRT
<213> ORGANISM: artificial
<220> FEATURE:
<223> OTHER INFORMATION: EF-loop sequence AA198ff

<400> SEQUENCE: 69

Ala Arg Tyr Ser Pro Arg Met Leu Arg Trp Ala His
1               5                   10

<210> SEQ ID NO 70
<211> LENGTH: 12
<212> TYPE: PRT
<213> ORGANISM: artificial
<220> FEATURE:
<223> OTHER INFORMATION: EF-loop sequence AA198ff

<400> SEQUENCE: 70

Ala Arg Tyr Ser Pro Arg Met Leu Arg Trp Ala His
1               5                   10

<210> SEQ ID NO 71
<211> LENGTH: 12
<212> TYPE: PRT
```

<213> ORGANISM: artificial
<220> FEATURE:
<223> OTHER INFORMATION: EF-loop sequence AA198ff

<400> SEQUENCE: 71

Ala Arg Tyr Ser Pro Arg Met Leu Arg Trp Ala His
1               5                   10

<210> SEQ ID NO 72
<211> LENGTH: 5009
<212> TYPE: DNA
<213> ORGANISM: artificial
<220> FEATURE:
<223> OTHER INFORMATION: vector pYD1

<400> SEQUENCE: 72

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgcttcagt tttagcacag gaactgacaa     600
ctatatgcga gcaaatcccc tcaccaactt tagaatcgac gccgtactct ttgtcaacga     660
ctactatttt ggccaacggg aaggcaatgc aaggagtttt tgaatattac aaatcagtaa     720
cgtttgtcag taattgcggt tctcaccccct caacaactag caaaggcagc cccataaaca     780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccagtg tggtggaatt ctgcagatat ccagcacagt     960
ggcggccgct cgagtctaga gggcccttcg aaggtaagcc tatccctaac cctctcctcg    1020
gtctcgattc tacgcgtacc ggtcatcatc accatcacca ttgagtttaa acccgctgat    1080
ctgataacaa cagtgtagat gtaacaaaat cgactttgtt cccactgtac ttttagctcg    1140
tacaaaatac aatatacttt tcatttctcc gtaaacaaca tgttttccca tgtaatatcc    1200
ttttctattt ttcgttccgt taccaacttt acacatactt tatatagcta ttcacttcta    1260
tacactaaaa aactaagaca attttaattt tgctgcctgc catatttcaa tttgttataa    1320
attcctataa tttatcctat tagtagctaa aaaaagatga atgtgaatcg aatcctaaga    1380
gaattgggca agtgcacaaa caatacttaa ataaatacta ctcagtaata acctatttct    1440
tagcattttt gacgaaattt gctatttttgt tagagtcttt tacaccattt gtctccacac    1500
ctccgcttac atcaacacca ataacgccat ttaatctaag cgcatcacca acattttctg    1560
gcgtcagtcc accagctaac ataaaatgta agctctcggg ctctcttgc cttccaaccc    1620
agtcagaaat cgagttccaa tccaaaagtt cacctgtccc acctgcttct gaatcaaaca    1680
agggaataaa cgaatgaggt ttctgtgaag ctgcactgag tagtatgttg cagtcttttg    1740
gaaatacgag tctttttaata actggcaaac cgaggaactc ttggtattct tgccacgact    1800
```

```
catctccgtg cagttggacg atatcaatgc cgtaatcatt gaccagagcc aaaacatcct    1860
ccttaggttg attacgaaac acgccaacca agtatttcgg agtgcctgaa ctatttttat    1920
atgcttttac aagacttgaa attttccttg caataaccgg gtcaattgtt ctctttctat    1980
tgggcacaca tataataccc agcaagtcag catcggaatc tagagcacat tctgcggcct    2040
ctgtgctctg caagccgcaa actttcacca atggaccaga actacctgtg aaattaataa    2100
cagacatact ccaagctgcc tttgtgtgct taatcacgta tactcacgtg ctcaatagtc    2160
accaatgccc tccctcttgg ccctctcctt ttcttttttc gaccgaattt cttgaagacg    2220
aaagggcctc gtgatacgcc tatttttata ggttaatgtc atgataataa tggtttctta    2280
ggacggatcg cttgcctgta acttacacgc gcctcgtatc ttttaatgat ggaataattt    2340
gggaatttac tctgtgttta tttatttttta tgttttgtat ttggatttta gaaagtaaat    2400
aaagaaggta gaagagttac ggaatgaaga aaaaaaaata aacaaaggtt taaaaaattt    2460
caacaaaaag cgtactttac atatatattt attagacaag aaaagcagat taaatagata    2520
tacattcgat taacgataag taaaatgtaa aatcacagga ttttcgtgtg tggtcttcta    2580
cacagacaag atgaaacaat tcggcattaa tacctgagag caggaagagc aagataaaag    2640
gtagtatttg ttggcgatcc ccctagagtc ttttacatct tcggaaaaca aaaactattt    2700
tttctttaat ttcttttttt actttctatt tttaatttat atatttatat taaaaaattt    2760
aaattataat tattttata gcacgtgatg aaaaggaccc aggtggcact tttcggggaa    2820
atgtgcgcgg aaccccctatt tgtttatttt tctaaataca ttcaaatatg tatccgctca    2880
tgagacaata accctgataa atgcttcaat aatattgaaa aaggaagagt atgagtattc    2940
aacatttccg tgtcgccctt attccttttt tgcggcattt tgccttcct gtttttgctc    3000
acccagaaac gctggtgaaa gtaaaagatg ctgaagatca gttgggtgca cgagtgggtt    3060
acatcgaact ggatctcaac agcggtaaga tccttgagag ttttcgcccc gaagaacgtt    3120
ttccaatgat gagcactttt aaagttctgc tatgtggcgc ggtattatcc cgtgttgacg    3180
ccgggcaaga gcaactcggt cgccgcatac actattctca gaatgacttg gttgagtact    3240
caccagtcac agaaaagcat cttacggatg gcatgacagt aagagaatta tgcagtgctg    3300
ccataaccat gagtgataac actgcggcca acttacttct gacaacgatc ggaggaccga    3360
aggagctaac cgcttttttg cacaacatgg gggatcatgt aactcgcctt gatcgttggg    3420
aaccggagct gaatgaagcc ataccaaacg acgagcgtga ccacgatg cctgtagcaa    3480
tggcaacaac gttgcgcaaa ctattaactg gcgaactact tactctagct tcccggcaac    3540
aattaataga ctggatggag gcggataaag ttgcaggacc acttctgcgc tcggcccttc    3600
cggctggctg gtttattgct gataaatctg gagccggtga gcgtgggtct cgcggtatca    3660
ttgcagcact ggggccagat ggtaagccct cccgtatcgt agttatctac acgacgggca    3720
gtcaggcaac tatggatgaa cgaaatagac agatcgctga gataggtgcc tcactgatta    3780
agcattggta actgtcagac caagtttact catatatact ttagattgat ttaaaacttc    3840
atttttaatt taaaaggatc taggtgaaga tccttttga taatctcatg accaaaatcc    3900
cttaacgtga gttttcgttc cactgagcgt cagaccccgt agaaaagatc aaaggatctt    3960
cttgagatcc ttttttttctg cgcgtaatct gctgcttgca acaaaaaaa ccaccgctac    4020
cagcggtggt ttgtttgccg gatcaagagc taccaactct ttttccgaag gtaactggct    4080
tcagcagagc gcagatacca atactgtcc ttctagtgta gccgtagtta ggccaccact    4140
tcaagaactc tgtagcaccg cctacatacc tcgctctgct aatcctgtta ccagtggctg    4200
```

```
ctgccagtgg cgataagtcg tgtcttaccg ggttggactc aagacgatag ttaccggata    4260
aggcgcagcg gtcgggctga acgggggggtt cgtgcacaca gcccagcttg gagcgaacga    4320
cctacaccga actgagatac ctacagcgtg agcattgaga aagcgccacg cttcccgaag    4380
ggagaaaggc ggacaggtat ccggtaagcg gcagggtcgg aacaggagag cgcacgaggg    4440
agcttccagg ggggaacgcc tggtatcttt atagtcctgt cgggtttcgc cacctctgac    4500
ttgagcgtcg attttttgtga tgctcgtcag ggggccgag cctatggaaa aacgccagca    4560
acgcggcctt tttacggttc ctggcctttt gctggccttt tgctcacatg ttctttcctg    4620
cgttatcccc tgattctgtg gataaccgta ttaccgcctt tgagtgagct gataccgctc    4680
gccgcagccg aacgaccgag cgcagcgagt cagtgagcga ggaagcggaa gagcgcccaa    4740
tacgcaaacc gcctctcccc gcgcgttggc cgattcatta atgcagctgg cacgacaggt    4800
ttcccgactg gaaagcgggc agtgagcgca acgcaattaa tgtgagttac ctcactcatt    4860
aggcacccca ggctttacac tttatgcttc cggctcctat gttgtgtgga attgtgagcg    4920
gataacaatt tcacacagga aacagctatg accatgatta cgccaagctc ggaattaacc    4980
ctcactaaag ggaacaaaag ctggctagt                                     5009

<210> SEQ ID NO 73
<211> LENGTH: 5009
<212> TYPE: DNA
<213> ORGANISM: artificial
<220> FEATURE:
<223> OTHER INFORMATION: modified vector pYD1Nhe

<400> SEQUENCE: 73
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240 ttagttttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgcttcagt gctagcacag gaactgacaa     600
ctatatgcga gcaaatcccc tcaccaactt tagaatcgac gccgtactct tgtcaacga     660 ctactatttt ggccaacggg aaggcaatgc aaggagtttt tgaatattac aaatcagtaa     720
cgtttgtcag taattgcggt tctcaccccct caacaactag caaaggcagc cccataaaca     780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccagtg tggtggaatt ctgcagatat ccagcacagt     960
ggcggccgct cgagtctaga gggcccttcg aaggtaagcc tatccctaac cctctcctcg    1020
gtctcgattc tacgcgtacc ggtcatcatc accatcacca ttgagtttaa acccgctgat    1080
ctgataacaa cagtgtagat gtaacaaaat cgactttgtt cccactgtac ttttagctcg    1140
tacaaaatac aatatacttt tcatttctcc gtaaacaaca tgttttccca tgtaatatcc    1200
```

```
ttttctattt ttcgttccgt taccaacttt acacatactt tatatagcta ttcacttcta    1260
tacactaaaa aactaagaca attttaattt tgctgcctgc catatttcaa tttgttataa    1320
attcctataa tttatcctat tagtagctaa aaaaagatga atgtgaatcg aatcctaaga    1380
gaattgggca agtgcacaaa caatacttaa ataaatacta ctcagtaata acctatttct    1440
tagcattttt gacgaaattt gctattttgt tagagtcttt tacaccattt gtctccacac    1500
ctccgcttac atcaacacca ataacgccat ttaatctaag cgcatcacca acattttctg    1560
gcgtcagtcc accagctaac ataaaatgta agctctcggg gctctcttgc cttccaaccc    1620
agtcagaaat cgagttccaa tccaaaagtt cacctgtccc acctgcttct gaatcaaaca    1680
agggaataaa cgaatgaggt ttctgtgaag ctgcactgag tagtatgttg cagtcttttg    1740
gaaatacgag tcttttaata actggcaaac cgaggaactc ttggtattct tgccacgact    1800
catctccgtg cagttggacg atatcaatgc cgtaatcatt gaccagagcc aaaacatcct    1860
ccttaggttg attacgaaac acgccaacca agtatttcgg agtgcctgaa ctatttttat    1920
atgcttttac aagacttgaa attttccttg caataaccgg gtcaattgtt ctctttctat    1980
tgggcacaca tataataccc agcaagtcag catcggaatc tagagcacat tctgcggcct    2040
ctgtgctctg caagccgcaa actttcacca atggaccaga actacctgtg aaattaataa    2100
cagacatact ccaagctgcc tttgtgtgct taatcacgta tactcacgtg ctcaatagtc    2160
accaatgccc tccctcttgg ccctctcctt ttctttttc gaccgaattt cttgaagacg    2220
aaagggcctc gtgatacgcc tatttttata ggttaatgtc atgataataa tggtttctta    2280
ggacggatcg cttgcctgta acttacacgc gcctcgtatc ttttaatgat ggaataattt    2340
gggaatttac tctgtgttta tttattttta tgttttgtat ttggatttta gaaagtaaat    2400
aaagaaggta gaagagttac ggaatgaaga aaaaaaaata aacaaggtt taaaaaattt    2460 caacaaaaag cgtactttac atatatattt attagacaag aaaagcagat taaatagata    2520
tacattcgat taacgataag taaaatgtaa aatcacagga ttttcgtgtg tggtcttcta    2580
cacagacaag atgaaacaat tcggcattaa tacctgagag caggaagagc aagataaaag    2640
gtagtatttg ttggcgatcc ccctagagtc ttttacatct tcggaaaaca aaaactattt    2700
tttctttaat ttctttttt actttctatt tttaatttat atatttatat taaaaatttt    2760
aaattataat tatttttata gcacgtgatg aaaaggaccc aggtggcact tttcggggaa    2820
atgtgcgcgg aaccctctatt tgtttattttt tctaaataca ttcaaatatg tatccgctca    2880
tgagacaata accctgataa atgcttcaat aatattgaaa aaggaagagt atgagtattc    2940
aacatttccg tgtcgccctt attcccttttt ttgcggcatt ttgccttcct gtttttgctc    3000
acccagaaac gctggtgaaa gtaaaagatg ctgaagatca gttgggtgca cgagtgggtt    3060
acatcgaact ggatctcaac agcggtaaga tccttgagag ttttcgcccc gaagaacgtt    3120
ttccaatgat gagcactttt aaagttctgc tatgtggcgc ggtattatcc cgtgttgacg    3180
ccgggcaaga gcaactcggt cgccgcatac actattctca gaatgacttg gttgagtact    3240
caccagtcac agaaaagcat cttacggatg gcatgacagt aagagaatta tgcagtgctg    3300
ccataaccat gagtgataac actgcggcca acttacttct gacaacgatc ggaggaccga    3360
aggagctaac cgcttttttg cacaacatgg gggatcatgt aactcgcctt gatcgttggg    3420
aaccggagct gaatgaagcc ataccaaacg acgagcgtga caccacgatg cctgtagcaa    3480
tggcaacaac gttgcgcaaa ctattaactg gcgaactact tactctagct tcccggcaac    3540
aattaataga ctggatggag gcggataaag ttgcaggacc acttctgcgc tcggcccttc    3600
```

```
cggctggctg gtttattgct gataaatctg gagccggtga gcgtgggtct cgcggtatca    3660
ttgcagcact ggggccagat ggtaagccct cccgtatcgt agttatctac acgacgggca    3720
gtcaggcaac tatggatgaa cgaaatagac agatcgctga gataggtgcc tcactgatta    3780
agcattggta actgtcagac caagtttact catatatact ttagattgat ttaaaacttc    3840 attttaatt taaaaggatc taggtgaaga tcctttttga taatctcatg accaaaatcc    3900
cttaacgtga gttttcgttc cactgagcgt cagaccccgt agaaaagatc aaaggatctt    3960
cttgagatcc ttttttctg cgcgtaatct gctgcttgca acaaaaaaa ccaccgctac    4020 cagcggtggt ttgtttgccg gatcaagagc taccaactct ttttccgaag gtaactggct    4080
tcagcagagc gcagatacca aatactgtcc ttctagtgta gccgtagtta ggccaccact    4140
tcaagaactc tgtagcaccg cctacatacc tcgctctgct aatcctgtta ccagtggctg    4200
ctgccagtgg cgataagtcg tgtcttaccg ggttggactc aagacgatag ttaccggata    4260
aggcgcagcg gtcgggctga acggggggtt cgtgcacaca gcccagcttg gagcgaacga    4320
cctacaccga actgagatac ctacagcgtg agcattgaga aagcgccacg cttcccgaag    4380
ggagaaaggc ggacaggtat ccggtaagcg gcagggtcgg aacaggagag cgcacgaggg    4440
agcttccagg ggggaacgcc tggtatcttt atagtcctgt cgggtttcgc cacctctgac    4500
ttgagcgtcg attttgtga tgctcgtcag ggggccgag cctatggaaa aacgccagca    4560
acgcggcctt tttacggttc ctggcctttt gctggccttt tgctcacatg ttctttcctg    4620
cgttatcccc tgattctgtg gataaccgta ttaccgcctt tgagtgagct gataccgctc    4680
gccgcagccg aacgaccgag cgcagcgagt cagtgagcga ggaagcggaa gagcgcccaa    4740
tacgcaaacc gcctctcccc gcgcgttggc cgattcatta atgcagctgg cacgacaggt    4800
ttcccgactg gaaagcgggc agtgagcgca acgcaattaa tgtgagttac ctcactcatt    4860
aggcacccca ggctttacac tttatgcttc cggctcctat gttgtgtgga attgtgagcg    4920
gataacaatt tcacacagga aacagctatg accatgatta cgccaagctc ggaattaacc    4980
ctcactaaag ggaacaaaag ctggctagt                                     5009
```

<210> SEQ ID NO 74
<211> LENGTH: 4605
<212> TYPE: DNA
<213> ORGANISM: artificial
<220> FEATURE:
<223> OTHER INFORMATION: vector pYD11nk

<400> SEQUENCE: 74

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagcttta tggttatgaa gaggaaaaat tggcagtaac      180
ctggccccac aaaccttcaa atgaacgaat caaattaaca accataggat gataatgcga     240 ttagttttt agccttattt ctggggtaat taatcagcga agcgatgatt tttgatctat      300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac atttcaatt aagatgcagt      540 tacttcgctg tttttcaata ttttctgtta ttgcttcagt gctagccgct ggggccatgg      600
```

```
ttactgattg gcgcgccgga tccttcagac tctgcagaat tcggccgcgt acttaattaa      660
gtttaaaccc gctgatctga taacaacagt gtagatgtaa caaatcgac tttgttccca       720
ctgtactttt agctcgtaca aatacaata tacttttcat ttctccgtaa acaacatgtt       780
ttcccatgta atatccttt ctattttcg ttccgttacc aactttacac atactttata       840
tagctattca cttctataca ctaaaaaact aagacaattt taattttgct gcctgccata      900
tttcaatttg ttataaattc ctataattta tcctattagt agctaaaaaa agatgaatgt      960
gaatcgaatc ctaagagaat tgggcaagtg cacaaacaat acttaaataa atactactca     1020
gtaataaccct atttcttagc attttttgacg aaatttgcta ttttgttaga gtcttttaca   1080
ccatttgtct ccacacctcc gcttacatca acaccaataa cgccatttaa tctaagcgca     1140
tcaccaacat tttctggcgt cagtccacca gctaacataa aatgtaagct ctcggggctc     1200
tcttgccttc caacccagtc agaaatcgag ttccaatcca aaagttcacc tgtcccacct     1260
gcttctgaat caaacaaggg aataaacgaa tgaggtttct gtgaagctgc actgagtagt     1320
atgttgcagt cttttggaaa tacgagtctt ttaataactg gcaaaccgag gaactcttgg     1380
tattcttgcc acgactcatc tccgtgcagt tggacgatat caatgccgta atcattgacc     1440
agagccaaaa catcctcctt aggttgatta cgaaacacgc caaccaagta tttcggagtg     1500
cctgaactat tttatatgc ttttacaaga cttgaaattt tccttgcaat aaccgggtca     1560
attgttctct ttctattggg cacacatata atacccagca agtcagcatc ggaatctaga    1620
gcacattctg cggcctctgt gctctgcaag ccgcaaactt tcaccaatgg accagaacta    1680
cctgtgaaat aataacaga catactccaa gctgcctttg tgtgcttaat cacgtatact     1740
cacgtgctca atagtcacca atgccctccc tcttggccct ctccttttct ttttcgacc     1800
gaatttcttg aagacgaaag ggcctcgtga tacgcctatt tttataggtt aatgtcatga    1860
taataatggt ttcttaggac ggatcgcttg cctgtaactt acacgcgcct cgtatctttt    1920
aatgatggaa taatttggga atttactctg tgtttatta tttttatgtt ttgtatttgg     1980
attttagaaa gtaaataaag aaggtagaag agttacggaa tgaagaaaaa aaaataaaca   2040
aaggtttaaa aaatttcaac aaaaagcgta ctttacatat atatttatta gacaagaaaa   2100
gcagattaaa tagatatca ttcgattaac gataagtaaa atgtaaaatc acaggatttt    2160
cgtgtgtggt cttctacaca gacaagatga aacaattcgg cattaatacc tgagagcagg    2220
aagagcaaga taaaggtag tatttgttgg cgatcccct agagtctttt acatcttcgg     2280
aaaacaaaaa ctatttttc tttaatttct tttttacctt tctatttta atttatata      2340
ttatattaaa aaatttaaat tataattatt tttatagcac gtgatgaaaa ggacccaggt    2400
ggcacttttc ggggaaatgt gcgcggaacc cctatttgtt tattttttcta aatacattca   2460
aatatgtatc cgctcatgag acaataaccc tgataaatgc ttcaataata ttgaaaaagg    2520
aagagtatga gtattcaaca tttccgtgtc gcccttattc ccttttttgc ggcattttgc    2580
cttcctgttt ttgctcaccc agaaacgctg gtgaaagtaa aagatgctga agatcagttg    2640
ggtgcacgag tgggttacat cgaactggat ctcaacagcg gtaagatcct tgagagtttt   2700
cgccccgaag aacgttttcc aatgatgagc acttttaaag ttctgctatg tggcgcggta    2760
ttatcccgtg ttgacgccgg gcaagagcaa ctcggtcgcc gcatacacta ttctcagaat    2820
gacttggttg agtactcacc agtcacagaa aagcatctta cggatggcat gacagtaaga    2880
gaattatgca gtgctgccat aaccatgagt gataacactg cggccaactt acttctgaca    2940
acgatcggag gaccgaagga gctaaccgct tttttgcaca acatggggga tcatgtaact    3000
```

```
cgccttgatc gttgggaacc ggagctgaat gaagccatac caaacgacga gcgtgacacc    3060
acgatgcctg tagcaatggc aacaacgttg cgcaaactat taactggcga actacttact    3120
ctagcttccc ggcaacaatt aatagactgg atggaggcgg ataaagttgc aggaccactt    3180
ctgcgctcgg cccttccggc tggctggttt attgctgata atctggagc cggtgagcgt    3240 gggtctcgcg gtatcattgc agcactgggg ccagatggta agccctcccg tatcgtagtt    3300
atctacacga cgggcagtca ggcaactatg gatgaacgaa atagacagat cgctgagata    3360
ggtgcctcac tgattaagca ttggtaactg tcagaccaag tttactcata tatactttag    3420
attgatttaa aacttcattt ttaatttaaa aggatctagg tgaagatcct ttttgataat    3480
ctcatgacca aaatccctta acgtgagttt tcgttccact gagcgtcaga ccccgtagaa    3540
aagatcaaag gatcttcttg agatcctttt tttctgcgcg taatctgctg cttgcaaaca    3600
aaaaaaccac cgctaccagc ggtggtttgt ttgccggatc aagagctacc aactcttttt    3660
ccgaaggtaa ctggcttcag cagagcgcag ataccaaata ctgtccttct agtgtagccg    3720
tagttaggcc accacttcaa gaactctgta gcaccgccta catacctcgc tctgctaatc    3780
ctgttaccag tggctgctgc cagtggcgat aagtcgtgtc ttaccgggtt ggactcaaga    3840
cgatagttac cggataaggc gcagcggtcg ggctgaacgg ggggttcgtg cacacagccc    3900
agcttggagc gaacgaccta caccgaactg agatacctac agcgtgagca ttgagaaagc    3960
gccacgcttc ccgaagggag aaaggcggac aggtatccgg taagcggcag ggtcggaaca    4020
ggagagcgca cgagggagct tccagggggg aacgcctggt atctttatag tcctgtcggg    4080
tttcgccacc tctgacttga gcgtcgattt ttgtgatgct cgtcaggggg gcggagccta    4140
tggaaaaacg ccagcaacgc ggcctttttta cggttcctgg ccttttgctg gccttttgct    4200
cacatgttct ttcctgcgtt atcccctgat tctgtggata accgtattac cgcctttgag    4260
tgagctgata ccgctcgccg cagccgaacg accgagcgca gcgagtcagt gagcgaggaa    4320
gcggaagagc gcccaatacg caaaccgcct ctccccgcgc gttggccgat tcattaatgc    4380
agctggcacg acaggtttcc cgactggaaa gcgggcagtg agcgcaacgc aattaatgtg    4440
agttacctca ctcattaggc accccaggct ttacacttta tgcttccggc tcctatgttg    4500
tgtggaattg tgagcggata acaatttcac acaggaaaca gctatgacca tgattacgcc    4560
aagctcggaa ttaaccctca ctaaagggaa caaaagctgg ctagt                    4605
```

<210> SEQ ID NO 75
<211> LENGTH: 4886
<212> TYPE: DNA
<213> ORGANISM: artificial
<220> FEATURE:
<223> OTHER INFORMATION: vector pYD1mata

<400> SEQUENCE: 75

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
```

```
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgcttcagt gctagccgct ggggccatgg    600
ttactgattg gcgcgccgga tccgatgtaa caaaatcgac tttgttccca ctgtactttt    660
agctcgtaca aaatacaata tacttttcat ttctccgtaa caacatgtt ttcccatgta    720 atatcctttt ctattttcg ttccgttacc aactttacac atactttata tagctattca    780
cttctataca ctaaaaaact aagacaattt taattttgct gcctgccata tttcaatttg    840
ttataaattc ctataattta tcctattagt agctaaaaaa agatgaatgt gaatcgaatc    900
ctaagagaat tgctgcagaa ttcggccgcg tacttaatta agtttaaacc cgctgatctg    960
ataacaacag tgtagatgta acaaaatcga ctttgttccc actgtacttt tagctcgtac   1020
aaaatacaat atacttttca tttctccgta acaacatgt tttcccatgt aatatccttt   1080 tctattttc gttccgttac caactttaca catactttat atagctattc acttctatac   1140
actaaaaaac taagacaatt ttaattttgc tgcctgccat atttcaattt gttataaatt   1200
cctataattt atcctattag tagctaaaaa aagatgaatg tgaatcgaat cctaagagaa   1260 tgggcaagt gcacaaacaa tacttaaata aatactactc agtaataacc tatttcttag   1320 cattttgac gaaatttgct attttgttag agtcttttac accatttgtc tccacacctc   1380
cgcttacatc aacaccaata acgccattta atctaagcgc atcaccaaca ttttctggcg   1440
tcagtccacc agctaacata aaatgtaagc tctcggggct ctcttgcctt ccaacccagt   1500
cagaaatcga gttccaatcc aaaagttcac ctgtcccacc tgcttctgaa tcaaacaagg   1560
gaataaacga atgaggtttc tgtgaagctg cactgagtag tatgttgcag tcttttggaa   1620
atacgagtct tttaataact ggcaaaccga ggaactcttg gtattcttgc cacgactcat   1680
ctccgtgcag ttggacgata tcaatgccgt aatcattgac cagagccaaa acatcctcct   1740
taggttgatt acgaaacacg ccaaccaagt atttcggagt gcctgaacta ttttatatg    1800 cttttacaag acttgaaatt ttccttgcaa taaccgggtc aattgttctc tttctattgg   1860
gcacacatat aatacccagc aagtcagcat cggaatctag agcacattct gcggcctctg   1920
tgctctgcaa gccgcaaact ttcaccaatg gaccagaact acctgtgaaa ttaataacag   1980
acatactcca agctgccttt gtgtgcttaa tcacgtatac tcacgtgctc aatagtcacc   2040
aatgccctcc ctcttggccc tctccttttc ttttttcgac cgaatttctt gaagacgaaa   2100
gggcctcgtg atacgcctat ttttataggt taatgtcatg ataataatgg tttcttagga   2160
cggatcgctt gcctgtaact tacacgcgcc tcgtatcttt taatgatgga ataatttggg   2220
aatttactct gtgtttattt atttttatgt tttgtatttg gatttagaa agtaaataaa   2280 gaaggtagaa gagttacgga atgaagaaaa aaaataaac aaaggtttaa aaaatttcaa   2340
caaaaagcgt actttacata tatatttatt agacaagaaa agcagattaa atagatatac   2400
attcgattaa cgataagtaa aatgtaaaat cacaggattt tcgtgtgtgg tcttctacac   2460
agacaagatg aaacaattcg gcattaatac ctgagagcag aagagcaag ataaaaggta   2520 gtatttgttg gcgatccccc tagagtcttt tacatcttcg gaaaacaaaa actatttttt   2580
ctttaatttc tttttttact ttctattttt aatttatata tttatattaa aaaatttaaa   2640
ttataattat ttttatagca cgtgatgaaa aggacccagg tggcacttt cggggaaatg   2700 tgcgcggaac ccctatttgt ttatttttct aaatacattc aaatatgtat ccgctcatga   2760
gacaataacc ctgataaatg cttcaataat attgaaaaag gaagagtatg agtattcaac   2820
```

```
atttccgtgt cgcccttatt ccctttttg cggcattttg ccttcctgtt tttgctcacc    2880
cagaaacgct ggtgaaagta aaagatgctg aagatcagtt gggtgcacga gtgggttaca    2940
tcgaactgga tctcaacagc ggtaagatcc ttgagagttt tcgccccgaa gaacgttttc    3000
caatgatgag cacttttaaa gttctgctat gtggcgcggt attatcccgt gttgacgccg    3060
ggcaagagca actcggtcgc cgcatacact attctcagaa tgacttggtt gagtactcac    3120
cagtcacaga aaagcatctt acggatggca tgacagtaag agaattatgc agtgctgcca    3180
taaccatgag tgataacact gcggccaact tacttctgac aacgatcgga ggaccgaagg    3240
agctaaccgc ttttttgcac aacatggggg atcatgtaac tcgccttgat cgttgggaac    3300
cggagctgaa tgaagccata ccaaacgacg agcgtgacac cacgatgcct gtagcaatgg    3360
caacaacgtt gcgcaaacta ttaactggcg aactacttac tctagcttcc cggcaacaat    3420
taatagactg gatggaggcg gataaagttg caggaccact tctgcgctcg gcccttccgg    3480
ctggctggtt tattgctgat aaatctggag ccggtgagcg tgggtctcgc ggtatcattg    3540
cagcactggg gccagatggt aagccctccc gtatcgtagt tatctacacg acgggcagtc    3600
aggcaactat ggatgaacga atagacaga tcgctgagat aggtgcctca ctgattaagc    3660
attggtaact gtcagaccaa gtttactcat atatacttta gattgattta aaacttcatt    3720
tttaatttaa aaggatctag gtgaagatcc ttttttgataa tctcatgacc aaaatccctt    3780
aacgtgagtt ttcgttccac tgagcgtcag accccgtaga aaagatcaaa ggatcttctt    3840
gagatccttt ttttctgcgc gtaatctgct gcttgcaaac aaaaaaacca ccgctaccag    3900
cggtggtttg tttgccggat caagagctac caactctttt tccgaaggta actggcttca    3960
gcagagcgca gataccaaat actgtccttc tagtgtagcc gtagttaggc caccacttca    4020
agaactctgt agcaccgcct acatacctcg ctctgctaat cctgttacca gtggctgctg    4080
ccagtggcga taagtcgtgt cttaccgggt tggactcaag acgatagtta ccggataagg    4140
cgcagcggtc gggctgaacg gggggttcgt gcacacagcc cagcttggag cgaacgacct    4200
acaccgaact gagataccta cagcgtgagc attgagaaag cgccacgctt cccgaaggga    4260
gaaaggcgga caggtatccg gtaagcggca gggtcggaac aggagagcgc acgagggagc    4320 ttccagggg gaacgcctgg tatctttata gtcctgtcgg gtttcgccac ctctgacttg    4380
agcgtcgatt tttgtgatgc tcgtcagggg ggcgagcct atggaaaaac gccagcaacg    4440
cggccttttt acggttcctg gccttttgct ggccttttgc tcacatgttc tttcctgcgt    4500 tatccctga ttctgtggat aaccgtatta ccgcctttga gtgagctgat accgctcgcc    4560
gcagccgaac gaccgagcgc agcgagtcag tgagcgagga agcggaagag cgcccaatac    4620
gcaaaccgcc tctccccgcg cgttggccga ttcattaatg cagctggcac gacaggtttc    4680
ccgactggaa agcgggcagt gagcgcaacg caattaatgt gagttacctc actcattagg    4740
cacccccagc tttacacttt atgcttccgg ctccatgtt gtgtggaatt gtgagcggat    4800
aacaatttca cacaggaaac agctatgacc atgattacgc caagctcgga attaaccctc    4860
actaagggga acaaaagctg gctagt                                        4886
```

<210> SEQ ID NO 76
<211> LENGTH: 5801
<212> TYPE: DNA
<213> ORGANISM: artificial
<220> FEATURE:
<223> OTHER INFORMATION: vector pYD1gal

```
<400> SEQUENCE: 76
acggattaga agccgccgag cgggtgacag ccctccgaag gaagactctc ctccgtgcgt    60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagttttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caaatgtaat aaaagtatca acaaaaaatt gttaatatac   420
ctctatactt taacgtcaag gagaaaaaac cccggatcgg actactagca gctgtaatac   480
gactcactat agggaatatt aagctaattc tacttcatac attttcaatt aagatgcagt   540
tacttcgctg ttttttcaata ttttctgtta ttgcttcagt gctagccgct ggggccatgg   600
ttactgattg gcgcgccgga tccgatgtaa caaaatcgac tttgttccca ctgtactttt   660
agctcgtaca aaatacaata tacttttcat ttctccgtaa acaacatgtt ttcccatgta   720
atatcctttt ctattttttcg ttccgttacc aactttacac atactttata tagctattca   780
cttctataca ctaaaaaact aagacaattt taattttgct gcctgccata tttcaatttg   840
ttataaattc ctataattta tcctattagt agctaaaaaa agatgaatgt gaatcgaatc   900
ctaagagaat tgctgcagaa ttcacggatt agaagccgcc gagcgggtga cagccctccg   960
aaggaagact ctcctccgtg cgtcctcgtc ttcaccggtc gcgttcctga aacgcagatg  1020
tgcctcgcgc cgcactgctc cgaacaataa agattctaca atactagctt ttatggttat  1080
gaagaggaaa aattggcagt aacctggccc cacaaacctt caaatgaacg aatcaaatta  1140
acaaccatag gatgataatg cgattagttt ttttagcctta tttctggggt aattaatcag  1200
cgaagcgatg attttttgatc tattaacaga tatataaatg caaaaactgc ataaccactt  1260
taactaatac tttcaacatt ttcggtttgt attacttctt attcaaatgt aataaaagta  1320
tcaacaaaaa attgttaata tacctctata ctttaacgtc aaggagaaaa aaccccggat  1380
cggactacta gcagctgtaa tacgactcac tatagggaat attaagctaa ttctacttca  1440
tacattttca attaagatgc agttacttcg ctgttttttca atattttctg ttattgcttc  1500
agttttagca caggaactga caactatatg cgagcaaatc ccctcaccaa ctttagaatc  1560
gacgccgtac tctttgtcaa cgactactat tttggccaac gggaaggcaa tgcaaggagt  1620
ttttgaatat tacaaatcag taacgtttgt cagtaattgc ggttctcacc cctcaacaac  1680
tagcaaaggc agccccataa acacacagta tgttttttaag cttctgcagg ctagtggtgg  1740
tggtggttct ggtggtggtg gttctggtgg tggtggttct gctagcatga ctggtggcca  1800
gcaaggccta attctgatgc ggccgcacat catcaccatc accattgatt aattaagttt  1860
aaacccgctg atctgataac aacagtgtag atgtaacaaa atcgactttg ttcccactgt  1920
acttttagct cgtacaaaat acaatatact tttcatttct ccgtaaacaa catgttttcc  1980
catgtaatat ccttttctat tttttcgttcc gttaccaact ttacacatac tttatatagc  2040
tattcacttc tatacactaa aaaactaaga caatttttaat tttgctgcct gccatatttc  2100
aatttgttat aaattcctat aatttatcct attagtagct aaaaaagat gaatgtgaat  2160
cgaatcctaa gagaattggg caagtgcaca acaatactt aaataaatac tactcagtaa  2220
taacctatttt cttagcattt ttgacgaaat ttgctatttt gttagagtct tttacaccat  2280
ttgtctccac acctccgctt acatcaacac caataacgcc atttaatcta agcgcatcac  2340
```

```
caacattttc tggcgtcagt ccaccagcta acataaaatg taagctctcg gggctctctt    2400
gccttccaac ccagtcagaa atcgagttcc aatccaaaag ttcacctgtc ccacctgctt    2460
ctgaatcaaa caaggaata aacgaatgag gtttctgtga agctgcactg agtagtatgt    2520
tgcagtcttt tggaaatacg agtcttttaa taactggcaa accgaggaac tcttggtatt    2580
cttgccacga ctcatctccg tgcagttgga cgatatcaat gccgtaatca ttgaccagag    2640
ccaaaacatc ctccttaggt tgattacgaa acacgccaac caagtatttc ggagtgcctg    2700 aactatttt atatgctttt acaagacttg aaattttcct tgcaataacc gggtcaattg    2760
ttctctttct attgggcaca catataatac ccagcaagtc agcatcggaa tctagagcac    2820
attctgcggc ctctgtgctc tgcaagccgc aaactttcac caatggacca gaactacctg    2880
tgaaattaat aacagacata ctccaagctg cctttgtgtg cttaatcacg tatactcacg    2940
tgctcaatag tcaccaatgc cctccctctt ggccctctcc ttttctttt tcgaccgaat    3000 ttcttgaaga cgaaagggcc tcgtgatacg cctatttta taggttaatg tcatgataat    3060
aatggtttct taggacggat cgcttgcctg taacttacac gcgcctcgta tcttttaatg    3120
atggaataat ttgggaattt actctgtgtt tatttatttt tatgttttgt atttggattt    3180
tagaaagtaa ataagaagg tagaagagtt acggaatgaa gaaaaaaaa taaacaaagg    3240 tttaaaaat ttcaacaaaa agcgtactttt acatatatat ttattagaca agaaaagcag    3300
attaaataga tatacattcg attaacgata agtaaaatgt aaaatcacag gattttcgtg    3360
tgtggtcttc tacacagaca agatgaaaca attcggcatt aatacctgag agcaggaaga    3420
gcaagataaa aggtagtatt tgttggcgat ccccctagag tcttttacat cttcggaaaa    3480
caaaaactat ttttctttta atttctttt ttactttcta ttttaatttt atatatttat    3540
attaaaaaat ttaaattata attatttta tagcacgtga tgaaaggac ccaggtggca    3600 cttttcgggg aaatgtgcgc ggaaccccta tttgtttatt tttctaaata cattcaaata    3660
tgtatccgct catgagacaa taaccctgat aaatgcttca ataatattga aaaggaaga    3720 gtatgagtat tcaacatttc cgtgtcgccc ttattccctt ttttgcggca ttttgccttc    3780 ctgttttgc tcacccagaa acgctggtga agtaaaaga tgctgaagat cagttgggtg    3840
cacgagtggg ttacatcgaa ctggatctca acagcggtaa gatccttgag agttttcgcc    3900
ccgaagaacg ttttccaatg atgagcactt ttaaagttct gctatgtggc gcggtattat    3960
cccgtgttga cgccgggcaa gagcaactcg gtcgccgcat acactattct cagaatgact    4020
tggttgagta ctcaccagtc acagaaaagc atcttacgga tggcatgaca gtaagagaat    4080
tatgcagtgc tgccataacc atgagtgata acactgcggc caacttactt ctgacaacga    4140
tcggaggacc gaaggagcta accgcttttt tgcacaacat ggggatcat gtaactcgcc    4200 ttgatcgttg ggaaccggag ctgatgaag ccataccaaa cgacgagcgt gacaccacga    4260
tgcctgtagc aatggcaaca acgttgcgca aactattaac tggcgaacta cttactctag    4320
cttcccggca acaattaata gactggatgg aggcggataa agttgcagga ccacttctgc    4380
gctcggccct tccggctggc tggtttattg ctgataaatc tggagccggt gagcgtgggt    4440
ctcgcggtat cattgcagca ctggggccag atggtaagcc ctcccgtatc gtagttatct    4500
acacgacggg cagtcaggca actatggatg aacgaaatag acagatcgct gagataggtg    4560
cctcactgat taagcattgg taactgtcag accaagttta ctcatatata ctttagattg    4620
atttaaaact tcatttttaa tttaaaagga tctaggtgaa gatccttttt gataatctca    4680
```

```
tgaccaaaat cccttaacgt gagttttcgt tccactgagc gtcagacccc gtagaaaaga    4740
tcaaaggatc ttcttgagat ccttttttc tgcgcgtaat ctgctgcttg caaacaaaaa     4800
aaccaccgct accagcggtg gtttgtttgc cggatcaaga gctaccaact cttttccga     4860 aggtaactgg cttcagcaga gcgcagatac caaatactgt ccttctagtg tagccgtagt    4920
taggccacca cttcaagaac tctgtagcac cgcctacata cctcgctctg ctaatcctgt    4980
taccagtggc tgctgccagt ggcgataagt cgtgtcttac cgggttggac tcaagacgat    5040
agttaccgga taaggcgcag cggtcgggct gaacggggg ttcgtgcaca cagcccagct     5100
tggagcgaac gacctacacc gaactgagat acctacagcg tgagcattga aaagcgcca     5160 cgcttcccga agggagaaag gcggacaggt atccggtaag cggcagggtc ggaacaggag    5220
agcgcacgag ggagcttcca gggggaacg cctggtatct ttatagtcct gtcgggtttc     5280
gccacctctg acttgagcgt cgattttgt gatgctcgtc agggggccg agcctatgga      5340 aaaacgccag caacgcggcc ttttacggt tcctggcctt ttgctggcct tttgctcaca     5400
tgttctttcc tgcgttatcc cctgattctg tggataaccg tattaccgcc tttgagtgag    5460
ctgataccgc tcgccgcagc cgaacgaccg agcgcagcga gtcagtgagc gaggaagcgg    5520
aagagcgccc aatacgcaaa ccgcctctcc ccgcgcgttg gccgattcat taatgcagct    5580
ggcacgacag gtttcccgac tggaaagcgg gcagtgagcg caacgcaatt aatgtgagtt    5640
acctcactca ttaggcaccc caggctttac actttatgct tccggctcct atgttgtgtg    5700
gaattgtgag cggataacaa tttcacacag gaaacagcta tgaccatgat tacgccaagc    5760
tcggaattaa ccctcactaa agggaacaaa agctggctag t                        5801
```

<210> SEQ ID NO 77
<211> LENGTH: 692
<212> TYPE: DNA
<213> ORGANISM: artificial
<220> FEATURE:
<223> OTHER INFORMATION: 4D5H

<400> SEQUENCE: 77

```
ggccagcaag gccaagaggt tcaactagtg gagtctggcg gtggcctggt gcagccaggg      60
ggctcactcc gtttgtcctg tgcagcttct ggcttcaaca ttaaagacac ctatatacac     120
tgggtgcgtc aggccccggg taagggcctg gaatgggttg caaggattta tcctacgaat     180
ggttatacta gatatgccga tagcgtcaag ggccgtttca ctataagcgc agacacatcc     240
aaaaacacag cctacctgca gatgaacagc ctgcgtgctg aggacactgc cgtctattat     300
tgttctagat ggggagggga cggcttctat gctatggact actggggtca aggaaccctg     360
gtcaccgtct cctcggctag caccaagggc cccagcgtgt tccctctggc ccccagctcc     420
aagagcacct ccggcggcac cgccgccctg ggctgcctgg tgaaggatta cttcccagag     480
cccgtgaccg tgagctggaa cagcggcgcc ctgaccagcg gcgtgcacac ctttcccgcc     540
gtgctgcagt ccagcggcct gtactccctg agcagcgtgg tgaccgtgcc cagcagcagc    600
ctgggcaccc agacctacat ctgcaatgtg aaccacaagc ccagcaatac caaggtggat    660
aagaaggtgg agcccaagag ctgcgcggcc gc                                  692
```

<210> SEQ ID NO 78
<211> LENGTH: 661
<212> TYPE: DNA
<213> ORGANISM: artificial
<220> FEATURE:
<223> OTHER INFORMATION: 4D5L

<400> SEQUENCE: 78

```
ccatggcgga tatccagatg acccagtccc cgagctccct gtccgcctct gtgggcgata      60
gggtcaccat cacctgccgt gccagtcagg atgtgaatac tgctgtagcc tggtatcaac     120
agaaaccagg aaaagctccg aaactactga tttactcggc atccttcctc tactctggag     180
tcccttctcg cttctctgga tccagatctg ggacggattt cactctgacc atcagcagtc     240
tgcagccgga agacttcgca acttattact gtcagcaaca ttatactact cctcccacgt     300
tcggacaggg taccaaggtg gagatcaaac gtacggtggc ggcgccatct gtcttcatct     360
tcccgccatc tgatgagcag cttaagtctg gaactgcctc tgttgtgtgc ctgctgaata     420
acttctatcc cagagaggcc aaagtacagt ggaaggtgga taacgccctc caatcgggta     480
actcccagga gagtgtcaca gagcaggaca gcaaggacag cacctacagc ctcagcagca     540
ccctgacgct gagcaaagca gactacgaga acacaaagt ctacgcctgc gaagtcaccc      600
atcagggcct gagctcgccc gtcacaaaga gcttcaacag gggagagtgt tgaggcgcgc     660
c                                                                     661
```

<210> SEQ ID NO 79
<211> LENGTH: 6468
<212> TYPE: DNA
<213> ORGANISM: artificial
<220> FEATURE:
<223> OTHER INFORMATION: vector pYD4D5hc

<400> SEQUENCE: 79

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata ttttctgtta ttgcttcagt gctagccgct ggggccatgg    600
ttactgattg gcgcgccgga tccgatgtaa caaaatcgac tttgttccca ctgtactttt     660
agctcgtaca aaatacaata tacttttcat ttctccgtaa acaacatgtt ttcccatgta     720
atatccttt ctattttcg ttccgttacc aactttacac atactttata tagctattca       780
cttctataca ctaaaaaact aagacaattt taattttgct gcctgccata tttcaattttg    840
ttataaattc ctataattta tcctattagt agctaaaaaa agatgaatgt gaatcgaatc     900
ctaagagaat tgctgcagaa ttcacggatt agaagccgcc gagcgggtga cagccctccg     960
aaggaagact ctcctccgtg cgtcctcgtc ttcaccggtc gcgttcctga aacgcagatg    1020
tgcctcgcgc gcactgctc cgaacaataa agattctaca atactagctt ttatggttat     1080
gaagaggaaa aattggcagt aacctggccc cacaaacctt caaatgaacg aatcaaatta    1140
acaaccatag gatgataatg cgattagttt tttagcctta tttctggggt aattaatcag    1200
cgaagcgatg attttgatc tattaacaga tatataaatg caaaaactgc ataaccactt     1260
```

```
taactaatac tttcaacatt ttcggtttgt attacttctt attcaaatgt aataaaagta   1320
tcaacaaaaa attgttaata tacctctata ctttaacgtc aaggagaaaa aacccggat    1380 cggactacta gcagctgtaa tacgactcac tatagggaat attaagctaa ttctacttca   1440
tacattttca attaagatgc agttacttcg ctgtttttca atattttctg ttattgcttc   1500
agttttagca caggaactga caactatatg cgagcaaatc ccctcaccaa ctttagaatc   1560
gacgccgtac tctttgtcaa cgactactat tttggccaac gggaaggcaa tgcaaggagt   1620
ttttgaatat tacaaatcag taacgtttgt cagtaattgc ggttctcacc cctcaacaac   1680
tagcaaaggc agccccataa acacacagta tgtttttaag cttctgcagg ctagtggtgg   1740
tggtggttct ggtggtggtg ttctggtgg tggtggttct gctagcatga ctggtggcca   1800
gcaaggccaa ggttctgagg ttcaactagt ggagtctggc ggtggcctgg tgcagccagg   1860
gggctcactc cgtttgtcct gtgcagcttc tggcttcaac attaaagaca cctatataca   1920
ctgggtgcgt caggccccgg gtaagggcct ggaatgggtt gcaaggattt atcctacgaa   1980
tggttatact agatatgccg atagcgtcaa gggccgtttc actataagcg cagacacatc   2040
caaaaacaca gcctacctgc agatgaacag cctgcgtgct gaggacactg ccgtctatta   2100
ttgttctaga tggggagggg acggcttcta tgctatggac tactgggtc aaggaaccct    2160 ggtcaccgtc tcctcggcta gcaccaaggg ccccagcgtg ttccctctgg ccccagctc    2220 caagagcacc tccggcggca cgccgcccct gggctgcctg gtgaaggatt acttcccaga   2280
gcccgtgacc gtgagctgga acagcggcgc cctgaccagc ggcgtgcaca ccttccccgc   2340
cgtgctgcag tccagcggcc tgtactccct gagcagcgtg gtgaccgtgc ccagcagcag   2400
cctgggcacc cagacctaca tctgcaatgt gaaccacaag cccagcaata ccaaggtgga   2460
taagaaggtg gagcccaaga gctgcgcggc cgcacatcat caccatcacc attgattaat   2520
taagtttaaa cccgctgatc tgataacaac agtgtagatg taacaaaatc gactttgttc   2580
ccactgtact tttagctcgt acaaaataca atatactttt catttctccg taaacaacat   2640
gttttcccat gtaatatcct tttctatttt tcgttccgtt accaacttta cacatacttt   2700
atatagctat tcacttctat acactaaaaa actaagacaa ttttaatttt gctgcctgcc   2760
atatttcaat ttgttataaa ttcctataat ttatcctatt agtagctaaa aaagatgaa    2820 tgtgaatcga atcctaagag aattgggcaa gtgcacaaac aatacttaaa taatactac    2880 tcagtaataa cctatttctt agcattttg acgaaatttg ctattttgtt agagtctttt    2940
acaccatttg tctccacacc tccgcttaca tcaacaccaa taacgccatt taatctaagc   3000
gcatcaccaa cattttctgg cgtcagtcca ccagctaaca taaaatgtaa gctctcgggg   3060
ctctcttgcc ttccaaccca gtcagaaatc gagttccaat ccaaaagttc acctgtccca   3120
cctgcttctg aatcaaacaa gggaataaac gaatgaggtt tctgtgaagc tgcactgagt   3180
agtatgttgc agtcttttgg aaatacgagt cttttaataa ctggcaaacc gaggaactct   3240
tggtattctt gccacgactc atctccgtgc agttggacga tatcaatgcc gtaatcattg   3300
accagagcca aaacatcctc cttaggttga ttacgaaaca cgccaaccaa gtatttcgga   3360
gtgcctgaac tattttata tgcttttaca agacttgaaa ttttccttgc aataaccggg    3420
tcaattgttc tctttctatt gggcacacat ataatacca gcaagtcagc atcggaatct    3480
agagcacatt ctgcggcctc tgtgctctgc aagccgcaaa cttcaccaa tggaccagaa    3540 ctacctgtga aattaataac agacatactc caagctgcct ttgtgtgctt aatcacgtat   3600
actcacgtgc tcaatagtca ccaatgccct ccctcttggc cctctccttt tcttttttcg   3660
```

```
accgaatttc ttgaagacga aagggcctcg tgatacgcct attttttatag gttaatgtca    3720
tgataataat ggtttcttag gacgatcgc ttgcctgtaa cttacacgcg cctcgtatct    3780
tttaatgatg gaataatttg ggaatttact ctgtgtttat ttattttat gttttgtatt    3840
tggattttag aaagtaaata aagaaggtag aagagttacg gaatgaagaa aaaaaaataa    3900
acaaaggttt aaaaaatttc aacaaaaagc gtactttaca tatatattta ttagacaaga    3960
aaagcagatt aaatagatat acattcgatt aacgataagt aaaatgtaaa atcacaggat    4020
tttcgtgtgt ggtcttctac acagacaaga tgaaacaatt cggcattaat acctgagagc    4080
aggaagagca agataaaagg tagtatttgt tggcgatccc cctagagtct tttacatctt    4140
cggaaaacaa aaactatttt ttcttttaatt tcttttttta cttttctattt ttaatttata    4200
tatttatatt aaaaaattta aattataatt attttttatag cacgtgatga aaaggaccca    4260
ggtggcactt ttcggggaaa tgtgcgcgga accctatttt gtttatttttt ctaaatacat    4320
tcaaatatgt atccgctcat gagacaataa ccctgataaa tgcttcaata atattgaaaa    4380
aggaagagta tgagtattca acatttccgt gtcgccctta ttcccttttt tgcggcatttt    4440
tgccttcctg ttttttgctca cccagaaacg ctggtgaaag taaaagatgc tgaagatcag    4500
ttgggtgcac gagtgggtta catcgaactg gatctcaaca gcggtaagat ccttgagagt    4560
tttcgccccg aagaacgttt tccaatgatg agcactttta aagttctgct atgtggcgcg    4620
gtattatccc gtgttgacgc cgggcaagag caactcggtc gccgcataca ctattctcag    4680
aatgacttgg ttgagtactc accagtcaca gaaaagcatc ttacgatgg catgacagta    4740
agagaattat gcagtgctgc cataaccatg agtgataaca ctgcggccaa cttacttctg    4800
acaacgatcg gaggaccgaa ggagctaacc gcttttttgc acaacatggg gatcatgta    4860
actcgccttg atcgttggga accggagctg aatgaagcca taccaaacga cgagcgtgac    4920
accacgatgc ctgtagcaat ggcaacaacg ttgcgcaaac tattaactgg cgaactactt    4980
actctagctt cccggcaaca attaatagac tggatggagg cggataaagt tgcaggacca    5040
cttctgcgct cggcccttcc ggctggctgg tttattgctg ataaatctgg agccggtgag    5100
cgtgggtctc gcggtatcat tgcagcactg gggccagatg gtaagccctc ccgtatcgta    5160
gttatctaca cgacgggcag tcaggcaact atggatgaac gaaatagaca gatcgctgag    5220
ataggtgcct cactgattaa gcattggtaa ctgtcagacc aagtttactc atatatactt    5280
tagattgatt taaaacttca tttttaattt aaaaggatct aggtgaagat cctttttgat    5340
aatctcatga ccaaaatccc ttaacgtgag ttttcgttcc actgagcgtc agaccccgta    5400
gaaaagatca aggatcttc ttgagatcct ttttttctgc gcgtaatctg ctgcttgcaa    5460
acaaaaaaac caccgctacc agcggtggtt tgtttgccgg atcaagagct accaactctt    5520
tttccgaagg taactggctt cagcagagcg cagataccaa atactgtcct tctagtgtag    5580
ccgtagttag gccaccactt caagaactct gtagcaccgc ctacatacct cgctctgcta    5640
atcctgttac cagtggctgc tgccagtggc gataagtcgt gtcttaccgg gttggactca    5700
agacgatagt taccggataa ggcgcagcgg tcgggctgaa cggggggttc gtgcacacag    5760
cccagcttgg agcgaacgac ctacaccgaa ctgagatacc tacagcgtga gcattgagaa    5820
agcgccacgc ttcccgaagg gagaaaggcg gacaggtatc cggtaagcgg cagggtcgga    5880
acaggagagc gcacgaggga gcttccaggg ggaacgcct ggtatctta tagtcctgtc    5940
gggtttcgcc acctctgact tgagcgtcga ttttgtgat gctcgtcagg ggggcgagc    6000
```

```
ctatggaaaa acgccagcaa cgcggccttt ttacggttcc tggccttttg ctggccttt      6060 gctcacatgt tctttcctgc gttatcccct gattctgtgg ataaccgtat taccgccttt    6120
gagtgagctg ataccgctcg ccgcagccga acgaccgagc gcagcgagtc agtgagcgag    6180
gaagcggaag agcgcccaat acgcaaaccg cctctcccg cgcgttggcc gattcattaa     6240
tgcagctggc acgacaggtt tcccgactgg aaagcgggca gtgagcgcaa cgcaattaat   6300
gtgagttacc tcactcatta ggcacccag gctttacact ttatgcttcc ggctcctatg   6360
ttgtgtggaa ttgtgagcgg ataacaattt cacacaggaa acagctatga ccatgattac    6420
gccaagctcg gaattaaccc tcactaaagg gaacaaaagc tggctagt                 6468
```

<210> SEQ ID NO 80
<211> LENGTH: 223
<212> TYPE: PRT
<213> ORGANISM: artificial
<220> FEATURE:
<223> OTHER INFORMATION: 4D5hp

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220
```

<210> SEQ ID NO 81
<211> LENGTH: 7100
<212> TYPE: DNA
<213> ORGANISM: artificial
<220> FEATURE:
<223> OTHER INFORMATION: vector pYD4D5hl

<400> SEQUENCE: 81

```
acggattaga agccgccgag cgggtgacag ccctccgaag gaagactctc ctccgtgcgt     60
```

-continued

```
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttcagt gctagccgct ggggccatgg     600
cggatatcca gatgacccag tccccgagct ccctgtccgc ctctgtgggc gatagggtca     660
ccatcacctg ccgtgccagt caggatgtga atactgctgt agcctggtat caacagaaac     720
caggaaaagc tccgaaacta ctgatttact cggcatcctt cctctactct ggagtccctt     780
ctcgcttctc tggatccaga tctgggacgg atttcactct gaccatcagc agtctgcagc     840
cggaagactt cgcaacttat tactgtcagc aacattatac tactcctccc acgttcggac     900
agggtaccaa ggtggagatc aaacgtacgg tggcggcgcc atctgtcttc atcttcccgc     960
catctgatga gcagcttaag tctggaactg cctctgttgt gtgcctgctg aataacttct    1020
atcccagaga ggccaaagta cagtggaagg tggataacgc cctccaatcg ggtaactccc    1080
aggagagtgt cacagagcag gacagcaagg acagcaccta cagcctcagc agcaccctga    1140
cgctgagcaa agcagactac gagaaacaca agtctacgc ctgcgaagtc acccatcagg    1200
gcctgagctc gcccgtcaca aagagcttca caggggaga gtgttgaggc gcgccggatc    1260
cgatgtaaca aaatcgactt tgttcccact gtacttttag ctcgtacaaa atacaatata    1320
cttttcattt ctccgtaaac aacatgtttt cccatgtaat atccttttct attttttcgtt    1380 ccgttaccaa ctttacacat actttatata gctattcact tctatacact aaaaaactaa    1440
gacaattttt attttgctgc ctgccatatt tcaatttgtt ataaattcct ataatttatc    1500
ctattagtag ctaaaaaaag atgaatgtga atcgaatcct aagagaattg ctgcagaatt    1560
cacggattag aagccgccga gcgggtgaca gccctccgaa ggaagactct cctccgtgcg    1620
tcctcgtctt caccggtcgc gttcctgaaa cgcagatgtg cctcgcgccg cactgctccg    1680
aacaataaag attctacaat actagctttt atggttatga agaggaaaaa ttggcagtaa    1740
cctggcccca caaaccttca aatgaacgaa tcaaattaac aaccatagga tgataatgcg    1800
attagttttt tagccttatt tctggggtaa ttaatcagcg aagcgatgat ttttgatcta    1860
ttaacagata tataaatgca aaaactgcat aaccactttta actaatactt tcaacatttt    1920
cggtttgtat tacttcttat tcaaatgtaa taaaagtatc aacaaaaaat tgttaatata    1980
cctctatact ttaacgtcaa ggagaaaaaa ccccggatcg gactactagc agctgtaata    2040
cgactcacta tagggaatat taagctaatt ctacttcata cattttcaat taagatgcag    2100
ttacttcgct gtttttcaat attttctgtt attgcttcag ttttagcaca ggaactgaca    2160
actatatgcg agcaaatccc ctcaccaact ttagaatcga cgccgtactc tttgtcaacg    2220
actactattt tggccaacgg gaaggcaatg caaggagttt ttgaatatta caaatcagta    2280
acgtttgtca gtaattgcgg ttctcacccc tcaacaacta gcaaaggcag ccccataaac    2340
acacagtatg tttttaagct tctgcaggct agtggtggtg gtggttctgg tggtggtggt    2400
```

```
tctggtggtg gtggttctgc tagcatgact ggtggccagc aaggccaaga ggttcaacta    2460
gtggagtctg gcggtggcct ggtgcagcca gggggctcac tccgtttgtc ctgtgcagct    2520
tctggcttca acattaaaga cacctatata cactgggtgc gtcaggcccc gggtaagggc    2580
ctggaatggg ttgcaaggat ttatcctacg aatggttata ctagatatgc cgatagcgtc    2640
aagggccgtt tcactataag cgcagacaca tccaaaaaca cagcctacct gcagatgaac    2700
agcctgcgtg ctgaggacac tgccgtctat tattgttcta gatggggagg ggacggcttc    2760
tatgctatgg actactgggg tcaaggaacc ctggtcaccg tctcctcggc tagcaccaag    2820
ggcccccagcg tgttccctct ggcccccagc tccaagagca cctccggcgg caccgccgcc    2880
ctgggctgcc tggtgaagga ttacttccca gagcccgtga ccgtgagctg gaacagcggc    2940
gccctgacca cggcgtgca cacctttccc gccgtgctgc agtccagcgg cctgtactcc    3000
ctgagcagcg tggtgaccgt gcccagcagc agcctgggca cccagaccta catctgcaat    3060
gtgaaccaca gcccagcaa taccaaggtg gataagaagg tggagcccaa gagctgcgcg    3120
gccgcacatc atcaccatca ccattgatta attaagttta aacccgctga tctgataaca    3180
acagtgtaga tgtaacaaaa tcgactttgt tcccactgta cttttagctc gtacaaaata    3240
caatatactt ttcatttctc cgtaaacaac atgttttccc atgtaatatc cttttctatt    3300
tttcgttccg ttaccaactt tacacatact ttatatagct attcacttct atacactaaa    3360
aaactaagac aattttaatt ttgctgcctg ccatatttca atttgttata aattcctata    3420
atttatccta ttagtagcta aaaaagatg aatgtgaatc gaatcctaag agaattgggc    3480
aagtgcacaa acaatactta ataaatact actcagtaat aacctatttc ttagcatttt    3540
tgacgaaatt tgctatttg ttagagtctt ttacaccatt tgtctccaca cctccgctta    3600
catcaacacc aataacgcca tttaatctaa gcgcatcacc aacattttct ggcgtcagtc    3660
caccagctaa cataaaatgt aagctctcgg ggctctcttg ccttccaacc cagtcagaaa    3720
tcgagttcca atccaaaagt tcacctgtcc cacctgcttc tgaatcaaac aagggaataa    3780
acgaatgagg tttctgtgaa gctgcactga gtagtatgtt gcagtctttt ggaaatacga    3840
gtcttttaat aactggcaaa ccgaggaact cttggtattc ttgccacgac tcatctccgt    3900
gcagttggac gatatcaatg ccgtaatcat tgaccagagc caaaacatcc tccttaggtt    3960
gattacgaaa cacgccaacc aagtatttcg gagtgcctga actattttta tatgctttta    4020
caagacttga aattttcctt gcaataaccg ggtcaattgt tctctttcta ttgggcacac    4080
atataatacc cagcaagtca gcatcggaat ctagagcaca ttctgcggcc tctgtgctct    4140
gcaagccgca aactttcacc aatggaccag aactacctgt gaattaata acagacatac    4200
tccaagctgc ctttgtgtgc ttaatcacgt atactcacgt gctcaatagt caccaatgcc    4260
ctccctcttg gccctctcct tttcttttt cgaccgaatt tcttgaagac gaaagggcct    4320
cgtgatacgc ctatttttat aggttaatgt catgataata atggtttctt aggacggatc    4380
gcttgcctgt aacttacacg cgcctcgtat cttttaatga tggaataatt tgggaattta    4440
ctctgtgttt atttattttt atgttttgta tttggatttt agaaagtaaa taagaaggt    4500
agaagagtta cggaatgaag aaaaaaaat aaacaaggt ttaaaaaatt caacaaaaa    4560
gcgtacttta catatatatt tattagacaa gaaaagcaga ttaaatagat atacattcga    4620
ttaacgataa gtaaaatgta aaatcacagg attttcgtgt gtggtcttct acacagacaa    4680
gatgaaacaa ttcggcatta atacctgaga gcaggaagag caagataaaa ggtagtattt    4740
gttggcgatc cccctagagt cttttacatc ttcggaaaac aaaaactatt ttttcttaa    4800
```

-continued

```
tttcttttttt tactttctat ttttaattta tatatttata ttaaaaaatt taaattataa    4860
ttatttttat agcacgtgat gaaaaggacc caggtggcac ttttcgggga aatgtgcgcg    4920
gaacccctat ttgtttattt ttctaaatac attcaaatat gtatccgctc atgagacaat    4980
aaccctgata aatgcttcaa taatattgaa aaaggaagag tatgagtatt caacatttcc    5040
gtgtcgccct tattccctttt tttgcggcat tttgccttcc tgtttttgct cacccagaaa    5100
cgctggtgaa agtaaaagat gctgaagatc agttgggtgc acgagtgggt tacatcgaac    5160
tggatctcaa cagcggtaag atccttgaga gttttcgccc cgaagaacgt tttccaatga    5220
tgagcacttt taaagttctg ctatgtggcg cggtattatc ccgtgttgac gccgggcaag    5280
agcaactcgg tcgccgcata cactattctc agaatgactt ggttgagtac tcaccagtca    5340
cagaaaagca tcttacggat ggcatgacag taagagaatt atgcagtgct gccataacca    5400
tgagtgataa cactgcggcc aacttacttc tgacaacgat cggaggaccg aaggagctaa    5460 ccgcttttt gcacaacatg ggggatcatg taactcgcct tgatcgttgg gaaccggagc    5520
tgaatgaagc cataccaaac gacgagcgtg acaccacgat gcctgtagca atggcaacaa    5580
cgttgcgcaa actattaact ggcgaactac ttactctagc ttcccggcaa caattaatag    5640
actggatgga ggcggataaa gttgcaggac cacttctgcg ctcggccctt ccggctggct    5700
ggtttattgc tgataaatct ggagccggtg agcgtgggtc tcgcggtatc attgcagcac    5760
tggggccaga tggtaagccc tcccgtatcg tagttatcta cacgacgggc agtcaggcaa    5820
ctatggatga acgaaataga cagatcgctg agataggtgc ctcactgatt aagcattggt    5880
aactgtcaga ccaagtttac tcatatatac tttagattga tttaaaactt cattttttaat    5940 ttaaaaggat ctaggtgaag atcctttttg ataatctcat gaccaaaatc ccttaacgtg    6000
agttttcgtt ccactgagcg tcagaccccg tagaaaagat caaaggatct tcttgagatc    6060 cttttttttct gcgcgtaatc tgctgcttgc aaacaaaaaa accaccgcta ccagcggtgg    6120
tttgtttgcc ggatcaagag ctaccaactc tttttccgaa ggtaactggc ttcagcagag    6180
cgcagatacc aaatactgtc cttctagtgt agccgtagtt aggccaccac ttcaagaact    6240
ctgtagcacc gcctacatac ctcgctctgc taatcctgtt accagtggct gctgccagtg    6300
gcgataagtc gtgtcttacc gggttggact caagacgata gttaccggat aaggcgcagc    6360
ggtcgggctg aacggggggt tcgtgcacac agcccagctt ggagcgaacg acctacaccg    6420
aactgagata cctacagcgt gagcattgag aaagcgccac gcttcccgaa gggagaaagg    6480
cggacaggta tccggtaagc ggcagggtcg aacaggaga cgcacgagg gagcttccag    6540 gggggaacgc ctggtatctt tatagtcctg tcgggtttcg ccacctctga cttgagcgtc    6600
gatttttgtg atgctcgtca ggggggccga gcctatggaa aaacgccagc aacgcggcct    6660
ttttacggtt cctggccttt tgctggcctt ttgctcacat gttctttcct gcgttatccc    6720
ctgattctgt ggataaccgt attaccgcct ttgagtgagc tgataccgct cgccgcagcc    6780
gaacgaccga gcgcagcgag tcagtgagcg aggaagcgga agagcgccca atacgcaaac    6840
cgcctctccc cgcgcgttgg ccgattcatt aatgcagctg gcacgacagg tttcccgact    6900
ggaaagcggg cagtgagcgc aacgcaatta atgtgagtta cctcactcat taggcacccc    6960
aggctttaca ctttatgctt ccggctccta tgttgtgtgg aattgtgagc ggataacaat    7020
ttcacacagg aaacagctat gaccatgatt acgccaagct cggaattaac cctcactaaa    7080
gggaacaaaa gctggctagt                                                7100
```

```
<210> SEQ ID NO 82
<211> LENGTH: 214
<212> TYPE: PRT
<213> ORGANISM: artificial
<220> FEATURE:
<223> OTHER INFORMATION: 4D5lp

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 83
<211> LENGTH: 4
<212> TYPE: PRT
<213> ORGANISM: artificial
<220> FEATURE:
<223> OTHER INFORMATION: C-terminal residues of junction region
      (SEQ ID No. 10)

<400> SEQUENCE: 83

Ser Pro Gly Lys
1

<210> SEQ ID NO 84
<211> LENGTH: 10
<212> TYPE: PRT
<213> ORGANISM: artificial
<220> FEATURE:
<223> OTHER INFORMATION: Myc epitope of junction region (SEQ ID No. 10)

<400> SEQUENCE: 84

Glu Gln Lys Leu Ile Ser Glu Glu Asp Leu
1               5                   10
```

```
<210> SEQ ID NO 85
<211> LENGTH: 4
<212> TYPE: PRT
<213> ORGANISM: artificial
<220> FEATURE:
<223> OTHER INFORMATION: Residues 18-21 of junction region
      (SEQ ID No. 10)

<400> SEQUENCE: 85

Asn Gly Ala Ala
1

<210> SEQ ID NO 86
<211> LENGTH: 4
<212> TYPE: PRT
<213> ORGANISM: artificial
<220> FEATURE:
<223> OTHER INFORMATION: N-terminal residues of junction region
      (SEQ ID No. 10)

<400> SEQUENCE: 86

Thr Val Glu Ser
1

<210> SEQ ID NO 87
<211> LENGTH: 5
<212> TYPE: PRT
<213> ORGANISM: artificial
<220> FEATURE:
<223> OTHER INFORMATION: AB-loop sequence AA143ff

<400> SEQUENCE: 87

Leu Thr Lys Asn Gln
1               5

<210> SEQ ID NO 88
<211> LENGTH: 7
<212> TYPE: PRT
<213> ORGANISM: artificial
<220> FEATURE:
<223> OTHER INFORMATION: EF loop sequence AA198ff

<400> SEQUENCE: 88

Asp Lys Ser Arg Trp Gln Gln
1               5
```